United States Patent
Eaton et al.

(10) Patent No.: US 6,583,301 B1
(45) Date of Patent: Jun. 24, 2003

(54) LIPIDS

(75) Inventors: Michael Anthony William Eaton, Oxon (GB); Timothy John Norman, Buckinghamshire (GB); David Parker, Durham (GB); Terence Seward Baker, Middlesex (GB); Andrew Neil Charles Weir, Berkshire (GB); Catherine Fiona Catterall, Bucks (GB)

(73) Assignee: Celltech R & D Limited, Berkshire (GB)

( * ) Notice: Subject to any disclaimer, the term of this patent is extended or adjusted under 35 U.S.C. 154(b) by 0 days.

(21) Appl. No.: 09/646,766

(22) PCT Filed: Apr. 8, 1999

(86) PCT No.: PCT/GB99/01076

§ 371 (c)(1),
(2), (4) Date: Nov. 20, 2000

(87) PCT Pub. No.: WO99/52858

PCT Pub. Date: Oct. 21, 1999

(30) Foreign Application Priority Data

Apr. 8, 1998 (GB) ............................................. 9807727
Oct. 1, 1998 (GB) ............................................. 9821407

(51) Int. Cl.⁷ ...................... C07C 231/00; C07C 233/07

(52) U.S. Cl. ............................. 554/35; 554/68; 514/613
(58) Field of Search ............................ 514/613; 554/68, 554/35

(56) References Cited

FOREIGN PATENT DOCUMENTS

| WO | WO 96/17823 | 6/1996 |
|---|---|---|
| WO | 97/18185 | * 5/1997 |
| WO | WO 97/18185 | 5/1997 |
| WO | 96/17823 | * 6/1997 |
| WO | WO 97/45069 | 12/1997 |
| WO | 97/45069 | * 12/1997 |
| WO | WO 98/13026 | 4/1998 |
| WO | 98/13026 | * 4/1998 |
| WO | WO 98/51285 | 11/1998 |
| WO | WO 99/02191 | 1/1999 |
| WO | WO 99/08997 | 2/1999 |

* cited by examiner

Primary Examiner—Deborah D. Carr
(74) Attorney, Agent, or Firm—Sughrue Mion, PLLC

(57) ABSTRACT

Bipolar lipids are described which are able to form complexes with polyanions. The lipids comprise a cationic head linked to a hydrophobic backbone and a hydrophilic tail and are capable of self assembly to form stable complexes in aqueous solutions. The lipids are of particular use for the delivery of bioactive substances such as nucleic acids to cells in vitro and especially in vivo.

43 Claims, No Drawings

LIPIDS

This invention relates to a series of bipolar lipids and to their use to deliver bioactive substances to cells.

To be effective, many pharmaceutical agents need to be efficiently delivered to the cytoplasm of a eucaryotic cell. For many low molecular weight compounds of low to moderate polarity this is not a problem since such molecules can pass directly through the plasma membrane of the cell and into the cytoplasm. Direct passage is not available to other compounds of greater polarity or high molecular weight and these generally enter the cell by receptor mediated endocytosis or phagocytosis. These mechanisms are not efficient however with all sizes and types of molecule. In particular, large, polyanionic compounds are not readily taken up by cells when delivered to them in aqueous solution.

One general solution to this problem is to couple any poorly transported pharmaceutical agent to a carrier which itself is readily taken up into the cytoplasm of a cell. This is not always satisfactory however, since coupling to the carrier may have an undesirable effect on the metabolism and/or antigenicity of the pharmaceutical agent and/or it may be difficult to recover the desired biological activity from the resulting conjugate once inside the cell.

An alternative solution is to formulate the pharmaceutical agent with a delivery vehicle which is soluble in aqueous solutions but which can also mimic naturally occurring cell membrane constituents. This encourages fusion of the vehicle with a cell membrane and subsequent delivery of any associated pharmaceutical agent to the cytoplasm.

Amphiphilic lipids have frequently been used for this purpose. These typically have a hydrophobic backbone composed of one or more hydrocarbons and a hydrophilic polar head group containing one or more ionisable groups, to facilitate the transport of macromolecules to and across the plasma membrane of cells and into the cytoplasm. The polarity of the head group may be controlled by the selection of the number and/or type of ionisable groups to achieve a range of negatively charged (anionic), neutral or positively charged (cationic) lipids.

For the delivery of polyanions it is generally advantageous to use cationic lipids. The advent of gene therapy and the need to deliver anionic molecules such as nucleic acids to mammalian cells has provided much impetus to the development of this class of lipids. First generation compounds include those with a monocation head group such as N-[1(2,3-dioleyloxy)propyl]-N,N,N-trimethylammonium chloride [DOTMA; Felgner, P L and Ringold, G M, Nature, 337 387–388 (1989)], 1,2-dimyristyloxypropyl-3-dimethylhydroxyethylammonium bromide [DMRIE; Zabner, J et al J. Biol. Chem, 270, 18997–19007 (1995)] and 3β[N-($N^1,N^1$-dimethylaminoethane)carbamoyl]cholesterol [DC-Chol; Farhood, H et al, Biochim. Biophys. Acta. 1111, 239–246 (1992)] and those with a polycation head group such as dioctadecylamidoglycylspermine [DOGS; Behr, J-P, et al, Proc. Natl. Acad. Sci. 86, 6982–6986 (1989)].

In an effort to improve the properties of these early compounds for in vivo delivery of polyanions many more cationic lipids have been developed in which the nature and size of the hydrophobic backbone and/or the cationic head group have been varied (see for example International Patent Specifications Nos. WO95/21931, WO96/10038, WO96/17823, WO96/18273, WO96/25508, WO96/26179, WO96/41606, WO97/18185, WO97/25339, WO97/3010 and WO97/31934).

The goal in the development of cationic lipids for in vivo use is to provide a molecule which is simple to use in a clinical setting; which is robust; which forms small stable complexes over wide pH and ionic strength ranges; which is non-toxic; and which is capable of delivering a high concentration of polyanion to a cell.

We have now developed a class of lipid which meets these requirements. Importantly, our lipids are capable of self-assembly and will form stable complexes in aqueous solutions. The lipids are able to efficiently compact polyanions to give defined particle sizes of less than 500 nm. The lipid-polyanion complex remains associated over wide pH and ionic strength ranges and is able to efficiently deliver high concentrations of polyanions to cells.

Thus according to one aspect of the invention we provide a bipolar lipid comprising a cationic head (1) a hydrophobic backbone (2) and a hydrophilic tail (3) in which:

(A) the cationic head comprises two or more cationic centres, each centre being covalently linked to one or more others by one or more carbon containing spacer groups;

(B) the hydrophobic backbone comprises one or more hydrocarbon chains; and (C) the hydrophilic tail comprises one or more hydrophilic hydrocarbons each containing two or more atoms or groups capable of being solvated by water;

each of said components (1) to (3) being covalently linked head (1) to backbone (2) to tail (3) and arranged such that at least one hydrocarbon chain in the hydrophobic backbone (2) is covalently linked to a carbon atom of a spacer group in the cationic head (1) and each hydrophilic hydrocarbon in the hydrophilic tail (3) is covalently linked to a chain in the backbone (2) to achieve at least a ten atom spacing along the chain between the tail (3) and the head (1).

In the lipids according to the invention, each cationic centre in the cationic head (1) may be provided by one or more heteroatoms capable of retaining a positive charge at a pH in the range from around pH 2.0 to around pH 10.0. In practice, whether a heteroatom will retain a positive charge in this pH range will depend on the nature and number of any other atoms or groups attached to it. Thus particular examples of suitable cationic centres include primary, secondary, tertiary and quaternary amino groups, sulphonium and phosphonium groups.

The number of cationic centres may be varied as desired depending on the intended use of the lipid of the invention. At least two centres will be present, but three, four, five, six, seven, eight or more may be optionally incorporated. More than one type of centre may be present, for example mixtures of amino groups may be accommodated, and/or sulphonium and/or phosphonium groups.

In one general preference each cationic centre is an amino group. Particularly useful amino groups include primary and secondary amino groups. The number of cationic centres in the cationic head (1) will preferably be from three to six.

Each cationic centre will in general be separated from any other centre by spacer groups arranged to link the centres in a linear (straight and/or branched) or cyclic fashion. The overall effect may be a cationic head (1) which has a straight and/or branched linear structure, a cyclic structure, or a mixture of straight and/or branched linear and cyclic structures. More than one type of spacer group may be present in a cationic head (1). Where desired a spacer group may form a terminal group on the cationic head (1), acting as a substituent on a cationic centre rather than a group connecting centres together.

Each spacer group will in general be non-ionic and contain at least one carbon atom. Suitable groups include optionally substituted aliphatic, cycloaliphatic, heteroaliphatic, heterocycloaliphatic, aromatic or heteroaromatic groups.

Particular examples of optionally substituted aliphatic spacer groups include optionally substituted $C_{1-10}$aliphatic chains such as optionally substituted straight or branched $C_{1-6}$alkylene, $C_{2-6}$alkenylene or $C_{2-6}$alkynylene chains.

Heteroaliphatic spacer groups include the aliphatic chains just described but with each chain additionally containing one, two, three or four heteroatoms or heteroatom-containing groups. Particular heteroatoms or groups include atoms or groups $L^2$ where $L^2$ is as defined below for $L^1$ when $L^1$ is a linker atom or group. Each $L^2$ atom or group may interrupt the aliphatic chain, or may be positioned at its terminal carbon atom to connect the chain to the atom or group $R^1$.

Particular examples of aliphatic spacer groups include optionally substituted —$CH_2$—, —$CH_2CH_2$—, —CH($CH_3$)—, —C($CH_3$)$_2$—, —($CH_2$)$_2CH_2$—, —CH($CH_3$)$CH_2$—, —($CH_2$)$_3CH_2$—, —CH($CH_3$)$CH_2CH_2$—, —$CH_2$CH($CH_3$)$CH_2$—, —C($CH_3$)$_2CH_2$—, —($CH_2$)$_4$$CH_2$—, —($CH_2$)$_5CH_2$—, —CHCH—, —CHCHCH$_2$—, —$CH_2$CHCH—, —CHCHCH$_2$CH$_2$—, —$CH_2$CHCHCH$_2$—, —($CH_2$)$_2$CHCH—, —CC—, —CCCH$_2$—, —$CH_2$CC—, —CCCH$_2$CH$_2$—, —$CH_2$CCCH$_2$—, or —($CH_2$)$_2$CC— chains. Where appropriate each of said chains may be optionally interrupted by one or two atoms and/or groups $L^2$ to form an optionally substituted heteroaliphatic spacer group. Particular examples include optionally substituted —$L^2CH_2$—, —$CH_2L^2CH_2$—, —$L^2$ ($CH_2$)$_2$—, —$CH_2L^2$($CH_2$)$_2$—, —($CH_2$)$_2L^2CH_2$—, —$L^2$($CH_2$)$_3$— and $CH_2$)$_2L^2$($CH_2$)$_2$— chains. The optional substituents which may be present on aliphatic or heteroaliphatic spacer groups include one, two, three or more substituents selected from halogen atoms, e.g. fluorine, chlorine, bromine or iodine atoms, or hydroxyl, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, or $C_{1-6}$alkylthio e.g. methylthio or ethylthio. Particular examples of substituted spacer groups include those specific chains just described substituted by one, two, or three halogen atoms such as fluorine atoms, for example chains of the type —CH($CF_3$)—, —C($CF_3$)$_2$— —$CH_2$CH($CF_3$)—, —$CH_2$C($CF_3$)$_2$—, —CH($CF_3$)— and —C($CF_3$)$_2CH_2$—.

Optionally substituted cycloaliphatic spacer groups in the cationic head (1) include optionally substituted $C_{3-10}$ cycloaliphatic groups. Particular examples include optionally substituted $C_{3-10}$cycloalkylene, e.g. $C_{3-7}$cycloalkylene, $C_{3-10}$cycloalkenylene e.g. $C_{3-7}$cycloalkenylene or $C_{3-10}$cycloalkynylene e.g. $C_{3-7}$cycloalkynylene groups.

Particular examples of cycloaliphatic spacer groups include optionally substituted cyclopropylene, cyclobutylene, cyclopentylene, cyclohexylene, cycloheptylene, 2-cyclobuten-1-ylene, 2-cyclopenten-1-ylene and 3-cyclopenten-1-ylene groups.

Optionally substituted heterocycloaliphatic spacer groups include the optionally substituted cycloaliphatic groups just described but with each group additionally containing one, two, three or four heteroatoms or heteroatom-containing groups $L^2$ as just defined.

The optional substituents which may be present on the cycloaliphatic or heterocycloaliphatic spacer groups include one, two, three or more substituents selected from halogen atoms $C_{1-6}$alkyl, e.g. methyl or ethyl, halo$C_{1-6}$alkyl, e.g. halomethyl or haloethyl such as difluoromethyl or trifluoromethyl, hydroxyl, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, or $C_{1-6}$alkylthio e.g. methylthio or ethylthio groups.

Optionally substituted aromatic spacer groups include for example monocyclic $C_{6-12}$ aromatic groups, such as optionally substituted phenylene.

Optionally substituted heteroaromatic spacer groups, include for example optionally substituted monocyclic $C_{1-9}$ heteroaromatic groups containing for example one, two, three or four heteroatoms selected from oxygen, sulphur or nitrogen atoms. Monocyclic heteroaromatic groups include for example five- or six-membered heteroaromatic groups containing one, two, three or four heteroatoms selected from oxygen, sulphur or nitrogen atoms.

Optional substituents which may be present on the aromatic or heteroaromatic spacer groups include one, two, three or more substituents selected from those just described in relation to cycloaliphatic and heterocycloaliphatic spacer groups.

In one general preference each spacer group in the cationic head (1) is preferably an optionally substituted straight or branched $C_{1-6}$alkylene chain. Particularly useful chains include —($CH_2$)$_2$—, —($CH_2$)$_3$— and —$CH_2$)$_4$— chains.

In the lipids of the invention at least one spacer group connecting two cationic centres is covalently linked through one of its carbon atoms to a hydrocarbon chain of the hydrophobic backbone (2). Where desired any other available carbon atom or heteroatom in the, or any other, spacer group, or any available atom in a cationic centre, may be additionally linked to the same or other hydrocarbon chains making up the backbone (2). It is generally preferred however to link the backbone (2) and cationic head (1) at one carbon atom in one spacer group.

The hydrophobic backbone (2) in the lipids according to the invention may comprise one or more hydrocarbon chains. Each hydrocarbon may be for example an optionally substituted straight or branched aliphatic or heteroaliphatic chain containing a minimum of ten up to a maximum of around one hundred chain-linked atoms as described in more detail below. The hydrocarbon may be attached either directly or indirectly through a linker atom or group to the cationic head (1). Particular examples of suitable linker groups are those represented by the group $L^1$ described below. As explained above, more than one hydrocarbon chain may be attached to the head group but a preferred class of lipids according to the invention has one or two hydrocarbon chains as just described indirectly linked through a linker atom or group to a carbon atom in a spacer group connecting two cationic centres in the cationic head (1).

The hydrophilic tail (3) in the lipids according to the invention may in general be one or more hydrophilic hydrocarbons having little or no overall positive or negative charge and containing a minimum of two up to a maximum of around one hundred atoms or groups capable of being solvated by water. Each hydrophilic hydrocarbon in the hydrophilic tail (3) may be attached directly or indirectly through a linker atom or group to a hydrocarbon chain of the hydrocarbon backbone (2). The attachment point may be anywhere on the hydrocarbon chain provided that it is at least ten atoms along the chain, excluding branches, from the terminal carbon atom connecting the hydrophobic backbone (2) to the cationic head (1). In one general preference the attachment point may be at a terminal carbon atom of a hydrocarbon chain distal to the chain carbon atom attached to the cationic head (1). Particular examples of suitable hydrophilic hydrocarbons which constitute the hydrophilic tail (3) are described in more detail below.

A particularly useful group of lipids according to the invention may be represented by the formula (1):

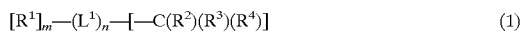

(1)

wherein $R^1$ is a hydrocarbon chain optionally substituted by one or more hydrophilic hydrocarbons each containing two or more atoms or groups capable of being solvated by water, provided that at least one hydrocarbon chain is substituted by at least one hydrophilic hydrocarbon and each hydrophilic hydrocarbon is attached to the hydrocarbon chain to achieve at least a ten atom spacing along the chain between the hydrophilic hydrocarbon and the group —$(L^1)_n$—[—C$(R^2)(R^3)(R^4)$];

m is an integer from 1 to 6;

$L^1$ is a linker atom or group;

n is zero or the integer 1;

—[—C$(R^2)(R^3)(R^4)$] is a cationic head in which $R^2$ is a hydrogen atom or an optionally substituted aliphatic, cycloaliphatic, heteroaliphatic, heterocycloaliphatic, aromatic or heteroaromatic group optionally containing one or more cationic centres, and $R^3$ and $R^4$ which may be the same or different is each an optionally substituted aliphatic, cycloaliphatic, heteroaliphatic, heterocycloaliphatic, aromatic or heteroaromatic group containing one or more cationic centres, or $R^3$ and $R^4$ together with the carbon atom to which they are attached form a cycloaliphatic, heterocycloaliphatic, aromatic or heteroaromatic group containing two or more cationic centres;

and the salts, solvates and hydrates thereof.

In the compounds of formula (1), the optionally substituted aliphatic, cycloaliphatic, heteroaliphatic, heterocycloaliphatic, aromatic or heteroaromatic group represented by $R^2$, $R^3$ and $R^4$ may each be an optionally substituted $C_{1-30}$ aliphatic, $C_{3-10}$ cycloaliphatic, $C_{1-30}$ heteroaliphatic, $C_{3-10}$ heterocycloaliphatic, $C_{6-12}$ aromatic or $C_{1-9}$ heteroaromatic group, each containing one or more cationic centres. Particular examples of such groups include those generally and specifically described above in relation to the spacer groups present in the cationic head (1) with the additional presence of one or more cationic centres as defined herein.

In general in the lipids of the invention when the hydrophobic backbone (2) and cationic head (1) are joined indirectly by a linker atom or group, as represented by $L^1$ in compounds of formula (1) when n is 1, then the linker atom or group-may be any multivalent atom or group. Particular examples of suitable linker atoms or groups include those of formula —$(Alk^1)_r(X^1)_s(Alk^2)_t$— where $X^1$ is an —O— or —S— atom or a —C(O)—, —C(O)O—, —C(S)—, —S(O), —S(O)$_2$— —N(R$^5$)—, [where R$^5$ is a hydrogen atom, straight or branched alkyl group such as a methyl or ethyl group or an —Alk$^1$X$^1$— chain], —CON(R$^5$)—, —OC(O)N(R$^5$)—, —CSN(R$^5$)—, —N(R$^5$)CO—, N(R$^5$)C(O)O—, —N(R$^5$)CS—, —S(O)N(R$^5$)—, —S(O)$_2$N(R$^5$)—, —N(R$^5$)S(O)—, —N(R$^5$)S(O)$_2$—, —N(R$^5$)CON(R$^5$)—, or —N(R$^5$)SO$_2$N(R$^5$)— group [where any of these groups contains two R$^5$ substituents these may be the same or different]; Alk$^1$ and Alk$^2$ which may be the same or different is each an optionally substituted straight or branched $C_{1-6}$alkylene, $C_{2-6}$alkenylene or $C_{2-6}$alkynylene chain optionally interrupted or terminated by one or more, e.g. one, two or three, carbocyclic or heterocarbocyclic groups and/or heteroatoms or heteroatom containing groups $X^1$ as just defined, and r, s, and t, which may be the same or different, is each zero or the integer 1, provided that when one of r, s or t is zero at least one of the remainder is the integer 1.

Carbocyclic groups which may interrupt the groups Alk$^1$ and Alk$^2$ include for example optionally substituted $C_{4-8}$cycloalkyl, e.g. optionally substituted cyclopentyl or cyclohexyl groups, or optionally substituted $C_{4-8}$cycloalkenyl, e.g. optionally substituted cyclopentenyl or cyclohexenyl groups. Heterocarbocyclic groups include for example carbocyclic groups of the types just mentioned containing one or more heteroatoms or heteroatom-containing groups $X^1$ as defined above. Optional substituents which may be present on the chains represented by Alk$^1$ and Alk$^2$ and the carbocyclic or heterocarbocyclic groups which can interrupt or terminate them include one, two or three substituents selected from halogen atoms, e.g. fluorine, chlorine, bromine or iodine atoms or $C_{1-3}$alkyl, e.g. methyl or ethyl, or $C_{1-3}$alkoxy e.g. methoxy or ethoxy groups.

It will be appreciated that the linker atom or group will be at least divalent in the instance where one hydrocarbon chain in the hydrophobic backbone (2) is attached to it. Where it is desired to attach more than one hydrocarbon chain to the linker the latter will need to be selected with an appropriate valency and this will generally mean that at least one of Alk$^1$ or Alk$^2$ will need to be present in a branched form and with the requisite number of $X^1$ atoms or groups to achieve the desired coupling.

Particular examples of linker groups include groups of formula —$X^1$Alk$^2$— where $X^1$ is as defined above and Alk$^2$ is an optionally substituted —CH$_2$—, —(CH$_2$)$_2$—, —(CH$_2$)$_3$—, —(CH$_2$)$_4$—, —(CH$_2$)$_5$— or —(CH$_2$)$_6$— chain; groups of formula [X$^1$]$_2$Alk$^1$X$^1$Alk$^2$ where Alk$^1$ is a —CH$_2$CH< group and X$^1$ and Alk$^2$ are as just defined or a group of formula [X$^1$]$_2$Alk$^1$Alk$^2$ where X$^1$, Alk$^1$ and Alk$^2$ are as just defined.

Each hydrocarbon chain in the hydrophobic backbone (2) of the lipids according to the invention and as represented by $R^1$ in compounds of formula (1) may be a $C_{10}$ up to about a $C_{60}$ hydrocarbon chain, for example a $C_{16}$ to $C_{60}$ hydrocarbon chain such as a $C_{18}$ to $C_{48}$ hydrocarbon chain.

In particular, the chain may be an optionally substituted $C_{10-60}$ aliphatic chain such as an optionally substituted straight or branched $C_{10-60}$alkylene, $C_{10-60}$alkenylene or $C_{10-60}$alkynylene chain. Optional substituents which may be present on such chains include one or more halogen atoms, e.g. fluorine, chlorine, bromine or iodine atoms, or haloC$_{1-6}$alkyl, e.g. —CF$_3$ groups. Where desired each alkylene, alkenylene or alkynylene chain may be interrupted by one or more oxygen or sulphur atoms or optionally substituted $C_{5-7}$cycloalkyl, e.g. cyclopentyl or cyclohexyl, $C_{5-7}$cycloalkenyl, e.g. cyclopentenyl or cyclohexenyl, —C(O)—, —C(S)—, —C(O)N(R$^5$)—, —C(S)N(R$^5$)—, —N(R$^5$)C(O)—, —N(R$^5$)C(S)—, —C(O)O—, —C(O)S—, —OC(O)N(R$^5$)—, —S(O)—, —S(O$_2$)—, —S(O)N(R$^5$)—, —S(O)$_2$N(R$^5$)—, —N(R$^5$)S(O)—, —N(R$^5$)S(O)$_2$—, —N(R$^5$)C(O)N(R$^5$)—, —N(R$^5$)C(S)N(R$^5$)—, —N(R$^5$)S(O)N(R$^5$)— or —N(R$^5$)S(O)$_2$N(R$^5$)— groups. Optional substituents which may be present on cycloalkyl or cycloalkenyl groups of this type include one or more halogen atoms or haloalkyl groups as just described. It will be appreciated that when the hydrocarbon chain in the hydrophobic backbone (2) is an alkenylene or alkynylene chain it may have more than one unsaturated group.

As generally explained above, the hydrophilic tail (3) in the lipids according to the invention may be formed by one or more hydrophilic hydrocarbons, each attached to a hydrocarbon chain in the hydrophobic backbone (2), for example as generally represented by $R^1$ in compounds of formula (1). Each hydrophilic hydrocarbon may be an aliphatic, heteroaliphatic, cycloaliphatic, polycycloaliphatic, heterocycloaliphatic or polyheterocycloaliphatic group. Particular examples of aliphatic groups include alkyl, alkenyl or alkynyl groups. Cycloaliphatic groups include cycloalkyl or cycloalkenyl groups. Polycycloaliphatic groups include two or more cycloalkyl or cycloalkenyl groups either joined directly or indirectly through a linker atom or group, for example a linker atom or group $L^2$ where $L^2$ is an atom or group as described above for the group $L^1$. Each of these aliphatic, cycloaliphatic or polycycloaliphatic groups may be optionally interrupted by one or more heteroatoms or heteroatom-containing groups, for example of the type described above in relation to the group $L^1$ to yield heteroaliphatic, heterocycloaliphatic or polyheterocycloaliphatic hydrocarbon groups. In general, each hydrophilic hydrocarbon group forming the hydrophilic tail (3) may contain from one carbon atom to around two hundred carbon atoms.

Each hydrophilic hydrocarbon contains two or more atoms or groups capable of being solvated by water. Examples of such groups include oxygen atoms (—O—) or oxygen-containing groups. Oxygen atoms may form part of a heteroaliphatic, heterocycloaliphatic or polycycloheteroaliphatic group as just described. Oxygen-containing groups may be substituents present on the various hydrocarbons just mentioned and include for example hydroxyl, amide and alkoxy groups such as methoxy or ethoxy groups. In general the number of groups capable of being solvated by water in each hydrocarbon will range from two to around two hundred.

Particular examples of suitable hydrophilic hydrocarbons include polyols. Suitable polyols include naturally occurring polyols such as sugars and derivatives thereof, and synthetic polyols. Particular sugars include mono- and oligosaccharides. Sugar derivatives include glycosides in which a non-ionic aliphatic or heteroaliphatic group (for example of the type described herein) is joined to a sugar by a glycosidic linkage. Monosaccharides include for example open-chain or cyclic compounds containing three to eight, e.g. five or six, carbon atoms and at least two hydroxyl substituents. Oligosaccharides include for example at least two monosaccharides as just defined linked together by a glycosidic linkage. More than one type of monosaccharide may be present to yield a homo- or heterooligosaccharide.

Alternatively the hydrophilic hydrocarbon may be a polyether, for example a poly(alkylene oxide) and derivatives thereof, such as poly(ethylene oxide), poly(propylene oxide) or methoxy poly(ethylene oxide), a poly(oxyalkylated alcohol) or a poly(alkenylene alcohol) or poly(alkynylene alcohol) such as poly(vinyl alcohol). The hydrocarbons may in general be straight or branched. Where desired co-polymers of these hydrocarbons may be used.

Each hydrophilic hydrocarbon may be linked directly or indirectly to a hydrocarbon chain in the hydrophobic backbone (2). For indirect linkage a linker atom or group may be employed, for example an atom or group $L^3$ where $L^3$ is as defined above as for the linker atom or group $L^1$. Where the group $L^3$ is multivalent, for example when it is a branched alkylene chain containing more than one $X^1$ atom or group, more than one hydrophilic hydrocarbon may be attached to it.

A particularly useful group of compounds according to the invention has the formula (1a):

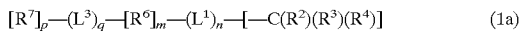

(1a)

wherein $R^2$, $R^3$, $R^4$, $L^1$, m and n are as defined for formula (1);

$R^6$ is a hydrocarbon chain;

$L^3$ is a linker atom or group;

$R^7$ is a hydrophilic hydrocarbon containing two or more atoms or groups capable of being solvated by water;

q is zero or an integer from one to six;

p is an integer from one to six;

and the salts, solvates and hydrates thereof, provided that each $R^7$ or $L^3$ group, when present, is attached to a group $R^6$ to achieve at least a ten atom spacing along $R^6$ between $R^7$ or $L^3$ and the group —$(L^1)_n$—[$C(R^2)(R^3)(R^4)$].

In the compounds of formula (1a) the hydrocarbon chain represented by $R^6$ may be a $C_{10}$ up to about a $C_{60}$ hydrocarbon chain as generally and more particularly described above in relation to the group $R^1$. The hydrophilic hydrocarbon $R^7$ may similarly be a hydrophilic hydrocarbon as described previously in relation to the group $R^1$. The group $L^3$ may be a linker atom or group as just defined.

The cationic head (1) in the lipids according to the invention will preferably be a group —$C(R^2)(R^3)(R^4)$ as described above in relation to the compounds of formulae (1) and (1a). In groups of this type, $R^2$ is preferably a hydrogen atom, and $R^3$ and $R^4$ is each preferably a group —$Sp^1[WSp^2]_bWSp^3$ or —$Sp^1[WSp^2]_bWH$ in which $Sp^1$, $Sp^2$ and $Sp^3$, which may be the same or different, is each a spacer group as defined above, W is a cationic centre as defined herein and b is zero or an integer from one to six.

In particular groups of this type, the cationic centre W is preferably a —NH— group. $Sp^1$, $Sp^2$ and $Sp^3$, which may be the same or different, is each preferably an optionally substituted $C_{1-6}$alkylene chain. b is preferably an integer from one to three.

Particularly useful cationic heads (1) in compounds of the invention include those of formula —$CH[Sp^1NHSp^2NH_2]_2$, —$CH[Sp^1NHSp^2NHSp^2NH_2]_2$ or —$CH[Sp^1NHSp^2NHSp^2NHCH_3]_2$ where each $Sp^1$ and $Sp^2$ group is the same or different and is an optionally substituted $C_{1-6}$alkylene chain, particularly wherein $Sp^1$ is —$CH_2$— and each $Sp^2$ is —$(CH_2)_3$— or —$(CH_2)_4$—.

In general in the lipids according to the invention the hydrophobic backbone (2) preferably comprises two or, especially one hydrocarbon chain as defined herein. Thus m in formulae (1) and (1a) is preferably an integer 2 or, especially, an integer 1. Each hydrocarbon chain, for example as represented by $R^1$ and $R^6$ in formulae (1) and (1a) respectively, is preferably linear and in particular is a linear, optionally substituted $C_{16-38}$alkylene chain. Optionally substituted $C_{18-24}$alkylene chains are particularly useful.

In general each hydrocarbon chain in the hydrophobic backbone (2) is preferably linked indirectly to the cationic head (1) through a linker atom or group. The linker atom or group may be for example an atom or group $L^1$ as defined herein and thus in the compounds of formulae (1) and (1a) for example n is preferably the integer 1.

Preferred linkers include those of formula —$X^1Alk^2$— or —$[X^1]_2Alk^1X^1Alk^2$— where $X^1$, $Alk^1$ and $Alk^2$ are as defined previously. Particularly useful linkers of these types are those wherein $Alk^2$ is a —$(CH_2)_4$—, —$(CH_2)_5$— or, especially, —$(CH_2)_6$— chain. $X^1$ in these linkers is preferably a —CONH— group. $Alk^1$ when present is preferably a —$CH_2$—CH< chain.

In another general preference each hydrocarbon chain in the hydrophobic backbone (2) has two, or especially one, hydrophilic hydrocarbon attached to it. Each hydrophilic hydrocarbon is preferably attached to the terminal carbon atom of the hydrocarbon chain distal to the chain carbon atom attached to the cationic head (1). Preferably the hydrophilic hydrocarbon and hydrocarbon chain are indirectly linked through a linker atom or group. Thus in one particular preference in compounds of formula (1a) q is the integer 1 and p is the integer 1 or 2.

In compounds of this type and in general the group $L^3$ may preferably be an atom or group —$X^1$—, —$X^1Alk^1X^1$— or [$X^1Alk^1$]$_2X^1Alk^2X^1$—. Particularly useful $L^3$ groups include —NHCO—, —CONH—, —CONH(CH$_2$)$_2$NHCO—, or —[CONH(CH$_2$)$_2$—]$_2$NCO(CH$_2$)$_2$CONH— groups.

In general, the hydrophilic hydrocarbon, for example as represented by $R^7$ in formula (1a) is preferably a synthetic polyol, a naturally occurring polyol such as mono- or disaccharide, or a poly(alkylene oxide) as defined herein. In particular $R^7$ may be a poly(alkylene oxide) or a derivative thereof, especially a poly(ethylene oxide).

Particularly useful lipids according to the invention are those described in the Examples hereinafter, especially in Sections H and I.

The lipids according to the invention may generally be prepared by coupling appropriately functionalised cationic heads (1), hydrophobic hydrocarbons (2) and hydrophilic hydrocarbons (3) in a predetermined order. Standard chemical coupling techniques may be employed utilising starting materials containing one or more reactive functional groups such as acids, thioacids, anhydrides, acid halides, esters, imides, aldehydes, ketones and amines. Illustrative reactions are described in detail in the Examples hereinafter for the preparation of a number of lipids according to the invention and these may be readily adapted using different starting materials to provide other compounds of the invention.

Thus in one general approach a homo- or heterobifunctional hydrocarbon chain may first be coupled to a hydrophilic hydrocarbon or cationic head and the resulting product coupled as necessary to the remaining component to provide the lipid of the invention.

The homo- or heterobifunctional hydrocarbon chain may be any hydrocarbon chain described herein containing two different reactive functional groups of the types just described. Particularly useful groups include acids and thioacids and reactive derivatives thereof, and amines. These can be used to participate in acylation or thioacylation reactions to couple the hydrocarbon chain to an amine or acid as appropriate in any suitable hydrophilic hydrocarbon and/or cationic head.

Acylation or thioacylation may be achieved using standard conditions for reactions of this type. Thus, for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a temperature from around ambient temperature to the reflux temperature, optionally in the presence of a base such as an amine, e.g. triethylamine, or a cyclic amine, such as 1,8-diazabicyclo[5.4.0] undec-7-ene pyridine, dimethylaminopyridine, or N-methylmorpholine.

Where an acid is used the acylation may additionally be performed in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole or a N-hydroxyimide such as N-hydroxysuccinimide. Alternatively, the acid may be reacted with a chloroformate, for example ethylchloroformate, prior to reaction with the amine.

In the heterobifunctional hydrocarbon chain one of the reactive functional groups may need to be in a protected form prior to any coupling reaction to avoid its unwanted participation in the reaction. Similarly other functional groups when present in the hydrocarbon chain, or the intermediates used to generate the hydrophilic hydrocarbon and/or the cationic head may need to be in a protected form before these reagents can be used. Conventional protecting groups may be used in accordance with standard practice [see, for example, Green, T. W. in "Protective Groups in Organic Synthesis", John Wiley & Sons, 1991 and the Examples hereinafter].

Suitable heterobifunctional hydrocarbon chains are either known, readily available materials or may be obtained by synthesis using conventional techniques for example as described in the Examples hereinafter. Thus generally a heterobifunctional hydrocarbon chain of any desired length may be synthesised in one or more reactions using appropriately functionalised shorter chains. Thus in one example a shorter chain aldehyde may be reacted with a shorter chain phosphonium salt to yield a longer chain olefin of the desired length. In this particular example the reaction may be carried out in the presence of a base, for example an organometallic base such as an organolithium compound, a hydride such as sodium or potassium hydride or an alkoxide such as a sodium alkoxide e.g. sodium methoxide. The reaction may be performed in a suitable solvent, for example a polar aprotic solvent such as an alkyl sulphoxide, e.g. dimethylsulphoxide at a low temperature, for example around 0° C. The starting aldehyde and phosphonium salt may be obtained from known starting alcohols and halides respectively using conventional procedures. Where desired, the olefin obtained above may be hydrogenated using hydrogen and a catalyst, for example Pearlman's catalyst, to yield the corresponding saturated hydrocarbon chain.

Where it is desired to obtain hydrocarbon chains containing one or more heteroatoms or heteroatom-containing groups these may be synthesised from smaller chains containing functional groups which can be chemically coupled, for example by acylation or thioacylation as generally described above.

Suitable functionalised hydrophilic hydrocarbons or cationic heads for coupling to the heterobifunctional hydrocarbon chain are either readily available or may be synthesised from known materials by conventional methods for example as described in the Examples hereinafter.

The advantageous properties of the lipids according to the invention may be demonstrated using the small scale tests described hereinafter in the Examples. In these the lipids can be shown to efficiently compact any bioactive substance, and to self-assemble with the substance in aqueous solution to yield stable complexes which remain associated over wide pH and ionic strength ranges and which will efficiently deliver the substance to eucaryotic cells.

The lipids can thus be expected to be of use for the delivery of bioactive substances to cells, particularly eucaryotic cells, in vitro and especially in vivo. Particular general uses to which the lipids may be put thus include for the delivery of bioactive substances to cells in culture, and in human medicine for the delivery of therapeutic or diagnostic agents, or agents which can generate a host immune response for vaccine or other immuno-modulatory purposes. The lipids are particularly well suited for delivering bioactive polyanions, especially nucleic acids, and are of particular use to modify a host's genotype or its expression.

Thus, in another aspect of the invention we provide a lipid complex characterised in that it comprises a bipolar lipid comprising a cationic head (1) a hydrophobic backbone (2) and a hydrophilic tail (3) in which:

(A) the cationic head comprises two or more cationic centres, each centre being covalently linked to one or more others by one or more carbon containing spacer groups;

(B) the hydrophobic backbone comprises one or more hydrocarbon chains; and (C) the hydrophilic tail comprises one or more hydrophilic hydrocarbons each containing two or more atoms or groups capable of being solvated by water;

each of said components (1) to (3) being covalently linked head (1) to backbone (2) to tail (3) and arranged such that at least one hydrocarbon chain in the hydrophobic backbone (2) is covalently linked to a carbon atom of a spacer group in the cationic head (1) and each hydrophilic hydrocarbon in the hydrophilic tail (3) is covalently linked to a chain in the backbone (2) to achieve at least a carbon atom spacing along the chain between the tail (3) and the head (1), in association with one or more bioactive substances.

In the complexes according to the invention, each bioactive substance may be for example a pharmacologically active agent, including an endosomolytic agent, a diagnostic agent or any agent able to modify the genotype and/or phenotype of a cell.

Particular examples of such substances include bioactive proteins, peptides, polysaccharides, nucleic acids including synthetic polynucleotides, oligonucleotides and derivatives thereof, lipids, glycolipids, lipoproteins, lipopolysaccharides and viral, bacterial, protozoal, cellular or tissue fractions.

Where desired the complexes according to the invention may contain two or more different bipolar lipids of the invention and such lipid mixtures form a further particular aspect of the invention. Especially useful mixtures include those containing two or more bipolar lipids of the invention which differ from each other in the nature of the hydrophilic tail present in each. The proportion of each lipid in complexes of this type may be manipulated to obtain complexes with different physio-chemical properties, for example overall surface charge and/or particle size, tailored to meet the intended use of the complex. Thus for example in one advantageous lipid complex containing two or more bipolar lipids, one of the lipids has a hydrophilic tail formed by a poly(alkyene oxide) or a derivative thereof as defined herein, while each of the others has a hydrophilic tail formed by a synthetic or naturally occurring polyol as described previously. The proportion of the first poly(alkylene oxide)-containing lipid may be varied in such complexes so that the mole ratio of first lipid to second and other lipids is from 1:10000 to 1:1, advantageously from around 1:1000 to around 1:20, especially around 1:10. Complexes of these types, particularly where the poly(alkylene oxide) is poly(ethylene oxide), may be obtained which advantageously have zero surface charge and do not aggregate when left in solution and which additionally are able to compact a bioactive substance to give small particles of 150 nm and below, particularly 100 nm and below, especially around 80–85 nm.

The lipids according to the invention are particularly suited for delivering polyanions to cells and preferred lipid complexes of the invention thus include lipid-polyanion complexes in which the polyanion may be any of the above-mentioned bioactive substances possessing a net negative charge. Particular polyanions include nucleic acids, for example single or double stranded, circular or supercoiled DNA or RNA and derivatives thereof. Where desired the DNA may be part of a structure such as a plasmid.

The lipid complexes will in general comprise a lipid according to the invention and a bioactive substance in a weight ratio of around 0.1:1 to around 100:1, for example around 1:1 to around 50:1. The complexes may be formed as liquids, by initially mixing one or more bipolar lipids according to the invention, and a bioactive substance together advantageously in an aqueous solvent using conventional procedures. Where desired the solvent may be removed, for example by lyophilisation, to obtain a solid lipid complex.

The lipid complexes according to the invention may be formulated with other materials such as one one or more other lipids or other pharmaceutically acceptable carriers, excipients or diluents and the invention extends to such compositions. In this aspect of the invention the "other" lipid may be for example selected from any known neutral and/or cationic lipid, for example selected from those described herein in the introduction to the invention (see page 2) and also especially including DOPE and other cholesterol derivatives such as cholesterol hemisuccinate. Particularly useful formulations of this type are those wherein the bipolar lipid of the invention has a poly(alkylene oxide) tail, especially a poly(ethylene oxide) tail.

Particular compositions include liposome formulations, prepared using conventional liposome technology. Otherwise, the compositions may take any other supermolecular form suitable for oral, buccal, parenteral, nasal, topical or rectal administration, or a form suitable for administration by inhalation or insufflation.

For oral administration, the compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The complexes of the invention may be formulated for parenteral administration by injection, including bolus injection or infusion or particle mediated injection. Formulations for injection may be presented in unit dosage form, e.g. in glass ampoule or multi dose containers, e.g. glass vials or a device containing a compressed gas such as helium for particle mediated administration. The compositions for bolus injection or infusion may take such forms as suspensions, solutions or emulsions in oily or aqueous vehicles, and may contain formulatory agents such as suspending, stabilising, preserving and/or dispersing agents. Alternatively, the complex may be in powder form for constitution with a suitable vehicle, e.g. sterile pyrogen-free water, before use. For particle mediated administration the complex may be coated on particles such as microscopic gold particles.

In addition to the formulations described above, the complexes may also be formulated as a depot preparation.

Such long acting formulations may be administered by implantation or by intramuscular injection.

For nasal administration or administration by inhalation, the complexes may be conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The complexes may, if desired, be presented in a pack or dispenser device which may contain one or more unit dosage forms containing the active ingredient. The pack or dispensing device may be accompanied by instructions for administration.

The quantity of lipid complex required for any particular application will to a large extent depend on the nature of the bioactive substance being delivered. Another important factor will include whether the lipid complex is intended for in vitro or in vivo use. If the latter the route of administration and particular formulation chosen as well as factors such as the age and condition of the subject will govern the quantity of lipid complex used. In general however up to around 50 mg of lipid complex can be used for every kilogram of body weight.

The following Examples illustrate the invention. In these, the preparation of the lipids of the invention and the intermediates thereto has been divided into sections for ease of understanding as follows:

INTERMEDIATES

Section

B. Polyamine Intermediates
C. Disugar Intermediates
D. Long Chain Amino Acid Syntheses
E. Lipid Polyamines
F. Glycolipid Syntheses
G. Two Lipid Chain Syntheses

LIPIDS OF THE INVENTION

Section

H. Carbohydrate Lipid Tetramines and Hexamines
I. PEG Lipids

Compounds are referred to throughout the text by their Section numbering B1, B2, B3 . . . etc. The following abbreviations are also used:

BOC—t-butoxycarbonyl;
DCM—dichloromethane;
EDC—1-(3-dimethylaminopropyl)-3-ethylcarbodiimide;
TFA—trifluoroacetic acid;
LDA—lithium diisopropylamide;
DBU—1,8-diazabicyclo[5.4.0]un-dec-7ene;
PDC—pyridinium dichromate;
Me—CH$_3$; Ph—phenyl;
tlc—thin layer chromatography;
THF—tetrahydrofuran;
DMF—dimethylformamide;
DMSO—dimethylsulphoxide;
DMAP—dimethylaminopyridine;
Ac—acetate;
Bn—benzyl.

B. POLYAMINE INTERMEDIATES

This section contains the syntheses of:

BOC Protected Tetramine (B8) N-(t-Butyloxycarbonyl)-N-(t-butyloxycarbonylaminobutyl)-2-[t-butyloxycarbonylaminobutyl(t-butyloxycarbonyl)-aminomethyl]octane-1,8-diamine

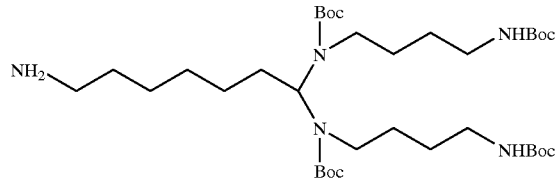

BOC Protected Hexamine (B16) 11-Aminohexyl-4,9,13,18-tetrakis(t-butyloxycarbonyl)-4,9,13,18-tetraazaeicosane-1,21-diamine

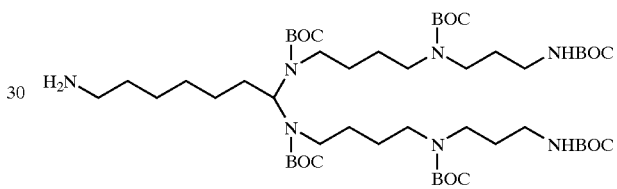

BOC Protected Dimethylated Hexamine (B21) N-[Methyl(t-butyloxycarbonyl)aminopropyl(t-butyloxycarbonyl)aminobutyl(t-butyloxycarbonyl)]-2-[methyl(t-butyloxycarbonyl)aminopropyl(t-butyloxycarbonyl)-aminobutyl(t-butyloxycarbonyl)aminomethyl]-1,8-octanediamine

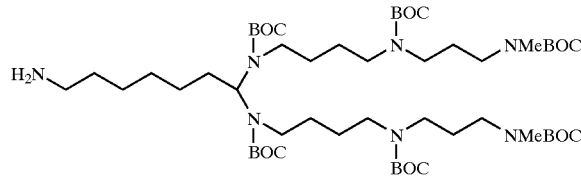

BOC Protected Tetramine (B1) 1-Benzyloxy-6-chlorohexane

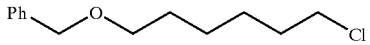

To a stirred solution of 6-chloro-1-hexanol (15.0 g, 0.110 mol) and benzyl bromide (18.8 g, 0.110 mol) in dry THF (200 ml) at room temperature under argon was slowly added (over 30 min.) sodium hydride powder (2.899 g, 0.121 mol). The solution was left overnight and the solids filtered off. The solvent was removed under reduced pressure, the residues taken up into dichloromethane (100 ml) and washed (2×20 ml water). The solution was dried over MgSO$_4$ and the solvent removed to yield an orange oil which was subsequently distilled (160° C., 0.5 mBar) to yield the title compound (17.5 g, 70%) as a colourless oil. C$_{13}$H$_{19}$OCl requires 226. Found DCl: MNH$_4^+$, 244. δH (CDCl$_3$) 1.49 (4H, m, (CH$_2$)$_2$(CH$_2$)$_2$Cl), 1.70 (2H, p, CH$_2$CH$_2$O), 1.83 (2H, t, CH$_2$CH$_2$Cl), 3.54, 3.56 (4H, 2×t, CH$_2$CH$_2$O, CH$_2$Cl), 4.56 (2H, s, CH$_2$Ph), 7.40 (5H, m, Ph). δC (CDCl$_3$) 25.3 (1C, CH$_2$(CH$_2$)$_2$Cl), 26.4 (1C, CH$_2$(CH$_2$)$_3$Cl), 29.3 (1C, CH$_2$(CH$_2$)$_2$O), 32.3 (1C, CH$_2$CH$_2$Cl), 44.8 (1C, CH$_2$Cl), 69.9, 72.6 (2C, CH$_2$O), 127.2 (1C, CH(CH$_2$)$_2$C), 127.3 (2C, CHC), 128.1 (2C, CHCHC), 138.4 (1C, CCH$_2$O).

(B2) Diethyl 2-(Benzyloxyhexyl)malonate

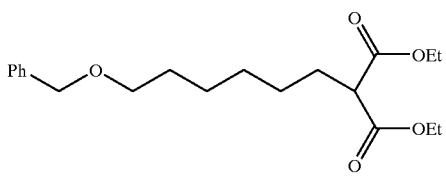

To sodium metal (1.32 g, 0.0573 mol) dissolved in dry ethanol (150 ml) under argon at room temperature was added diethyl malonate (14.13 g, 0.088 mol) over a period of 10 minutes and the solution left for 2 hours. B1 (10.0 g, 0.044 mol) was then added dropwise over 2 hours and this solution heated at reflux overnight. Excess salts were quenched by the addition of 50 ml of water and the total solvent volume reduced to 50–100 ml. Diethyl ether (100 ml) and water (50 ml) were added and the aqueous layer extracted 3 times with diethyl ether. The organic fractions were combined, dried (K$_2$CO$_3$), and the solvent removed to yield the crude product as a yellow oil. Distillation of the oil (0.5 mBar, 220° C.) gave the title compound (10.52 9, 68%) as a colourless viscous oil. δH (CDCl$_3$) 1.32 (6H, t, Me), 1.43 (6H, br s, (CH$_2$)$_3$CH$_2$CH), 1.69 (2H, p, CH$_2$CH$_2$O), 1.99 (2H, q, CH$_2$CH), 3.39 (1H, t, CH), 3.53 (2H, t, CH$_2$OCH$_2$Ph), 4.25, 4.28 (4H, 2×q, OCH$_2$Me), 4.57 (2H, s, CH$_2$Ph), 7.3–7.4 (5H, m, Ph). δC (CDCl$_3$) 13.9 (2C, Me), 25.7 (1C, CH$_2$(CH$_2$)$_2$CH), 27.1 (1C, CH$_2$(CH$_2$)$_2$O), 28.5 (1C, CH$_2$CH$_2$CH), 28.9 (1C, CH$_2$CH$_2$O), 29.5 (1C, CH$_2$CH), 51.8 (CHCO$_2$Et), 61.0 (2C, OCH$_2$Me), 70.1, 72.7 (2C, CH$_2$OCH$_2$), 127.3 (1C, CH(CH)$_2$C), 127.4 (2C, CHC), 128.1 (2C, CHCHC), 138.5 (1C, CCH$_2$O), 169.3 (2C, CO$_2$).

(B3) N,N'-bis(Aminobutyl)-2-(benzyloxyhexyl) malonamide

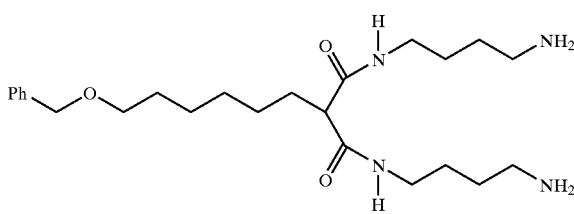

To a large excess of 1,4-diaminobutane (85 g, 0.964 mol) at 90° C. under argon was slowly added (over 2 hours) B2 (10.50 g, 0.030 mol). The solution was heated at 90° C. overnight and the excess diamine distilled off under reduced pressure (0.1 mBar, 28° C.) to quantitatively yield the title compound as a pale yellow low melting point solid. C$_{24}$H$_{42}$N$_4$O$_3$ requires 434. Found DCl: M$^+$+1 435. I.R. 1664 cm$^{-1}$ (CO$_2$). δH (CDCl$_3$) 1.15–1.40 (10H, br m, (CH$_2$)$_3$CH$_2$CH, NH$_2$), 1.40–1.60 (10H, br m, (CH$_2$)$_2$CH$_2$NH$_2$, CH$_2$CH$_2$O), 1.76 (2H, q, CH$_2$CH), 2.63 (4H, t, CH$_2$NH$_2$), 2.93 (2H, t, CH$_2$CH), 3.16 (4H, q, CH$_2$NH), 3.37 (2H, t, CH$_2$OCH$_2$Ph), 4.42 (2H, s, CH$_2$Ph), 7.26 (5H, m, Ph), 7.61 (2H, t, CONH). δC (CDCl$_3$) 25.7 (1C, CH$_2$(CH$_2$)$_2$CH), 26.6 (2C, CH$_2$CH$_2$NH$_2$), 28.8, 29.4 (2C, CH$_2$CH$_2$CH, CH$_2$CH$_2$O), 30.6 (2C, CH$_2$CH$_2$NH), 32.7 (1C, CH$_2$CH), 39.0 (2C, CH$_2$NHCO), 41.4 (2C, CH$_2$NH$_2$), 54.7 (1C, CHCO), 70.1, 72.6 (2C, CH$_2$OCH$_2$), 127.2 (1C, CH(CH)$_2$C), 127.3 (2C, CHC), 128.0 (2C, CHCHC), 138.5 (1C, CCH$_2$O), 171.0 (2C, CONH).

(B4) N,N'-bis(Aminobutyl)-2-benzyloxyhexyl-1,3-propanediamine

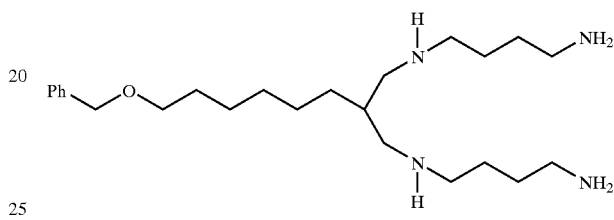

To B3 (0.430 g, 0.989 mmol) under argon was added an excess (25 ml) of 1.0 M BH$_3$-THF, and the solution heated at 85° C. overnight. Excess borane was slowly quenched with methanol (10 ml) and the solvents removed under reduced pressure. The residues were taken up into 0.1 M HCl (100 ml), heated at 60° C. for 1 hour, and the solvent removed under reduced pressure. The residues were entrained with methanol (4×20 ml), and the tetraamine hydrochloride salt taken up into water (30 ml). The solution was basified to pH~14 with sodium hydroxide and exhaustively extracted with dichloromethane. The organic fractions were combined, dried (K$_2$CO$_3$), and the solvent removed to yield the title compound (0.352 g, 88%) as a pale yellow oil/gum. C$_{24}$H$_{46}$N$_4$O requires 406. Found DCl: M$^+$+1, 407. δH (CDCl$_3$) 1.0–1.6 (25H, br m, CH(CH$_2$)$_5$, NH, NH$_2$, (CH$_2$)$_2$CH$_2$NH$_2$), 2.2–2.6 (12H, br m, CH$_2$N), 3.28 (2H, t, CH$_2$OCH$_2$Ph), 4.31 (2H, s, CH$_2$Ph), 7.14 (5H, m, Ph). δC (CDCl$_3$) 25.3 (1C, CH$_2$CH$_2$CH), 26.2 (1C, CH$_2$(CH$_2$)$_2$CH), 26.6 (2C, CH$_2$CH$_2$NH$_2$), 28.9 (2C, CH$_2$(CH$_2$)$_2$CH$_2$CH), 30.7 (3C, CH$_2$CH$_2$NH, CH$_2$CH$_2$O), 37.6 (1C, CH), 41.2 (2C, CH$_2$NH$_2$), 49.3 (2C, (CH$_2$)$_3$CH$_2$NH), 53.5 (2C, CHCH$_2$NH), 69.5, 71.9 (2C, CH$_2$OCH$_2$), 126.5 (1C, CH(CH)$_2$C), 126.6 (2C, CHC), 127.4 (2C, CHCHC), 137.8 (1C, CCH$_2$O).

(B5) N,N'-bis(t-Butyloxycarbonyl)-N-[2-t-butyloxycarbonylaminobutyl(t-butyloxycarbonyl)aminomethyl]benzyloxyoctyl-1,4-diaminobutane.

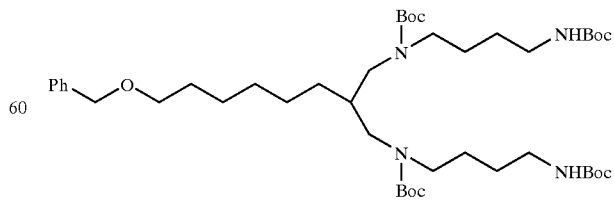

B4 (10 g, 24.6 mmol) was dissolved in aqueous sodium hydroxide (100 ml, 2M). To this solution was added t-butyldicarbonate (27 g, 123.3 mmol) portionwise with stirring at room temperature. The reaction was stirred overnight, water added and the aqueous phase extracted with ethyl acetate. The combined organic extracts were washed with water, brine, dried & evaporated to give the crude product. Chromatography (silica—20% ethyl acetate in hexane) gave the title compound as a glass (11 g, 55%). $C_{44}H_{78}N_4O_9$ requires 806. Found DCl: $M^++1$, 807.8. $\delta H$ (CDCl$_3$) 7.74 (5H, m, ArH), 4.49 (2H, s, CH$_2$Ar), 3.45 (2H, t, CH$_2$OCH$_2$Ph), 2.9–3.3 (12H, t, CH$_2$N), 1.95 (1H, brm, CH$_2$CH(CH$_2$)$_2$), 1.2–1.7 (52H, m, CH$_2$).

(B6) 8-[t-Butyloxycarbonylaminobutyl(t-butyloxycarbonyl)amino]-7-[t-butyloxycarbonylaminobutyl(t-butyloxycarbonyl)aminomethyl]octanol

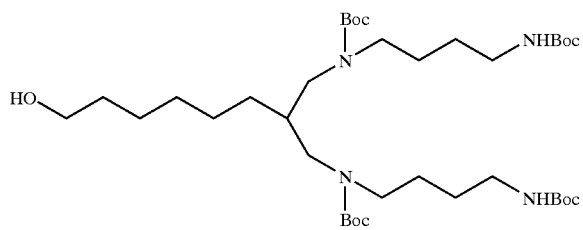

To B5 (11 g) in methanol (70 ml) under argon was added palladium on carbon catalyst (1 g). The stirred suspension was put under a hydrogen atmosphere for two days at atmospheric pressure and room temperature. The mixture was filtered through Celite which was washed with dichloromethane. Evaporation yielded the title compound (9.67 g, 87%) which was used for the next stage without purification.

(B7) 8-[t-Butyloxycarbonylaminobutyl(t-butyloxycarbonyl)amino]-7-[t-butyloxycarbonylaminobutyl(t-butyloxycarbonyl)aminomethyl]octyl Methanesulphonate

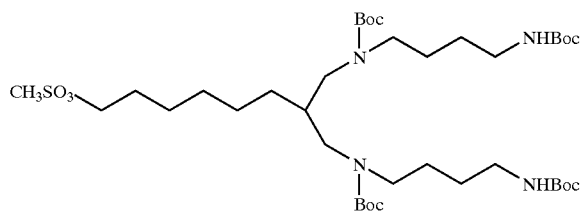

Methanesulphonyl chloride (1.25 ml, 16.21 mmol) was added to a stirred solution of B6 (9.67 g, 13.5 mmol) in dry dichloromethane (100 ml) containing triethylamine (2.82 ml, 20.26 mmol) at 0° C. The flask was stirred at 0° C. for 1 hr, then overnight at room temperature. The solvent was removed and the residue chromatographed (silica—50% ethyl acetate in hexane) to yield the title compound (8.5 g, 79%. $C_{38}H_{74}N_4O_{11}S$ requires 794. Found DCl: $M^++1$, 795.6. $\delta H$ (CDCl$_3$) 3.45 (2H, t, CH$_2$O), 2.9–3.3 (12H, m, CH$_2$N), 2.99 (3H, s, MeS), 1.95 (1H, brm, CH$_2$CH(CH$_2$)$_2$), 1.2–1.8 (50H, m, CH$_2$).

(B8) N-(t-Butyloxycarbonyl)-N-(t-butyloxycarbonylaminobutyl)-2-[t-butyloxycarbonylaminobutyl(t-butyloxycarbonyl)aminomethyl]octane-1,8-diamine

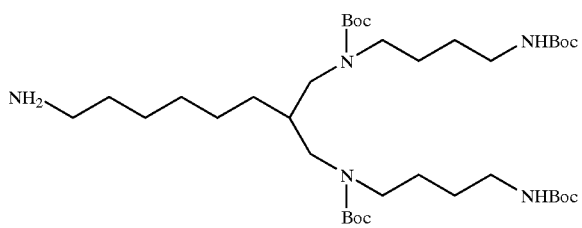

Sodium azide (2.05 g, 31.6 mmol) was added to a stirred solution of B7 (8.36 g, 10.53 mmol) in dry DMF (35 ml) at room temperature. The reaction was stirred for 48 hr and water added. The aqueous solution was extracted with ethyl acetate. The organic phase was washed with brine, dried (MgSO$_4$) and evaporated to dryness. The product was chromatographed (silica—up to 50% ethyl acetate in hexane) and the resulting azide was dissolved in methanol (100 ml) under argon and palladium on charcoal added. The atmosphere was changed to hydrogen and the reaction stirred overnight. The catalyst was filtered off and the product chromatographed (silica—up to 20% methanol in dichloromethane containing triethylamine to yield the title compound (4.5 g). $C_{37}H_{73}N_5O_8$ requires 715.55. Found DCl: $M^++1$, 716.7. $\delta H$ (CDCl$_3$) 4.71 (2H, br, NHBoc), 2.95–3.3 (12H, m, CH$_2$N), 2.85 (2H, br, NH$_2$), 2.75 (2H, t, CH$_2$NH$_2$), 1.95 (1H, brm, CH$_2$CH(CH$_2$)$_2$), 1.2–1.7 (54H, m, CH$_2$).

BOC Protected Hexamine Synthesis (B9) N,N'-bis(p-Methoxyphenylsulphonyl)-N-{2-[p-methoxyphenylsulphonylaminobutyl(p-methoxyphenylsulphonyl)aminomethyl]benzyloxyoctyl}-1,4-butanediamine

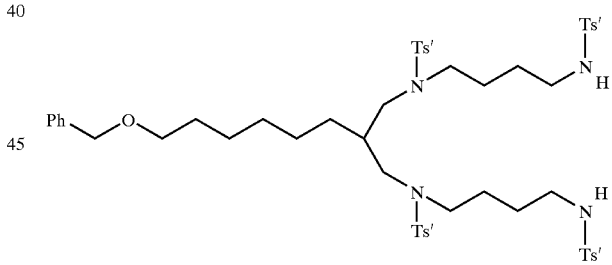

To B4 (301 mg, 0.740 mmol) and triethylamine (749 mg, 7.40 mmol) in dry THF (30 ml) under argon at −50° C. was slowly added p-methoxybenzenesulphonyl chloride (627 mg, 3.03 mmol). The solution was allowed to slowly warm to room temperature and left overnight. The product (tlc r.f. 0.7, 2% methanol in dichloromethane) was purified by gradient alumina column chromatography (0–2% methanol in dichloromethane) to yield the title compound (610 mg, 76%) as a colourless gum/solid. $\delta H$ (CDCl$_3$) 1.15–1.70 (18H, br m, (CH$_2$)$_5$CH$_2$O, (CH$_2$)$_2$CH$_2$NH), 2.00 (1H, t, CH), 2.75–3.15 (12H, br m, CH$_2$N), 3.45 (2H, t, CH$_2$OCH$_2$Ph), 3.81, 3.84 (12H, 2×s, OMe), 4.47 (2H, s, CH$_2$Ph), 5.25 (2H, t, NH), 6.92, 6.97 (8H, 2×d, CHCSO$_2$), 7.29 (5H, m, Ph), 7.69, 7.75 (8H, 2×d, CHCOMe). $\delta C$ (CDCl$_3$) 25.2–26.2 (5C, CH(CH$_2$)$_5$), 29.2, 29.3 (4C, (CH$_2$)$_2$CH$_2$NH), 36.0 (1C, CH), 42.1 (2C, CH$_2$NH), 48.8 (2C, (CH$_2$)$_3$CH$_2$NH), 51.2 (2C, CHCH$_2$N), 55.2 (4C, OMe), 70.0, 72.3 (2C, CH$_2$OCH$_2$), 113.8, 114.0 (8C, CHCSO$_2$), 127.0, 127.2, 127.9 (5C, Ph), 128.7, 128.9 (8C, CHCOMe), 129.8, 131.0 (4C, CSO$_2$), 138.2 (1C, CCH$_2$O), 162.3, 162.5 (4C, COMe).

(B10) 11-Benzyloxyhexyl-4,9,13,18-tetrakis(p-toluenesulphonyl)-4,9,13,18-tetraazaeicosane-1,21-dinitrile

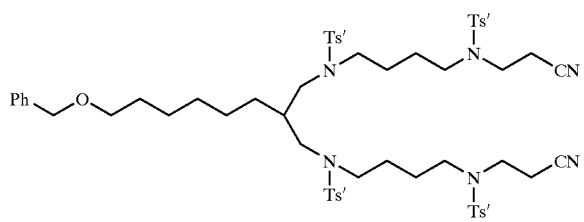

To B9 (588 mg, 0.541 mmol) and mesh potassium carbonate (523 mg, 3.784 mmol) in 20 ml of dry DMF under argon was added freshly distilled acrylonitrile (95 mg, 1.787 mmol) and the reaction left stirring at room temperature for 3–4 days. T.l.c (alumina 2% MeOH in CH$_2$Cl$_2$) indicated the presence of two compounds r.f 0.9 and 0.8, later shown to be the desired di-nitrile and the mono-nitrile respectively. Gradient alumina column chromatography (as for B9) yielded the title compound as a colourless gum/solid in 52% (337 mg) yield. C$_{58}$H$_{76}$N$_6$O$_{13}$S$_4$ requires 1193 Found ES+: MNa$^+$ 1216. δH (CDCl$_3$) 1.15–1.40 (8H, br m, CH(CH$_2$)$_4$), 1.40–1.70 (10H, br, (CH$_2$)$_2$CH$_2$N, CH$_2$CH$_2$O), 2.02 (1H, t, CH), 2.63 (4H, t, CH$_2$CN), 2.80–3.16 (12H, br m, CH$_2$N), 3.24 (4H, t, CNCH$_2$CH$_2$N), 3.47 (2H, t, CH$_2$OCH$_2$Ph), 3.81, 3.82 (12H, 2×s, OMe), 4.46 (2H, s, CH$_2$Ph), 6.95, 6.96 (8H, 2×d, CHCSO$_2$), 7.29 (5H, m, Ph), 7.69, 7.70 (8H, 2×d, CHCOMe). δC (CDCl$_3$) 18.9 (2C, CH$_2$CN), 25.3–28.3 (5C, CH(CH$_2$)$_5$), 29.6, 29.7 (4C, (CH$_2$)$_2$H$_2$N), 36.4 (1C, CH), 44.5 (2C, CNCH$_2$CH$_2$), 48.7 (2C, CH$_2$N(CH$_2$)$_2$CN), 49.0 (2C, CH$_2$NCH$_2$CH), 51.5 (2C, CHCH$_2$N), 55.5 (4C, OMe), 70.3, 72.7 (2C, CH$_2$OCH$_2$), 114.2, 114.4 (8C, CHCSO$_2$), 117.7 (2C, CN), 127.3, 127.5, 128.2 (5C, Ph), 129.2 (8C, CHCOMe), 129.5, 130.2 (4C, CSO$_2$), 138.5 (1C, CCH$_2$O), 162.7, 163.0 (4C, COMe).

(B11) 11H-Benzyloxyhexyl-4,9,13,18-tetrakis(p-toluenesulphonyl)-4,9,13,18-tetraazaeicosane-1,21-diamine

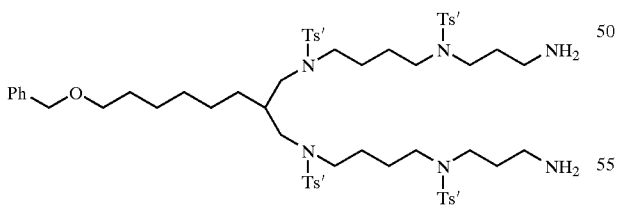

To B10 (337 mg, 0.282 mmol) under argon was added an excess (30 ml) of 1.0 M BH$_3$-THF, and the solution heated at 85° C. overnight. Excess borane was slowly quenched with methanol (10 ml) and the solvents removed under reduced pressure. The residues were taken up into 0.1 M HCl (100 ml), heated at 60° C. for 1 hour, and the solvent removed under reduced pressure. The residues were entrained with methanol (4×20 ml), and the hydrochloride salt taken up into water (30 ml). The solution was basified to pH>14 with sodium hydroxide and exhaustively extracted with dichloromethane. The organic fractions were combined, dried (K$_2$CO$_3$), and the solvent removed to yield the title compound (285 mg, 84%) as a colourless gum/solid. C$_{58}$H$_{84}$N$_6$O$_{13}$S$_4$ requires 1201. Found ES+: MH$^+$ 1202. δH (CDCl$_3$) 1.2–1.7 (26H, br m, CH(CH$_2$)$_5$, CH$_2$(CH$_2$)$_2$CH$_2$N, CH$_2$CH$_2$NH$_2$), 2.20 (1H, t, CH), 2.70 (4H, t, CH$_2$NH$_2$), 2.85–3.35 (16H, br m, CH$_2$N), 3.50 (2H, t, CH$_2$OCH$_2$Ph), 3.86, 3.88 (12H, 2×s, OMe), 4.52 (2H, s, CH$_2$Ph), 6.99, 7.02 (8H, 2×d, CHCSO$_2$), 7.75, 7.76 (8H, 2×d, CHCOMe). δC (CDCl$_3$) 25.1–26.2 (5C, CH(CH$_2$)$_5$), 29.4, 29.6 (4C, CH$_2$(CH$_2$)$_2$CH$_2$N), 32.0 (2C, CH$_2$CH$_2$NH$_2$), 36.2 (1C, CH), 38.8 (2C, CH$_2$NH$_2$), 45.9 (2C, CH$_2$(CH$_2$)$_2$NH$_2$), 47.7 (2C, CH$_2$N(CH$_2$)$_3$NH$_2$), 48.7 (2C, CHCH$_2$NCH$_2$), 51.1 (2C, CHCH$_2$N), 55.3 (4C, OMe), 70.1, 72.5 (2C, CH$_2$OCH$_2$), 113.9, 114.0 (8C, CHCSO$_2$), 127.1, 127.3, 128.0 (5C, Ph), 128.8, 129.0 (8C, CHCOMe), 130.2, 130.7 (4C, CSO$_2$), 138.5 (1C, CCH$_2$O), 162.4, 162.5 (4C, COMe).

(B12) 8-(Aminopropylaminobutylamino)-7-(aminopropylaminobutylaminomethyl)octanol

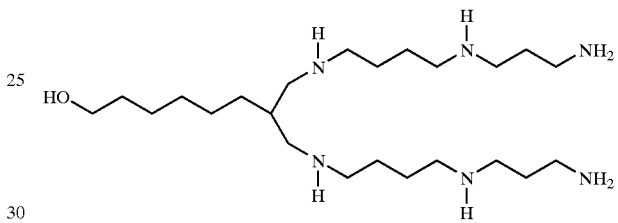

To B11 (743 mg, 0.618 mmol) in THF (30 ml) and ethanol (2 ml) at −78° C. was condensed liquid ammonia (75 ml). To this was then added 300 mg of lithium metal (turned blue), and the solution stirred for 2 hours. The solution was then allowed to slowly warm to room temperature overnight, boiling off the ammonia as it did. Ethanol (2 ml) followed by water (70 ml) were added to the now yellow solution and the organic solvents removed under reduced pressure. The pH of the remaining aqueous solution was lowered to 2 (concentrated HCl), washed (4×20 ml) with diethyl ether, and basified to pH 10–12 (NaOH). The solvent was removed to yield the title compound in the presence of a large excess of salts. This material was used for the next step without purification (B13) 8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)aminobutyl(t-butyloxycarbonyl)aminomethyl]octanol

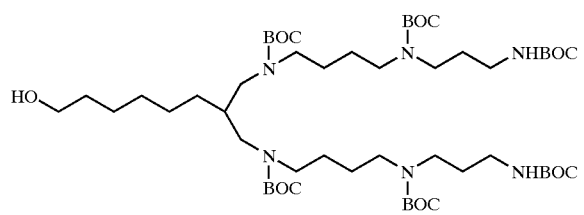

To B12 dissolved in methanol (5 ml) was added 10 equivalents of ditertbutyl dicarbonate (1.349 g, 6.183 mmol) and the solution left overnight. The solvent was removed, the residues taken up into water (20 ml), and extracted with dichloromethane (5×30 ml). The organic fractions were combined, dried (K₂CO₃), and the solvent removed to yield a pale yellow gum. Purification required alumina column chromatography (0–3% methanol in dichloromethane) to yield the desired BOC protected title compound (alumina tlc r.f. 0.7, 5% methanol in dichloromethane) as a colourless gum (281 mg, 44%). C₅₃H₁₀₂N₆O₁₃ requires 1031. Found ES+: MH⁺ 1032, ES–: M⁻ 1031, MCl⁻ 1066. δH (CDCl₃) 1.1–2.0 (77H, br m, C(Me)₃, CH(CH₂)₅, CH₂(CH₂)₂CH₂N, CH₂CH₂NH), 2.7–3.4 (20H, br, CH₂N), 3.53 (2H, t, CH₂O), 5.26, 5.45 (2H, br, NHBOC). δC (CDCl₃) partial 43.5, 46.5, 48.9 (10C, CH₂N), 62.1 (1C, CH₂OH), 78.5, 79.1 (6C, C(Me)₃), 155.3, 155.7 (6C, CO).

(B14) 8-[t-Butyloxycarbonylaminopropyl(t-butyloxycarbonyl)aminobutyl(t-butyloxycarbonyl) amino]-7-[t-butyloxycarbonylaminopropyl(t-butyloxycarbonyl)aminobutyl(t-butyloxycarbonyl) aminomethyl]octyl Methanesulphonate

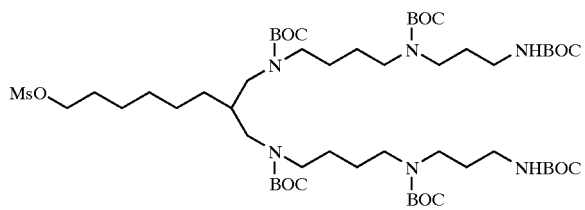

To B13 (555 mg, 0.538 mmol) and triethylamine (163 mg, 1.614 mmol) in dry dichloromethane (20 ml) at –20° C. under argon was added mesyl chloride (124 mg, 1.076 mmol) dropwise in dichloromethane (5 ml) over a period of 30 minutes. The solution was allowed to warm to room temperature and left overnight. The solvent was removed to quantitatively yield the title compound, tlc r.f. 0.35 (5% methanol in dichloromethane on alumina). δH (CDCl₃) 1.1–2.0 (77H, br m, C(Me)₃, CH(CH₂)₅, CH₂(CH₂)₂CH₂N, CH₂CH₂NH), 2.7–3.4 (20H, br, CH₂N), 3.01 (3H, s, MeS), 4.18 (2H, t, CH₂O), 5.26, 5.45 (2H, br, NHBOC). δC (CDCl₃) partial 38.4 (MeS), 43.5, 46.5, 48.9 (10C, CH₂N), 69.3 (C, CH₂O), 78.5, 79.1 (6C, C(Me)₃), 155.3, 155.7 (6C, CO).

(B15) 11-Azidohexyl-N,N', 4,9,13,18-hexa(t-butyloxycarbonyl)-4,9,13,18-tetraaza-1,21-eicosanediamine

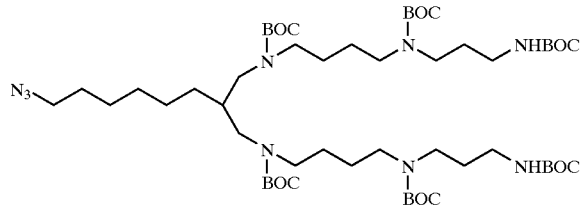

To the crude mesylate B14 in dry DMF (15 ml) under argon was added excess sodium azide (600 mg) and the solution/suspension stirred overnight. The volume was reduced to approximately 5 ml and added to 70 ml of water. This aqueous phase was extracted with ethyl acetate (10×30 ml) and the organics combined, dried (MgSO₄) and the solvent removed to yield the title compound as a pale yellow gum (570 mg, 100%). I.R. 2095 cm⁻¹ (N₃). C₅₃H₁₀₁N₉O₁₂ requires 1056. Found ES+: MH⁺ 1057, MNa⁺ 1079. δH (CDCl₃) 1.1–2.0 (77H, br m, C(Me)₃, CH(CH₂)₅, CH₂(CH₂)₂ CH₂N, CH₂CH₂NH), 2.7–3.4 (20H, br, CH₂N), 3.31 (2H, t, CH₂N₃), 5.26, 5.45 (2H, br, NHBOC). δC (CDCl₃) partial 43.5, 46.5, 48.9 (10C, CH₂N), 51.3 (1C, CH₂N₃), 78.5, 79.1 (6C, C(Me)₃), 155.3, 155.7 (6C, CO).

(B16) 11-Aminohexyl-4,9,13,18-tetrakis(t-butyloxycarbonyl)-4,9,13,18-tetraazaeicosane-1,21-diamine

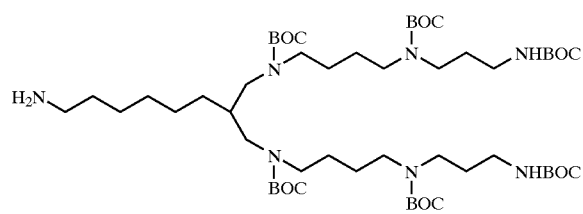

To B15 (134 mg, 0.127 mmol) in methanol (15 ml) was added 10% Pd/C (40 mg) and the suspension stirred overnight under an atmosphere of hydrogen. Removal of the catalyst by filtration through Celite followed by removal of the solvent gave the desired title compound as a colourless gum in quantitative yield (131 mg). C₅₃H₁₀₃N₇O₁₂ requires 1030. Found ES+: MH⁺ 1031, MHNa²⁺ 527. δH (CDCl₃) 1.1–2.0 (79H, br m, NH₂, C(Me)₃, CH(CH₂)₅, CH₂(CH₂)₂ CH₂N, CH₂CH₂NH), 2.7–3.4 (22H, br, CH₂N), 5.26, 5.45 (2H, br, NHBOC). δC (CDCl₃) partial 39.8 (1C, CH₂NH₂), 43.5, 46.5, 48.9 (10C, CH₂N), 78.5, 79.1 (6C, C(Me)₃), 155.3, 155.7 (6C, CO).

BOC Protected Dimethylated Hexamine

(B17) N,N'-bis(t-Butyloxycarbonylaminopropanoylaminobutyl)-2-(benzyloxyhexyl)malonamide

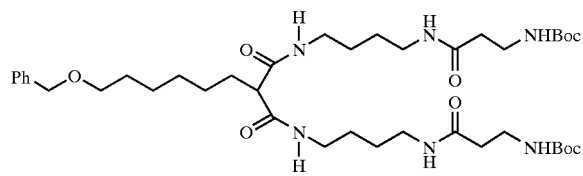

To a solution of BOC-β-alanine (2.5 g, 13.22 mmol) in dry dichloromethane (20 ml) was added N-methylmorpholine (1.6 ml, 14.55 mmol) followed by N-hydroxysuccinimide (91.67 g, 14.55 mmol). The flask was left stirring at 20° C. for 5 mins under argon before adding EDC (2.79 g, 14.55 mmol). The reaction was stirred overnight. Tlc showed that all the acid had been converted to the active ester. A solution of the B3 (2.86 g, 6.61 mmol) and triethylamine (4.6 ml, 33.05 mmol) in dichloromethane was added and the reaction stirred for 1 hr. A precipitate formed. The product was purified by chromatography (silica—5–10% methanol in dichloromethane) to give the title compound as a glass (2.31 g, 46%). The product on Tlc is green when sprayed with ninhydrin and contains bis-BOC-1,4-diaminobutane, an impurity in the starting material. C₄₀H₆₀N₆O₉ requires 776.5. Found ES: M⁺+1 777.6. δH (CDCl₃) 7.31 (5H, m, PhCH₂O), 4.47 (2H, s, PhCH₂O), 3.45 (2H, t, PhCH₂OCH₂), 3.4–3.1 (12H, dm, CH₂N), 3.02 (1H, t, CHR₃), 2.34 (4H, t, COCH₂), 1.9–1.2 (26H, m, CH₂+Me).

(B18) 13-Benzyloxyhexyl-2,6,11,15,20,24-hexa(t-butyloxycarbonyl)-2,6,11,15,20,24-hexaazapentacosane

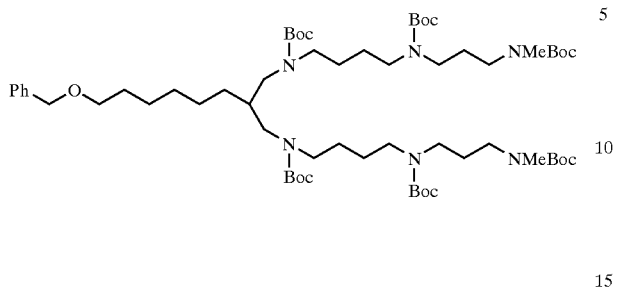

B17 (15.36 g, 15.36 mmol) was suspended in THF (240 ml) and borane methylsulphide complex (10M, 32 ml, 320 mmol) in THF (50 ml) added dropwise. Hydrogen was evolved and the tetraamide dissolved over 1 hr. The reaction was refluxed for 48 hr and carefully quenched with methanol. Solvent was removed in vacuo and hydrochloric acid added (6M, 100 ml). The reaction was refluxed for 1 hr at 60° C. and the hydrochloric acid removed in vacuo. The product was entrained in methanol and the solvent removed. The residue was dissolved in methanol containing 20% water and basified with solid sodium hydroxide and tert-butyl dicarbonate (32.7 g, 150 mmol) was added whilst maintaining the pH at 12. The basic solution was extracted with ethyl acetate, washed with brine, dried ($MgSO_4$) and evaporated to dryness. The residue was columned on silica (33% ethyl acetate in hexane) to give the title compound as an oil. $C_{60}H_{106}N_6O_{13}$ requires 1142. δH ($CDCl_3$) 7.31 (5H, m, $PhCH_2O$), 4.48 (2H, s, $PhCH_2O$), 3.44 (2H, t, $PhCH_2OCH_2$), 3.4–3.1 (20H, m, $CH_2N$), 3.02 (1H, t, $CHR_3$), 2.82 (6H, s, NMe), 1.9–1.2 (76H, m, $CH_2$+Me).

(B19) 8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octanol

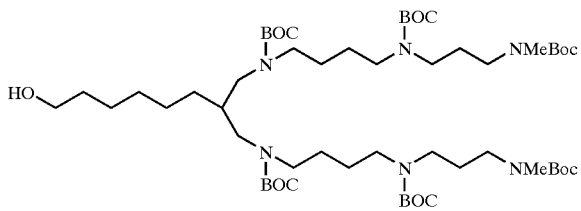

B18 (10.23 g, 89.6 mmol) was dissolved in t-butanol (100 ml) to which was added Raney nickel (8 ml) under argon. The atmosphere was changed to hydrogen and the reaction stirred for 48 hr. The Raney nickel was removed by filtration (glass fibre) and the product purified by chromatography on silica (50–75% ethyl acetate in hexane) to yield the title compound (6.75 g, 70%). $C_{55}H_{106}N_6O_{13}$ requires 1058.8. Found ES: $MNa^+$ 1081.8 δH ($CDCl_3$). 3.62 (2H, t, $HOCH_2$), 3.3–3.0 (20+1H, m, $CH_2N$+$CHR_3$), 2.84 (6H, s, NMe), 1.9–1.2 (76H, m, $CH_2$+Me).

(B20) 8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl Methanesulphonate

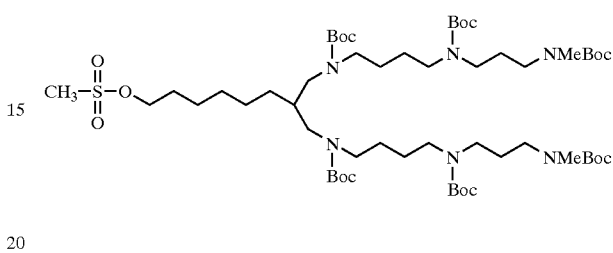

B19 (6.75 g, 6.54 mmol) was dissolved in dichloromethane (40 ml) containing triethylamine (1.2 ml) at 0° C. Methane sulphonyl chloride (0.6 ml, 7.8 mmol) was added in dichloromethane (10 ml) under argon. After 2 hr Tlc showed complete reaction (silica, 66% ethyl acetate in hexane). The title compound was evaporated to dryness and used in the next step without further purification. $C_{56}H_{108}N_6O_{15}S$ requires 1136.76. Found ES: $M^++1$ 1138.0 δH ($CDCl_3$). 4.21 (2H, t, $HOCH_2$), 3.3–3.0 (20+1H, m, $CH_2N$+$CHR_3$), 2.84 (6H, s, NMe), 2.99 (3H, s, SMe), 1.9–1.2 (76H, m, $CH_2$+Me).

(21) 13-Aminohexyl-2,6,11,15,20,24-hexakis(t-butyloxycarbonyl)-2,6,11,15,20,24-hexaazaeicosane

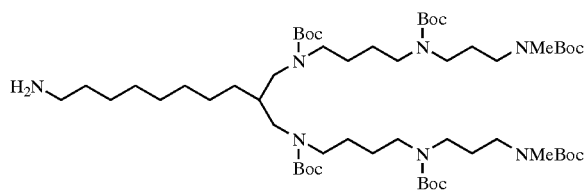

B20 (6.7 g, 6.5 mmol) was dissolved in DMF with heating, cooled and sodium azide (2.5 g) added portionwise. After 24 hr stirring the reaction was poured into brine (II) and extracted with ethyl acetate. The organic phase was washed with water, dried and evaporated to dryness. This material was used for the reduction without purification. The crude azide was dissolved in t-butanol (50 ml) and 10% palladium on carbon (2 g) added under argon. The atmosphere was changed to hydrogen and the reaction stirred for 48 hr. The catalyst was removed and the product evaporated to dryness. The product was purified by chromatography (silica saturated with triethylamine, 1–10% methanol in DCM containing 0.1% triethylamine) to yield the title compound (3 g) as a glassy solid. $C_{55}H_{107}N_7O_{12}$ requires 1057.8. Found ES: $M^++1$ 1058.7 δH ($CDCl_3$). 3.3–2.9 (20+1H, m, $CH_2N$+$CHR_3$), 2.83 (6H, s, NMe), 2.72 (2H, t, $NH_2CH_2$), 1.9–1.1 (76H, m, $CH_2$+Me).

C. DISUGAR INTERMEDIATES

This section contains the synthesis of the following:

(C4) N,N'-bis(Peracetylglucuronylaminoethyl) succinamic Acid

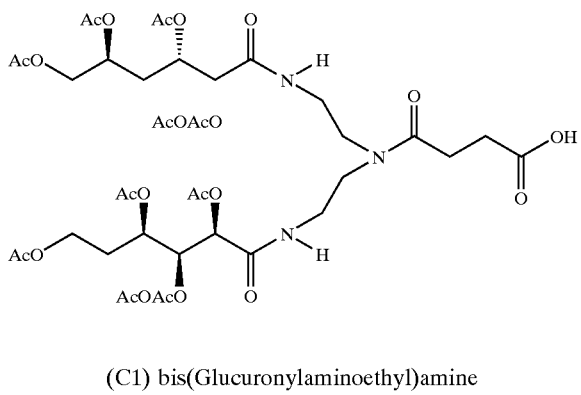

(C1) bis(Glucuronylaminoethyl)amine

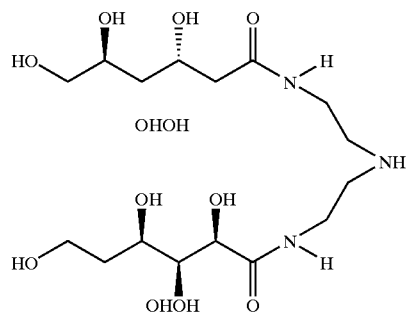

To a solution of d-gluconolactone (10.000 g, 56.14 mmol) in dry methanol (200 ml) under argon was added diethylenetriamine (2.825 g, 27.38 mmol) and the reaction stirred at room temperature overnight resulting in the formation of white precipitates. The solvent was removed from the resulting suspension giving a quantitative yield of the title compound as a pure white solid. $C_{16}H_{33}N_3O_{12}$ requires 459.2. Found $ES^+$: $MH^+$, 460.2. $\delta_H$ ($D_2O$) 2.79 (4H, t, $CH_2NHCH_2$), 3.40 (4H, dt, $CH_2NHCO$), 3.6–3.9 (8H, m, CHOH), 4.09 (2H, d, $CH_2OH$), 4.33 (2H, d, $CH_2OH$).

(C2) N,N'-bis(Glucuronylaminoethyl)-O-t-butylcarbamate

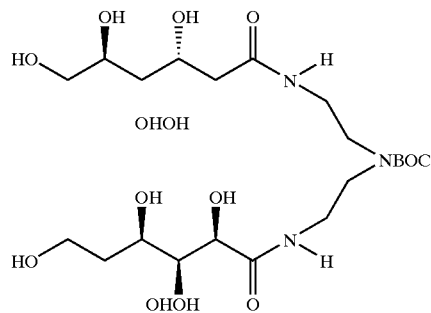

To C1 (7.000 g, 15.23 mmol) dissolved in methanol (235 ml) and water (90 ml) were added di-tert-butyl dicarbonate (3.990 g, 18.28 mmol) and triethylamine (1.542 g, 15.23 mmol) and the reaction stirred overnight at room temperature. The solvent was removed to quantitatively yield the BOC protected title compound which was used crude in the next synthetic step. $C_{20}H_{37}N_3O_{15}$ requires 559.2. Found $ES^+$: $MH^+$, 560.4. $\delta_H$ ($D_2O$) 1.47 (9H, s, $C(Me)_3$), 3.3–3.6 (8H, br, $CH_2N$), 3.6–3.8 (8H, m, CHOH), 4.09 (2H, br s, $CH_2OH$), 4.30 (2H, d, $CH_2OH$).

(C3) N,N'-bis(Peracetylglucuronylaminoethyl)-O-t-butylcarbamate

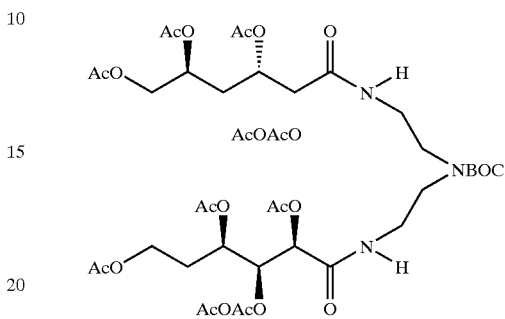

To a solution of crude C2 (15.23 mmol) in dry pyridine (50 ml) at 0° C. under argon was slowly added acetic anhydride (120 ml) and the solution allowed to warm to room temperature overnight. The majority of the solvent was removed and to the residues was added water (100 ml) and ethyl acetate (150 ml). The organic layer was separated off and the remaining aqueous layer extracted with more ethyl acetate (5×50 ml). The organics were combined, washed (1× citric acid, 4×water) and dried ($MgSO_4$) to yield on removal of the solvent a pale yellow gum. Gradient silica column chromatography (80% ethyl acetate in hexane to ethyl acetate) yielded the desired polyacetylated title compound (13.1 g 88% as a white solid. $C_{41}H_{61}N_3O_{24}$ requires 979.4. Found $ES^+$: $MNa^+$, 1002.4. $\delta_H$ ($CDCl_3$) 1.45 (9H, s, $C(Me)_3$), 2.02, 2.03, 2.04, 2.06, 2.09 (30H, 5×s, MeCO), 3.34 (8H, br, $CH_2N$), 4.10, 4.31 (4H, 2×dd, $CH_2OAc$), 5.06 (2H, m, CHOAc), 5.23 (2H, br, CHOAc), 5.45 (2H, q, CHOAc), 5.61 (2H, t, CHOAc), 6.61, 7.18 (2H, 2×br, NHCO).

(C4) N,N'-bis(Peracetylglucuronylaminoethyl) succinamic Acid

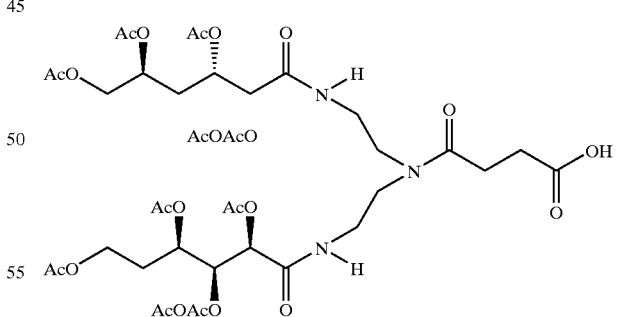

To C3 (3.000 g, 3.06 mmol) was added 1:1 trifluoroacetic acid: dichloromethane (15 ml) and the solution left at room temperature for 15 minutes. The solvent was removed and the residues dissolved in dry dichloromethane (40 ml). To this solution was added succinic anhydride (613 mg, 6.12 mmol) and triethylamine (1.549 g, 15.31 mmol) and the reaction stirred overnight at room temperature under argon. The solvent was removed, the residues taken up into dichloromethane (100 ml) and 1M aqueous HCl (50 ml) added.

The solution was rapidly stirred for 5 hours, the aqueous layer removed, and the remaining organic layer washed (3×water). This was then dried (MgSO$_4$) and the solvent removed to yield the title compound as a white solid (2.945 g, 98%). C$_{40}$H$_{57}$N$_3$O$_{25}$ requires 979.3 Found ES$^+$: MH$^+$, 980.2, MNa$^+$, 1002.2, ES$^-$: (M–H$^+$)$^-$ 978.2. δ$_H$ (CDCl$_3$) 2.03–2.23 (30H, 10×s, Me), 2.4–2.8 (4H, m, CH$_2$CO), 3.3–3.9 (8H, brm, CH$_2$N), 4.11 (2H, m, CH$_2$OAc), 4.35 (2H, dt, CH$_2$OAc), 5.09 (2H, 2×q, CHCH$_2$OAc), 5.18 (1H, d, CHCO), 5.27 (1H, d, CHCO), 5.44, 5.46, 5.58, 5.59 (4H, 4×t, CHOAc), 7.07, 7.15 (2H, 2×t, CONH).

D. LONG CHAIN AMINOACIDS

This section contains the syntheses of:

C$_{24}$ Aminoacid (D6) 24-Aminotetracosanoic Acid

NH$_2$(CH$_2$)$_{23}$CO$_2$H

C$_{18}$ Aminoacid (D10) 18-Aminooctadecanoic Acid

H$_2$N—(CH$_2$)$_{17}$—CO$_2$H

C$_{20}$ Reduced Bixin Aminoacid (D15) N-Aminoethyl-4,8,13,17-tetramethyl-1,20-dodecanamoic Acid Trifluoroacetate Salt C24 Aminoacid Containing Mid-chain Amide (D18) 12-(Aminododecanoylamino)dodecanoic Acid

NH$_2$—(CH$_2$)$_{11}$—CONH(CH$_2$)$_{11}$CO$_2$H (D19) 24-(Benzyloxycarbonylamino)tetracosanoic Acid C$_{24}$ Aminoacid (D1) 12-Aminododecanol Hydrochloride NH$_2$(CH$_2$)$_{11}$CH$_2$OH.HCl 12-Aminododecanoic acid (21.52 g, 100 mmol) was suspended in 100 ml THF and borane THF complex (500 mmol, 1M solution) added. The reaction was left overnight and carefully quenched with methanol before evaporation to small bulk. The residue was suspended in 1M HCl (500 ml) and heated at 40° C. for 1 hr and left overnight. The white solid was filtered off and washed with cold 1M HCl. The product was recrystallised from 1M HCl, filtered off and dried over P$_2$O$_5$ in vacuo to yield the title compound (18.70 g, 79%). Mp 120° C. softens, 169° C. liquid. C$_{12}$H$_{28}$N$_1$O$_1$Cl.1/5H$_2$O requires C: 59.70%, H: 11.86%, N: 5.80%. Found: C: 59.65%, H: 11.82%, N: 5.76%. C$_{12}$H$_{27}$N$_1$O$_1$ requires 201. Found ES+: MH$^+$ 202.1 (100%). δ$_H$ (CD$_3$CO$_2$D) 3.64 (2H, t, CH$_2$O), 3.06 (2H, t, NCH$_2$), 1.73 (2H, m, CH$_2$CH$_2$O), 1.57 (2H, m, NCH$_2$CH$_2$), 1.2–1.5 (16H, m, CH$_2$).

(D2) 12-(Dibenzylamino)dodecanol

Bn$_2$N(CH$_2$)$_{11}$CH$_2$OH

D1 (15 g, 63.2 mmol) was suspended in a mixture of dichloromethane (150 ml) and saturated sodium carbonate in water (150 ml). Benzyl bromide (189.6 mmol, 33.7 g, 23.5 ml) was added slowly. The suspension cleared and reaction was complete after 4 hr, aqueous ammonia (0.880, 30 ml) was added & the reaction left overnight. The organic layer was dried (MgSO$_4$) and evaporated to dryness. The product was stirred vigorously in refluxing hexane. The flask was left at –20° C. when crystals of the title compound slowly appeared. The crystals (Mp 45° C.) were collected by filtration (18.03 g, 75%). C$_{26}$H$_{39}$N$_1$O$_1$ requires C: 81.84%, H: 10.30%, N: 3.67%. Found: C: 81.64%, H: 10.24%, N: 3.54%. C$_{26}$H$_{39}$N$_1$O$_1$ requires 381. Found ES+: MH$^+$ 382 (100%). δ$_H$ (CDCl$_3$) 7.1–7.6 (10H, m, Ar), 3.64 (2H, t, CH$_2$O), 3.56 (4H, s, ArCH$_2$), 2.41 (2H, t, NCH$_2$), 1.1–1.8 (22H, dm, CH$_2$).

(D3) 12-(Dibenzylamino)dodecanal

Bn$_2$N(CH$_2$)$_{11}$CHO

To a solution of anhydrous DMSO (30 mmol, 2.13 ml) in dichloromethane (200 ml) at –78° C. was added carefully oxalyl chloride (2.6 ml, 30 mmol) in dichloromethane (60 ml). After 15 mins D1 (10 g, 26 mmol) was added in dichloromethane (60 ml) and the reaction stirred for 20 mins at –78° C. Triethylamine (28 ml) was added dropwise to the cold reaction. A precipitate formed and after 15 mins the reaction was allowed to reach room temperature. Water (100 ml) was added to the reaction which was extracted with dichloromethane. The organic layers were washed with water, dried (MgSO$_4$) and evaporated to dryness. The residue was chromatographed (SiO$_2$, hexane—10% ethyl acetate in hexane) to give the title compound as an oil (7.97 g, 80%). This compound is unstable and should be used on the day of preparation.

I.R. 1725 cm$^{-1}$ (COH). C$_{26}$H$_{37}$NO requires 379.29. Found ES+: MH$^+$ 380.29. δ$_H$ (CDCl$_3$) 1.32 (14H, br, (CH$_2$)$_7$(CH$_2$)$_2$N), 1.61 (4H, 2×p, CH$_2$CH$_2$N, CH$_2$CH$_2$CO), 2.43, 2.44 (4H, 2×t, CH$_2$N, CH$_2$CO), 3.60 (4H, s, CH$_2$Ph), 7.2–7.5 (10H, m, Ph), 9.78 (1H, t, COH). d$_C$ (CDCl$_3$) 22.0, 26.9, 27.1, 29.0, 29.3, 29.4, 29.5 (9C, (CH$_2$)$_9$CH$_2$N), 43.8 (1C, CH$_2$COH), 53.3 (1C, CH$_2$N), 58.2 (2C, CH$_2$Ph), 126.6 (2C, CH(CH)$_2$C), 128.0 (4C, CHC), 128.6 (4C, CHCHC), 140.0 (2C, CCH$_2$N), 202.3 (1C, COH).

(D4) 11-(Carboxyundecyl)triphenylphosphonium Bromide

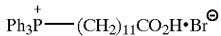

To 12-bromododecanoic acid (3.000 g, 10.7 mmol) suspended in acetonitrile (12 ml) was slowly added triphenylphosphine (2.818 g, 10.7 mmol). The reaction was heated at 100° C. (no condenser) with argon blowing over the flask until the reaction was a fusion, then maintained at 100° C. (with condenser) for 24 hrs. The warm residues were dissolved in acetonitrile (18 ml) and added dropwise to rapidly stirred cold (dry ice) diethyl ether. The white precipitate formed was then filtered off and the title compound dried (5.353 g, 92%). Mp 110–112° C. $C_3OH_{38}O_2PBr$ requires C: 66.54%, H: 7.07%. Found: C: 66.42%, H: 7.10%. $b_P$ (CDCl$_3$) 24.3 (s). $\delta_H$ (CDCl$_3$) 1.05–1.30 (12H, br, $(CH_2)_6(CH_2)_2CO_2H$), 1.53 (6H, br, $(CH_2)_2CH_2P$, $CH_2CH_2CO_2$(2H, t, $CH_2CO_2$), 3.55 (2H, br, $CH_2P$), 7.6–7.8 (15H, m, Ph). $d_C$ (CDCl$_3$) 22.1, 22.3, 22.8, 24.5, 28.8, 28.9, 30.0, 30.2 (10C, $(CH_2)_{10}CO_2H$), 34.2 (1C, $CH_2P$), 117.3, 118.7 (3C, CP), 130.3, 130.5 (6C, CHCHCP), 133.3, 133.5 (6C, CHCP), 134.9 (3C, CH(CH)$_2$CP), 177.4 (1C, $CO_2H$).

(D5) 24-(Dibenzylamino)-12-tetracosenoic Acid

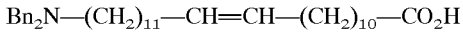

The phosphonium salt D4 (13.52 g, 25 mmol) was dissolved in dry DMSO (40 ml) under argon at 0OC (no DMSO solidification). 2.2 Equivalents of 2.0M LDA(25 ml) were added, the solution turning orange. The reaction was left at 0° C. for ½ hour, and to the now dark orange solution was added a solution of D3 (7.97 g, 21 mmol) in dry THF (30 ml). The solution was maintained at 0° C. for 4 hours then added to 2M HCl (50 ml). The aqueous layer was extracted with dichloromethane, the fractions combined, dried (MgSO$_4$) and the solvent removed to yield the crude material as a pale yellow gum. Silica column chromatography (30–100% ethyl acetate in hexane) yielded the title compound (6.20 g, 53%), as a pale yellow gum. $C_{38}H_{59}NO_2$ requires 561.46. Found ES+: MH$^+$ 562.53, ES–: (M–H$^+$) 560.55. $\delta_H$ (CDCl$_3$) 1.26 (30H, br, $(CH_2)_8CH_2CH=CHCH_2(CH_2)_7$), 1.42–1.72 (4H, m, $CH_2CH_2CO_2H$, $CH_2CH_2N$), 2.02 (4H, dxt, $CH_2CH=CHCH_2$), 2.34 (2H, t, $CH_2CO_2H$), 2.46 (2H, t, $CH_2N$), 3.65 (4H, s, $CH_2Ph$), 5.36 (2H, t, CH=CH), 7.2–7.4 (10H, m, Ph). $\delta_C$ (CDCl$_3$) 25.0, 26.4, 27.2, 29.3, 29.6 (19C, $(CH_2)_{10}CH=CH(CH_2)_9$), 34.5 (1C, $CH_2CO_2H$), 52.9 (1C, $CH_2N$), 57.7 (2C, $CH_2Ph$), 127.0 (2C, CH(CH)$_2$C), 128.2 (4C, CHC), 129.1 (4C, CHCHC), 129.9 (2C, CH=CH), 138.6 (2C, CCH$_2$N), 179.2 (1C, $CO_2H$).

(D6) 24-Aminotetracosanoic Acid

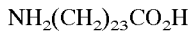

D5 (6.2 g) under an atmosphere of hydrogen was heated at 60° C. (to avoid the monobenzyl product) overnight in glacial acetic acid using Pearlman's catalyst (10% w/w). The reaction was filtered through glass fibre and evaporated to dryness. The title compound was crystallised from acetic acid/ether (4.2 g, 100%) and subjected to high vacuum to remove traces of acetic acid. Mp 151–155° C. $C_{24}H_{49}NO_2 \cdot 0.75MeCO_2H$ requires C: 71.44%, H: 12.23%, N: 3.27%. Found: C: 71.43%, H: 12.15%, N: 3.26%. $C_{24}H_{49}NO_2$ requires 383.38. Found ES+: MH$^+$ 384.29. $\delta_H$ (CD$_3$OD+TFA) 1.32 (38H, br, $(CH_2)_{19}(CH_2)_2NH_2$), 1.65 (4H, br, $CH_2CH_2NH_2$, $CH_2CH_2CO_2H$), 2.33 (2H, t, $CH_2CO_2H$), 2.74 (2H, m, $CH_2NH_2$). $\delta_C$ (CD$_3$OD+TFA) partial 33.8 (1C, $CH_2CO_2H$), 35.3 (1C, $CH_2NH_2$).

C$_{18}$ Aminoacid

(D7) 6-(Dibenzylamino)-1-hexanol

Benzyl bromide (61 ml, 511 mmol) was added to a stirred solution of 6-amino-1-hexanol (20 g, 170 mmol) and triethylamine (142 ml, 1.02 mol) in acetonitrile (500 ml) at room temperature for two days. The acetonitrile solution was concentrated to 100 ml and diluted with water. The aqueous phase was extracted with ethyl acetate, washed with brine, dried (MgSO$_4$) and evaporated to dryness to yield an orange oil. The product was chromatographed on silica (hexane—50% ethyl acetate/hexane) to yield the title compound as a colourless oil (25 g, 50%). $\delta_H$ (CDCl$_3$) 7.23–7.39 (10H, m, (ArH), 3.59 (6H, t+ds, $CH_2OH+ArCH_2$), 2.42 (2H, t, $CH_2N$), 1.47–1.56 (4H, m, $CH_2CH_2NH_2+CH_2CH_2OH$), 1.24–1.32 (4H, m, 2×$CH_2$).

(D8) 6-(Dibenzylamino)hexanal

To a stirred solution of DMSO (20 mmol, 1.41 ml) in dichloromethane (100 ml) at –78° C. was carefully added oxalyl chloride (1.7 ml, 20 mmol) in dichloromethane (30 ml). After 15 mins D7 (5 g, 16.83 mmol) was added in dichloromethane (30 ml) maintaining the temperature at –78° C. The reaction was stirred for 20 mins and triethylamine (14 ml) added dropwise. A precipitate formed, after 15 mins the reaction was allowed to reach room temperature. Water (100 ml) was added to the reaction which was extracted with dichloromethane. The organic layers were washed with water, dried (MgSO$_4$) and evaporated to dryness. The residue was chromatographed (SiO$_2$, hexane –20% ethyl acetate in hexane) to give the title compound as an oil (4.10 g, 83%). $C_{20}H_{25}NO$ requires C: 81.31%, H: 8.53%, N: 4.74%. Found: C: 81.00%, H: 8.49%, N: 4.63%. $C_{20}H_{25}NO$ requires 295. Found ES+: MH$^+$ 296. $\delta_H$ (CDCl$_3$) 9.71 (1H, (1H, s, CHO), 7.2–7.5 (10H, m, ArH,), 3.57 (4H, s, ArCH$_2$), 2.3–2.5 (4H, dt, CH$_2$), 1.2–1.7 (6H, dm, CH$_2$).

(D9) 18-(Dibenzylamino)-12-octadecenoic Acid

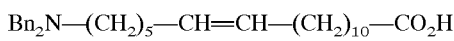

D4 (1.082 g, 2 mmol) was dissolved in dry DMSO (5 ml) under argon at ~0° C. (no DMSO solidification). 2.2 equivalents of 2.0M LDA (4 ml) was added, the solution turning orange. The reaction was left at 0° C. for 1/2 hour, and to the now dark orange solution was added a solution of D8 (0.7 g, 2 mmol) in dry THF (10 ml). The solution was maintained at 0° C. for 4 hours then added to 2M HCl (50 ml). The aqueous layer was extracted with ethyl acetate, the fractions combined, dried (MgSO$_4$) and the solvent removed to yield the crude material as a pale yellow gum. Silica column chromatography (30% ethyl acetate in hexane or 5% methanol in dichloromethane) yielded the title compound (453 mg, 53%), as a low melting (Mp 21° C.) white solid. $C_{32}H_{47}NO_2$ requires C: 80.45%, H: 9.92%, N: 2.93%. Found: C: 80.20%, H: 9.92%, N: 2.74%. $C_{38}H_{59}NO_2$ requires 477. Found ES+: MH$^+$ 478. $\delta_H$ (CDCl$_3$) 8.6–9.2 (1H, vbr, (CO$_2$H), 7.39–7.21 (10H, m, ArH), 5.37–5.29 (2H, m, trans HC=CH), 3.63 (4H, s, PhCH$_2$), 2.48–2.43 (2H, t, NCH$_2$), 2.36–2.31 (2H, t, CH$_2$CO$_2$H), 2.01–1.97 (2H, t, CH$_2$CH=CH), 1.66–1.55 (4H, m, CH$_2$), 1.29–1.24 (18H, m, CH$_2$).

(D1) 18-Aminooctadecanoic Acid $H_2N-(CH_2)_{17}-CO_2H$

D8 (13 g) under an atmosphere of hydrogen was heated at 60° C. overnight in glacial acetic acid with Pearlman's catalyst (10% w/w). The reaction was filtered hot through glass fibre and evaporated to dryness. The product was crystallised from acetic acid/ether (8.2 g, 100%). The title compound was subjected to high vacuum to remove traces of acetic acid. Mp 162–163° C. $C_{24}H_{49}NO_2 \cdot 0.25H_2O$ requires C: 71.12%, H: 12.43%, N: 4.61%. Found: C: 71.20%, H: 12.35%, N: 4.49%. $C_{24}H_{49}NO_2$ requires 299. Found ES+: $MH^+$ 300. $d_H$ ($CD_3CO_2D$) 3.06 (2H, t, $CH_2NH_2$), 2.38 (2H, t, $CH_2CO_2H$), 1.63–1.73 (4H, m, $CH_2CH_2CO_2H+CH_2CH_2NH_2$), 1.33 (26H, m, $CH_2$).

$C_{20}$ Reduced Bixin Aminoacid

(D11) Hydrogen Methyl 4,8,13,17-tetramethyl-1,20-dodecanedioate

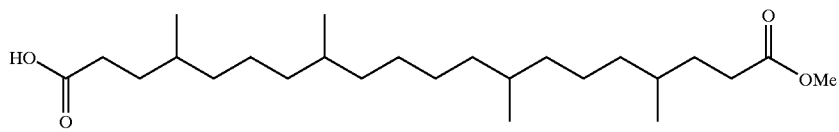

A suspension of bixin (9.959 g, 24.59 mmol) was stirred overnight in methanol (200 ml) in the presence of a hydrogen atmosphere and 10% Pd/C catalyst (1 g). The catalyst and solvent were removed to yield an opaque yellow viscous oil, silica tlc r.f. 0.4 (25% ethyl acetate in hexane) purified by gradient (20–35% ethyl acetate in hexane) silica chromatography to yield the title compound as a very pale yellow clear viscous oil (7.181 g, 71%). I.R. 1710 cm$^{-1}$ ($CO_2H$), 1743 cm$^{-1}$ ($CO_2Me$). $C_{24}H_{48}O_4$ requires 412.36. Found ES+: $MNa^+$ 435.38. $\delta_H$ ($CDCl_3$) 0.85–1.0 (12H, m, CHMe), 1.0–1.8 (28H, br, $CH_2$, $CHCH_3$), 2.35 (4H, m, $CH_2CO$), 3.70 (3H, s, OMe).

(D12) N-aminoethyl-O-t-Butylcarbamate

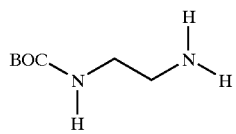

BOC-ON (16.4 g, 0.066 mmol) was added to a stirred mixture of ethylenediamine (13.4 ml, 0.2 mmol) and triethylamine (28 ml, 0.2 mmol) at room temperature under argon and left overnight. Ethyl acetate was added and the product extracted into potassium dihydrogen orthophosphate solution. The extracts were combined and basified to pH12 with sodium hydroxide. The aqueous basic solution was extracted with ethyl acetate, the combined organic phases washed with brine, dried and evaporated to dryness to yield the title compound which analysed without further purification. Yield 6.4 g. $C_7H_{16}N_2O_2$ requires 160. Found ES+: $MH^+$ 161. $\delta_H$ ($CDCl_3$) 5.12 (1H, br, CONH), 3.19 (2H, dt, OCONH$CH_2$), 2.93 (2H, s, $NH_2$), 2.82 (2H, t, $CH_2N$), 1.42 (9H, s, Me).

(D13) Methyl N—(t-Butyloxycarbonylaminoethyl)-4,8,13,17-tetramethyl-1,20-dodecanamoate

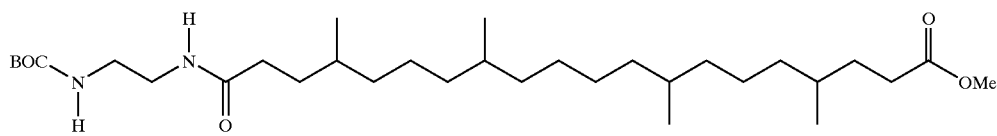

To D11 (7.181 g, 17.4 mmol) in dry dichloromethane (50 ml) under argon was added triethylamine (1.761 g, 17.4 mmol), EDC (5.171 g, 17.4 mmol) and N-hydroxysuccinimide (2.002 g, 17.4 mmol). The solution was left for three hours, during which time the formation of the slower moving NHS active ester was followed by silica tlc (r.f. 0.25, 25% ethyl acetate in hexane). Once complete ester formation was achieved, D12 (3.067 g, 19.1 mmol) was added in dichloromethane (20 ml) and the reaction left 48 hrs. Purification on silica (50% ethyl acetate in hexane) yielded the title compound (4.285 g, 44%), silica tlc r.f. 0.15 (25% ethyl acetate in hexane). $C_{32}H_{62}N_2O_5$ requires 554.47. Found ES+: $MH^+$ 555.48, $MNa^+$ 557.41. $\delta_H$ ($CDCl_3$) 0.7–0.9 (12H, m, CHMe), 0.8–1.8 (28H, br m, CHMe, $CH_2$), 1.41 (9H, s, $C(Me)_3$), 2.15 (2H, d×t, $CH_2CONH$), 2.27 (2H, m, $CH_2CO_2Me$), 3.15–3.35 (4H, m, $CH_2NH$), 3.63 (3H, s, OMe), 5.33 (1H, t, $NHCO_2$), 6.65 (1H, t, NHCO). $\delta_C$ ($CDCl_3$) 19.1, 19.5, 24.2, 27.3, 28.2, 31.7, 32.2, 32.6, 34.3, 37.0 (25C, $CH_2$, CHMe, $C(CH_3)_3$), 40.2, 40.4 (2C, $CH_2N$), 51.2 (1C, OMe), 79.2 (1C, $C(Me)_3$), 156.8 (1C, $NHCO_2$), 174.2, 174.4 (2C, $CO_2Me$, CONH).

(D14) N—(t-Butyloxycarbonylaminoethyl)-4,8,13,17-tetramethyl-1,20-dodecanamoic Acid

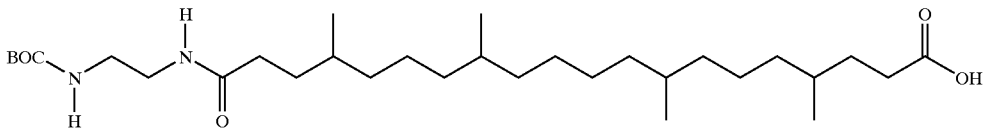

To D13 (4.285 g, 7.722 mmol) in methanol (35 ml) was added a suspension/solution of lithium hydroxide (3.239 g, 77.22 mmol) in water (10 ml). This was stirred for 2 hours then poured into 10% citric acid solution and extracted with ethyl acetate. These organic fractions were combined, washed with water and the solvent removed to yield the title compound. With dichloromethane:methanol:water 6:1:1 on silica the tlc of D13 and D14 have $R_f$ of 0.35 and 0.05 respectively. $C_{31}H_{60}N_2O_5$ requires 540.45. Found ES+: MH+ 541.48, MNa+ 563.45. $\delta_H$ (CDCl$_3$) 0.85–1.0 (12H, m, Me), 1.0–1.8 (28H, br m, CH$_2$, CH), 1.46 (9H, s, C(Me)$_3$), 2.20 (2H, m, CH$_2$CONH), 2.36 (2H, m, CH$_2$CO$_2$), 3.15–3.45 (4H, m, CH$_2$N), 5.16 (1H, t, NHCO$_2$), 6.55 (1H, t, NHCO). $\delta_C$ (CDCl$_3$) 19.3, 19.7, 24.2, 27.2, 28.3, 31.8, 32.3, 32.6, 34.4, 36.9 (25C, CH$_2$, CHMe, C(CH$_3$)$_3$), 40.0, 40.6 (2C, CH$_2$N), 79.6 (1C, C(Me)$_3$), 157.0 (1C, NHCO$_2$), 174.5 (1C, CONH), 179.5 (1C, CO$_2$H).

(D15) N-Aminoethyl-4,8,13,17-tetramethyl-1,20-dodecanamoic Acid Trifluoroacetate Salt

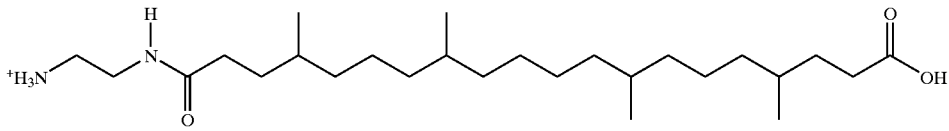

D14 was taken up into 96% TFA and left for 30 minutes. The solvent was removed to give the amino acid as a viscous oil which after silica chromatography (15% methanol in dichloromethane+0.1% acetic acid) gave the title compound as a colourless solid/gum, silica tlc r.f. 0.25, ninhydrin +ve (6:1 dichloromethane:methanol). The yield for the two steps D14 to D15 was 2.044 g, 60%. $C_{26}H_{52}N_2O_3$ requires 440.40. Found ES+: MH+ 441.36. $\delta_H$ (CD$_3$OD) 0.95–1.1 (12H, m, Me), 1.1–1.9 (28H, br m, CH, CH$_2$), 2.38 (4H, m, CH$_2$CO), 3.20 (2H, t, CH$_2$NH$_3^+$), 3.60 (2H, t, CH$_2$NHCO). $\delta_C$ (CD$_3$OD) 20.1, 20.5, 22.0, 25.6, 28.6, 33.6, 33.8, 34.0, 35.0, 38.4, 38.6 (22C, CH, CH$_2$, Me), 40.9 (2C, CH$_2$N), 177.9 (1C, CONH), 179.4 (1C, CO$_2$H).

C24 Aminoacid Containing Mid-chain Amide

(D16) 12-(t-Butyloxycarbonylamino)dodecanoic Acid

BocNH—(CH$_2$)$_{11}$—CO$_2$H

12-Aminododecanoic acid (2.15 g, 10 mmol) was dissolved in 1M NaOH (50 ml) at 50° C. BOC anhydride (2.33 g, 10 mmol) was added to the reaction which was stirred for 30 mins. The reaction was poured into stirred 10% citric acid (100 ml) and the white solid filtered off. The solid was washed with citric acid, water and dried in vacuo. The product was dissolved in ether and filtered before evaporating to dryness. The title compound was crystallised from hexane (2.33 g, 74%). Mp 72–76° C. $C_{17}H_{33}NO_4$ requires C: 64.73%, H: 10.55%, N: 4.44%. Found: C: 64.78%, H: 10.58%, N: 4.41%. $C_{24}H_{49}NO_2$ requires 315. Found ES+: MH+ 316. $\delta_H$ (CDCl$_3$) 3.08 (2H, t, CH$_2$NH$_2$), 2.33 (2H, t, CH$_2$CO$_2$H), 1.6 (2H, m, CH$_2$CH$_2$NH$_2$), 1.44 (11H, s+m, CH$_2$CH$_2$CO$_2$H+Boc), 1.26 (14H, m, CH$_2$).

(D17) 12-(t-Butyloxycarbonylaminododecanoylamino)dodecanoic Acid

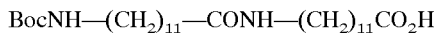

BocNH—(CH$_2$)$_{11}$—CONH—(CH$_2$)$_{11}$CO$_2$H

To D16 (1.59 g, 5.05 mmol) in stirred dichloromethane (20 ml) was added DBU (0.755 ml, 5.05 mmol), followed by N-hydroxysuccinimide (0.581 g, 5.05 mmol) and EDC (0.968 g, 5.05 mmol). The reaction was left overnight to go to completion. Chloroform (30 ml) containing 12-aminododecanoic acid (1.087 g, 5.05 mmol) and DBU (1.51 ml, 10.1 mmol) was added. After 3 hours the reaction was poured into 10% citric acid (100 ml) and extracted with dichloromethane (3×50 ml). The organic phases were dried (MgSO$_4$) and evaporated to dryness. The solid residue was triturated with refluxing hexane & dissolved in refluxing ethyl acetate. The solution was filtered hot and allowed to crystallise to yield the title compound (2.33 g, 90%). Mp 85–87° C. $C_{29}H_{56}N_2O_5$ requires 512. Found ES+: MH+ 513. $\delta_H$ (CDCl$_3$) 5.74 (1H, brt, CONH), 4.57 (1H, br, CONH), 3.0–3.3 (2×2H, q+m, CH$_2$NH), 2.30 (2H, t, CH$_2$CO), 2.15 (2H, t, CH$_2$CO), 1.60 (4H, m, CH$_2$), 1.2–1.5 (9+32H, m, CH$_2$).

(D18) 12-(Aminododecanoylamino)dodecanoic Acid

NH$_2$—(CH$_2$)$_{11}$—CONH—(CH$_2$)$_{11}$CO$_2$H

96% TFA (4% water, 7 ml) was added to D17 (2.3 g, 4.5 mmol) and the resulting solution stirred for 30 min. The reaction was evaporated to dryness and azeotroped with toluene/methanol before submitting to high vacuum. The title compound was recrystallised from ether containing acetic acid as a white solid (2.12 g). Mp 66–68° C. $C_{24}H_{48}N_2O_3$ requires 412. Found ES+: MH+ 413. $\delta_H$ (CD$_3$CO$_2$D) 3.26 (2H, t, CH$_2$NH), 3.09 (2H, t, CH$_2$NH), 2.38 (2H, t, CH$_2$CO), 2.28 (2H, t, CH$_2$CO), 1.5–1.9 (4H, m, CH$_2$CH$_2$NH), 1.5–1.25 (32H, t, CH$_2$).

(D19) 24-(Benzyloxycarbonylamino)tetracosanoic Acid

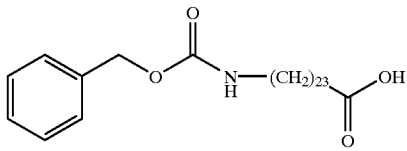

To D6 (0.500 g, 1.30 mmol) and DBU (794 mg, 5.21 mmol) in refluxing methanol (100 ml) was added neat benzylchloroformate and the reaction refluxed for 3 hours until complete conversion of D6 to either the protected amino acid D19 or its methyl ester was observed. The solvent was removed and the residues taken up into dioxane (60 ml) and water (2 ml) and lithium hydroxide (1 g) added. The reaction was then refluxed for 2 hours until hydrolysis of the methyl ester derivative to D19 was complete. The solvent was removed, the residues suspended in 1M HCl (100 ml) and extracted with hot ethyl acetate (300 ml). The hot ethyl acetate was dried ($MgSO_4$) and the solvent volume reduced to 40 ml. The solution/suspension was left at $-10°$ C. for 1 hour, allowed to warm to room temperature and the resulting white precipitates filtered off and dried under vacuum to yield the title compound (585 mg, 87%). M.Pt 102–104° C. $C_{32}H_{55}NO_4$ requires 517.4. Found $ES^-$: $MCl^-$, 552.6. $\delta_H$ ($d_6DMSO$), 1.32 (38H, s, $(CH_2)_{19}(CH_2)_2N$), 1.52 (2H, p, $CH_2CH_2CO_2H$), 1.65 (2H, p, $CH_2CH_2NH$), 2.35 (2H, t, $CH_2CO_2H$), 3.18 (2H, t, $CH_2N$), 5.14 (2H, s, $CH_2Ph$), 7.35 (5H, m, Ph).

E. LIPID POLYAMINE INTERMEDIATES

This section contains the synthesis of:

(E2) N-{8-[t-Butyloxycarbonylaminobutyl(t-butyloxycarbonyl)-amino]-7-[t-butyloxycarbonylaminobutyl(t-butyloxycarbonyl)aminomethyl]octyl}-23-aminotetracosanamide

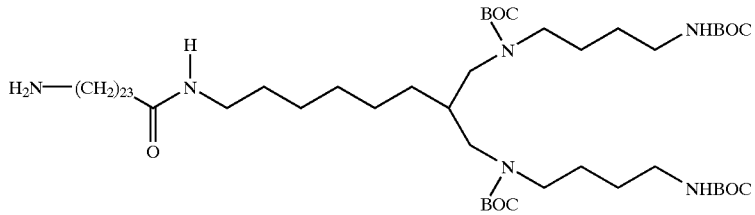

(E4) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-23-aminotetracosanamide

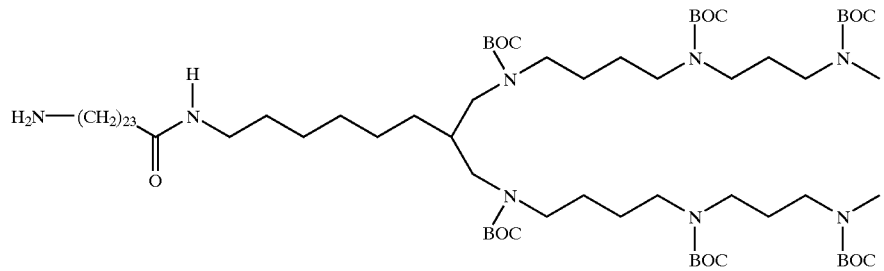

(E8)

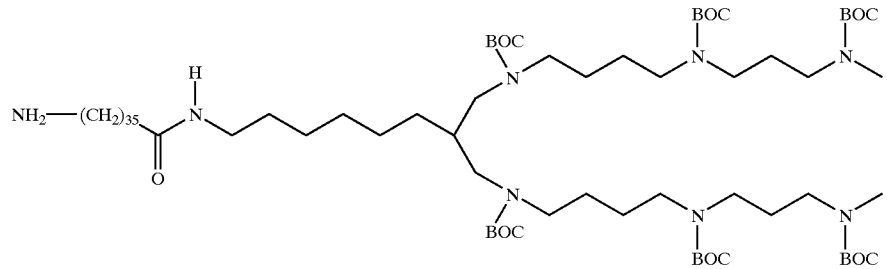

(E1) N-{8-[t-Butyloxycarbonylaminobutyl(t-butyloxycarbonyl)-amino]-7-[t-butyloxycarbonylaminobutyl(t-butyloxycarbonyl)aminomethyl]octyl}-23-benzyloxycarbonylamino)tetracosanamide

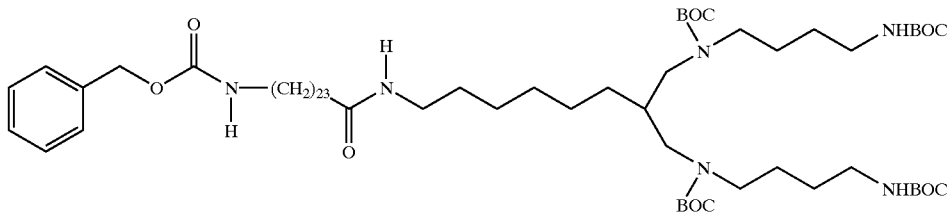

D19 (448 mg, 0.865 mmol), EDC hydrochloride (249 mg, 1.30 mmol), N-hydroxysuccinimide (149 mg, 1.30 mmol) and DBU (263 mg, 1.73 mmol) were dissolved in anhydrous dichloromethane (10 ml) and activated ester formation left overnight at room temperature under argon. B8 (589 mg, 0.82 mmol) was added and the reaction left for a further five hours. The solvent was removed and the residues purified by gradient silica column chromatography (40–60% ethyl acetate in hexane) to yield the title compound as a colourless glass (887 mg, 88%). $C_{69}H_{126}N_6O_{11}$ requires 1214.9. Found ES$^+$: MH$^+$, 1215.9. $\delta_H$ (CDCl$_3$) 1.24 (48H, br, (CH$_2$)$_{20}$ (CH$_2$)$_2$ N, (CH$_2$)$_4$CH), 1.43 (48H, br, Me, CH$_2$CH$_2$N), 2.03 (1H br, CH), 2.18 (2H, t, CH$_2$CO), 3.00–3.35 (16H, brm, CH$_2$N), 4.4–4.6 (3H, br, NHCO$_2$), 5.09 (2H, s, CH$_2$O), 5.90 (1H, br, CONH), 7.34 (5H, m, Ph).

(E2) N-{8-[t-Butyloxycarbonylaminobutyl(t-butyloxycarbonyl)amino]-7-[t-butyloxycarbonylaminobutyl(t-butyloxycarbonyl)aminomethyl]octyl}-23-aminotetracosanamide To E1 (877 mg) dissolved in tert-butanol (60 ml) was added Pearlmans catalyst (500 mg), ammonium formate (3 9) and Raney nickel (approximately 1 ml). The reaction was heated at 45° C. overnight and to maintain a hydrogen atmosphere the reaction was fitted with a bubbler. The catalysts were filtered off and the solvent removed to give a colourless gum which was purified by silica column chromatography (10% methanol in dichloromethane+0.1% triethylamine) to yield the title compound as a colourless glass/solid (744 mg, 95%). $C_{61}H_{120}N_6O_9$ requires 1080.9. Found ES$^+$: MH$^+$, 1082.1, ES$^-$: MCl$^-$, 1116.1. $\delta_H$ (CDCl$_3$) 1.24 (46H, br, (CH$_2$)$_{19}$ (CH$_2$)$_2$CO), 1.42 (50H, br, Me, CH$_2$CH$_2$N, CH$_2$CH$_2$CO), 1.95 (1H, br, CH), 2.14 (2H, t, CH$_2$CO), 2.95 (2H, t, CH$_2$NH$_2$), 3.0–3.3 (14H, m, CH$_2$N), 4.69 (2H, br, NHCO$_2$), 5.64 (1H, t, NHCO).

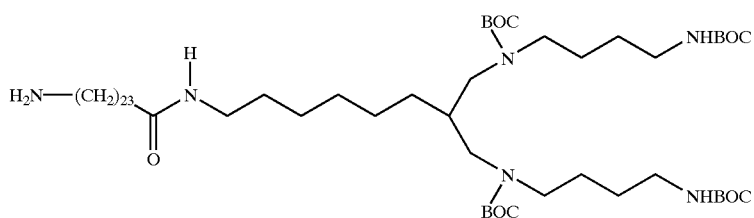

(E3) N-{8-[Methyl(t-butyloxycarbonyl)aminopropyl (t-butyloxycarbonyl)aminobutyl(t-butyloxycarbonyl) amino]-7-[methyl(t-butyloxycarbonyl)aminopropyl (t-butyloxycarbonyl)aminobutyl(t-butyloxycarbonyl) aminomethyl]octyl}-23-(benzyloxycarbonylamino) tetracosanamide atmosphere the reaction was fitted with a bubbler. The catalysts were filtered off and the solvent removed to give a colourless gum which was purified by silica column chromatography (10% methanol in dichloromethane+0.1% triethylamine) to yield the title compound as a colourless glass/solid (1.088 g, 94%). $C_{79}H_{154}N_8O_{13}$ requires 1423.2.

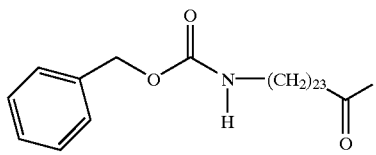
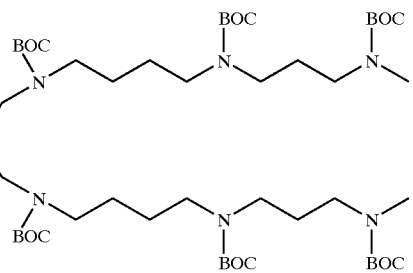

D19 (580 mg, 1.12 mmol), EDC hydrochloride (429 mg, 2.24 mmol), N-hydroxysuccinimide (193 mg, 1.68 mmol) and DBU (341 mg, 2.24 mmol) were dissolved in anhydrous dichloromethane (30 ml) and activated ester formation left overnight at room temperature under argon. B21 (1.186 g, 1.12 mmol) in anhydrous dichloromethane (20 ml) was added and the reaction left for a further five hours. The solvent was removed and the residues purified by gradient silica column chromatography (40–60% ethyl acetate in hexane) to yieldthe title compound as a colourless glass (1.261 g, 72%). $C_{87}H_{16}ON_8O_{15}$ requires 1557.2. Found ES$^+$: MH$^+$, 1558.3. $\delta_H$ (CDCl$_3$) 1.24 (46H, $(CH_2)_{19}(CH_2)_2$ CO, $(CH_2)_4CH$), 1.4–1.8 (72H, br+m, $(Me)_3C$, $CH_2CH_2CO$, $CH_2CH_2N$), 2.03 (1H, br, CH), 2.21 (2H, t, $CH_2CO$), 2.83 (6H, s, MeN), 3.0–3.35 (24H, m, $CH_2N$), 4.73 (1H, br, NHCO$_2$), 5.3 (2H, s, $CH_2O$), 6.08 (1H, br, NHCO), 7.34 (5H, m, Ph).

(E4) N-{8-[Methyl(t-butyloxycarbonyl)aminopropyl (t-butyloxycarbonyl)aminobutyl(t-butyloxycarbonyl) amino]-7-[methyl(t-butyloxycarbonyl)aminopropyl (t-butyloxycarbonyl)-aminobutyl(t-butyloxycarbonyl)aminomethyl]octyl}-23-aminotetracosanamide Found ES$^+$: MH$^+$, 1424.3. $\delta_H$ (CDCl$_3$) 1.24 (48H, $(CH_2)_{20}$ $CH_2CO$, $(CH_2)_4CH$), 1.43 (70H, br+m, $(Me)_3C$, $CH_2CH_2N$), 1.95 (1H, br, CH), 2.14 (2H, t, $CH_2CO$), 2.80 (2H, t, $CH_2NH_2$), 2.83 (6H, s, NMe), 3.0–3.35 (22H, m, $CH_2N$), 5.65 (1H, br, CONH).

(E5) 36—Chlorohexatriaconta-12,24-dienoic Acid

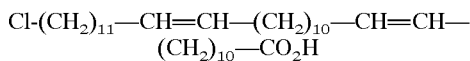

To a rapidly stirring suspension of silica (200 ml) and 50% dichloromethane in hexane (200 ml) was slowly added tosic acid (2 g) in water (6 ml). The suspension was stirred for 10 minutes and used to pack a column. After washing the column with 50% dichloromethane in hexane 35—Chloro-1-(1,3-dioxalan-2-yl)pentatriaconta-12,24-diene (4.04 g) was loaded and eluted over 2 hours with 50% dichloromethane in hexane to give the aldehyde 2.5264 g, 66% as a white waxy solid. To PDC (3.792 g, 10.080 mmol) in anhydrous DMF (30 ml) was added the aldehyde (2.5264 g, 4.582 mmol) in anhydrous DMF (30 ml) and the reaction stirred at ambient temperature under argon for 2 days. The reaction was poured into water (500 ml), extracted with hexane and the combined hexane fractions washed with

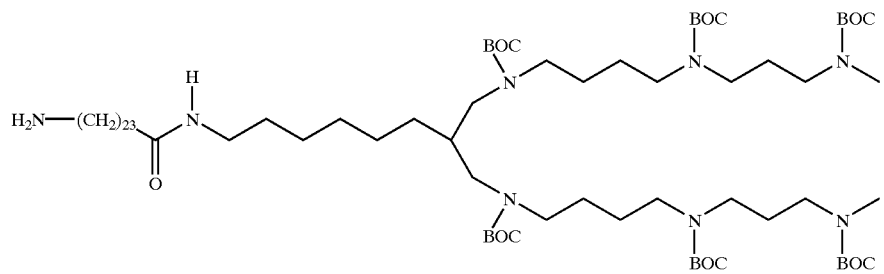

To E3 (1.260 g) dissolved in tert-butanol (60 ml) was added Pearlmans catalyst (500 mg), ammonium formate (3 g) and Raney nickel (approximately 1 ml). The reaction was heated at 45° C. overnight and to maintain a hydrogen water (3×150 ml). The solution was dried (MgSO$_4$), and the solvent removed to yield a brown oil which was purified by silica gradient chromatography eluting with 10–20% ethyl acetate in hexane to give the title compound as a white waxy solid, 1.528 g, 50%. $C_{36}H_{67}O_2Cl$ requires 566.6. Found ES⁻: (M−H⁺)⁻, 565.6. $\delta_H$ (CDCl₃) 1.27 (46H, br, C(CH₂)₂(CH₂)₈CH₂CH=CHCH₂(CH₂)₈CH₂CH=CHCH₂(CH₂)₇), 1.63 (2H, p, CH₂CH₂CO₂H), 1.76 (2H, p, CH₂CH₂Cl), 2.01 (8H, m, CH₂CH=), 2.34 (2H, t, CH₂CO₂H), 3.52 (2H, t, CH₂Cl), 5.34 (4H, m, CH=CH).

(E6) 36-Azidohexatriaconta-12,24-dienoic Acid

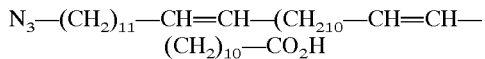

To E5 (1.528 g, 2.693 mmol) in anhydrous DMF (70 ml) was added sodium azide (1.226 g, 18.851 mmol) and the reaction heated for 5 days at 50° C. under argon. The solvent was reduced to almost dryness and the residues taken up into water (150 ml) and ethyl acetate (150 ml). The aqueous layer was further extracted with ethyl acetate (4×150 ml), the fractions combined, washed (2×150 ml water), dried (MgSO₄) and the solvent removed to quantitatively yield the title compound as a pale yellow waxy solid 1.465 g, 95%. $C_{36}H_{67}O_2N_3$ requires 573.5. Found ES⁻: (M−H₊)⁻, 572.6. $d_H$ (CDCl₃) 1.27 (46H, br, N₃(CH₂)₂(CH₂)₈CH₂CH=CHCH₂(CH₂)₈CH₂CH=CHCH₂(CH₂)₇), 1.63 (4H, m, CH₂CH₂N₃), CH₂H₂CO₂H), 2.02 (8H, m, CH₂CH=), 2.34 (2H, t, CH₂CO), 3.35 (2H, t, CH₂N₃), 5.35 (4H, m, CH=CH).

(E7) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-36-azidohexatriaconta-12,24-dienamide

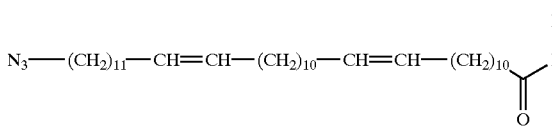

To E6 (299 mg, 0.521 mmol) in anhydrous dichloromethane (10 ml) were added EDC hydrochloride (200 mg, 1.043 mmol), N-hydroxysuccinimide (90 mg, 0.782 mmol) and the reaction left for 4 hours at room temperature. To the reaction were then added B21 (607 mg, 0.573 mmol) and triethylamine (211 mg, 2.085 mmol) in anhydrous dichloromethane (10 ml). The reaction was left for a further 3 hours and the solvent removed. The residues were purified by gradient silica chromatography eluting with 30–60% ethyl acetate in hexane to yield the title compound as a colourless viscous oil, 720 mg, 86%. $C_{91}H_{172}N_{10}O_{13}$ requires 1613.3. Found ES⁺: MH⁺, 1614.3, MH₂²⁺, 807.9. $\delta_H$ (CDCl₃) 1.27 (54H, br, N₃(CH₂)₂(CH₂)₈CH₂CH=CHCH₂(CH₂)₈CH₂CH=CHCH₂(CH₂)₇), (CH₂)₄CH), 1.35–1.80 (72H, m, (Me)₃C, CH₂CH₂N₃, CH₂CH₂CO, CH₂CH₂N), 2.00 (8H, m, CH₂CH=), 2.05 (1H, br, CH), 2.23 (2H, t, CH₂CO), 2.84 (6H, s, NMe), 2.95–3.35 (22H, m, CH₂N), 3.25 (2H, t, CH₂N₃), 5.34 (4H, m, CH=CH), 6.12 (1H, br, CONH).

(E8) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-36-aminohexatriacontanamide

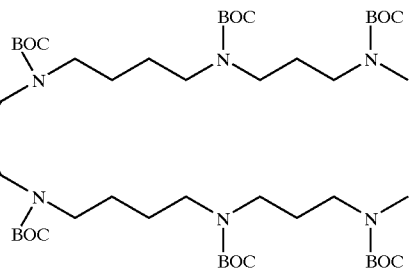

To E7 (184 mg) dissolved in tert-butanol at 40° C. was added Pd/C (50 mg) and the atmosphere changed to hydrogen. The hydrogenation was heated at 40° C. for 3 days, the catalyst filtered off and the solvent removed. The residues were purified by silica chromatography eluting initially with 100:10:0 CH₂Cl₂:MeOH:NH₄OH to remove faster running impurities then with 100:10:1 to remove the title compound as a colourless gum, 61 mg, 34%. $C_{91}H_{178}N_{813}$ requires 1591.3. Found ES⁺: MH⁺, 1592.3. $\delta_H$ (CDCl₃) 1.24 (72H, br, H₂N(CH₂)₂(CH₂)₃₂, CONH(CH₂)₂(CH₂)₄), 1.44 (66H, br, (Me)₃C, CH₂CH₂N), 1.72 (4H, p, NCH₂CH₂CH₂N), 1.98 (1H, br, CH), 2.14 (2H, t, CH₂CO), 2.67 (2H, t, CH₂NH₂), 2.83 (6H, s, NMe), 2.95–3.30 (22H, m, NCH₂), 5.62 (1H, br, CONH(CH₂)₆CH).

F. GLYCOAMINOLIPID SYNTHESES

This section contains the syntheses of:

(F4) 18-(Peracetylglucuronylamino)octadecanoic Acid

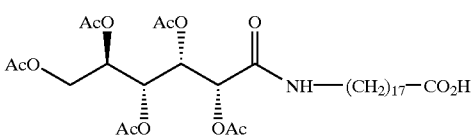

(F5) N-(Peracetylglucuronylaminoethyl)-4,8,13,17-tetramethyldodecanamic Acid

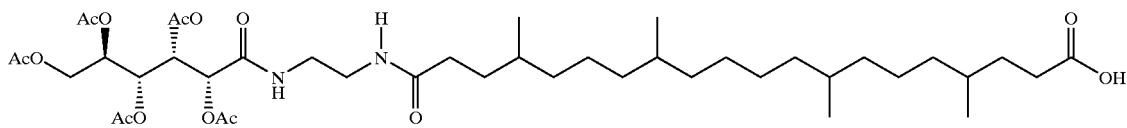

(F6) (12-(Peracetylglucuronylaminododecanoylamino)dodecanoic Acid

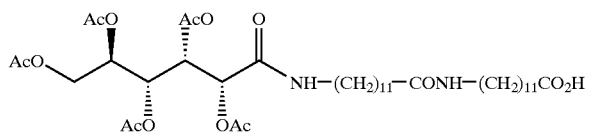

(F8) 12-(Peracetylglucuronylamino)dodecanoic Acid

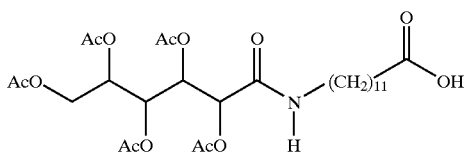

$C_{24}$ Glycoaminolipid

(F1) 24-(Glucuronylamino)tetracosanoic Acid

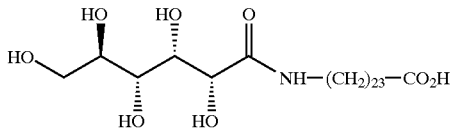

A suspension of D6 (792 mg, 2.064 mmol), d-gluconolactone (1.839 g, 10.32 mmol) and DBU (4.2 g, 30.9 mmol) in dry methanol (90 ml) were heated, at 60° C. for approximately 10 minutes until all solids had dissolved. The solution was left at room temperature overnight, then the solvent removed. The residues were taken up into water (5 ml) and acidified to pH 1 with 1M HCl to precipitate out the desired compound. This was filtered off and dried to yield the title compound as a white solid (765 mg, 66%). Silica tlc $R_f$ 0.35, ninhydrin negative (1:1:1 methanol:acetic acid:dichloromethane). I.R. 1581 $cm^{-1}$ ($CO_2^-$), 1639 $cm^{-1}$ (CONH). $\delta_H$ (DMSO) 1.32 (42H, br, $(CH_2)_{21}CH_2CO_2H$), 2.27 (2H, t, $CH_2CO_2H$), 3.15 (2H, m, $CH_2N$), 3.3–3.8 (4H, m, CHOH), 4.0–4.1 (2H, m, $CH_2O$).

(F2) 24-(Peracetylglucuronylamino)tetracosanoic Acid

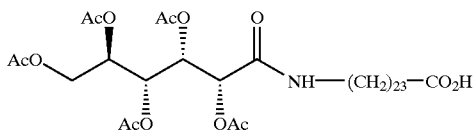

To F1 (765 mg, 1.362 mmol) dissolved in dry pyridine (20 ml) was added acetic anhydride (20 ml). The solution was stirred under argon overnight and water (50 ml) added slowly. The solution was extracted with dichloromethane and the dichloromethane then washed with HCl pH 3 (2×20 ml) and water (5×30 ml). The organics were dried ($MgSO_4$) and the solvent removed to yield the title compound as a white solid (940 mg, 89%). Alumina tlc $R_f$ 0.15 (15% methanol in dichloromethane). $C_{40}H_{69}NO_{13}$ requires 771.48. Found ES+: $MH^+$ 772.07, $MNa^+$ 794.25. ES-: $(M-H^+)^-$ 770.65. $\delta_H$ ($CDCl_3$) 1.26 (38H, br, $(CH_2)_{19}(CH_2)_2CO_2H$), 1.64 (4H, m, $CH_2CH_2CO_2H$, $CH_2CH_2NH$), 2.07, 2.11, 2.13, 2.21 (15H, s, MeCO), 2.35 (2H, t, $CH_2CO_2H$), 3.24 (2H, m, $CH_2NH$), 4.30 (2H, 2×d×d, $CH_2OAc$), 5.05 (1H, q, $CH(OAc)CH_2OAc$), 5.32 (1H, d, $CH(OAc)CONH$), 5.46 (1H, t, $CH(OAc)CH(OAc)CH_2OAc$), 5.70 (1H, t, $CH(OAc)CH(OAc)CONH$), 6.42 (1H, t, NH). $\delta_C$ ($CDCl_3$) 20.4, 24.5, 26.6, 28.8–29.5 (26C, $(CH_2)_{21}CH_2CO_2H$, MeCO), 33.8 (1C, $CH_2CO_2H$), 39.3 (1C, $CH_2NH$), 61.3 (1C, $CH_2OAc$), 68.5, 68.9, 69.1, 71.5 (4C, CHOAc), 165.8 (1C, CONH), 160.0, 169.5, 169.7, 170.4 (5C, MeCO), 178.6 (1C, $CO_2H$).

C18 Glycolipid

(F3) 18-(Glucuronylamino)octadecanoic Acid

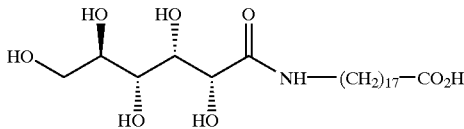

To a suspension of D10 (850 mg, 2.8 mmol) in methanol (100 ml) at 50° C. was added DBU (1.27 g, 8.4 mmol) When the aminoacid had dissolved d-gluconolactone (748 mg, 4.2 mmol) was added After 3 hrs no ninhydrin positive material was seen on tlc and the reaction was evaporated to dryness. Cold 0.5 M HCl was added and the resulting buff precipitate filtered off, washed with water and dried in vacuo to yield the title compound which was used without further purification.

(F4) 18-(Peracetylglucuronylamino)octadecanoic Acid

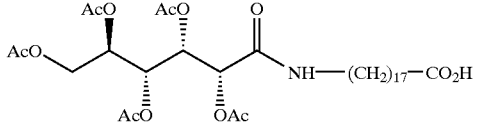

Crude F3 was dissolved in 50 ml 20% acetic anhydride in pyridine containing DMAP (100 mg). The reaction was left overnight, water added (10 ml) with cooling and evaporated to dryness. Dilute hydrochloric acid (50 ml. 0.5M) was added and the aqueous phase extracted with ethyl acetate The organic phase was dried ($MgSO_4$ and evaporated to dryness to give a brown tar. This material was dissolved in dichloromethane and chromatographed (Silica eluted with ethyl acetate in hexane (30% to 50%), all containing 0.1% acetic acid. Solvent removal yielded the title compound as a white solid (826 mg, 49% 2 steps). $C_{34}H_{56}NO_{13}$ requires C: 59.46%, H: 8.22%, N: 2.04%. Found: C: 59.24%, H: 8.35%, N: 1.97%. $C_{24}H_{49}NO_2$ requires 687. Found ES+: $MH^+$ 688. $\delta_H$ ($CD_3CO_2D$) 6.10 (1H, brt, CONH, 5.70 (1H, t, CH(OAc)CH(OAc)CONH), 5.45 (1H, t, CH(OAc)CH(OAc)CH—(OAc)CONH), 5.30 (1H, m, CH(OAc)CONH), 5.05 (1H, m $AcOCH_2$(OAc)CH), 4.31 (1H, dd[$J_1$=4 Hz, $J_2$=12 Hz]$AcOCH_2$(OAc), 4.13 (1H, dd[$J_1$=6 Hz, $J_2$=12 Hz]$AcOCH_2$(OAc), 3.22 (2H, m, $NCH_2$), 2.33 (2H, t, $CH_2CO_2H$), 2.0–2.25 (15H, 5xs, acetate), 1.61 (2H, t, $NCH_2CH_2$), 1.45 (1H, t, $CH_2CH_2CO_2H$), 1.25 (26H, s, $CH_2$).

Reduced Bixin Glycolipid (F5) N-(Peracetylglucuronylaminoethyl)-4,8,13,17-tetramethyldodecanamic Acid

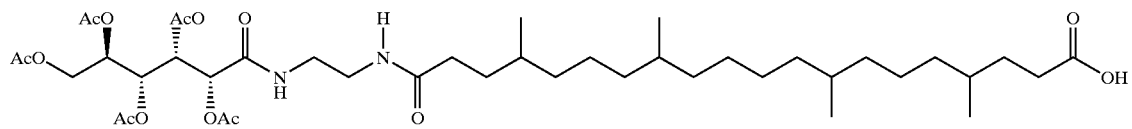

D15 (4.91 g, 11.1 mmol) was dissolved in methanol (50 ml) containing DBU (5.02 ml, 33.6 mmol). α-Gluconolactone (2.4 g, 13.3 mmol) was added to the stirred solution, which was left at room temperature for 5 hrs. The reaction was evaporated to dryness and 10% cold citric acid added (50 ml). The precipitant was kept cold whilst it was filtered off and washed with cold water. The step can be slow. The solid was dried in vacuo then dissolved in pyridine and dried by evaporation of solvent. The residue was dissolved in pyridine (100 ml) containing acetic anhydride (20 ml) and DMAP (200 mg) and left stirring overnight. Water was added (30 ml) with cooling and the reaction evaporated to dryness. The resulting black tar was chromatographed (silica, 30% ethyl acetate in hexane containing 0.1% acetic acid) to yield the title compound as a glassy solid (1.83 g, 20%). $C_{42}H_{72}N_2O_{14}$ requires 828. Found ES+: $MH^+$ 829. $d_H$ ($CD_3CO_2D$) 7.1 (1H, brt, CONH), 6.17 (1H, brt, CONH), 5.60 (1H, t, CH(OAc)CH(OAc)CONH), 5.41 (1H, t, CH(OAc)CH(OAc)CH(OAc)CONH), 5.24 (1H, m, CH(OAc)CONH), 5.02 (1H, m, $AcOCH_2$(OAc)CH), 4.29 (1H, dd[$J_1$=4 Hz, $J_2$=12 Hz]$AcOCH_2$(OAc), 4.11 (1H, dd[$J_1$=6 Hz, $J_2$=12 Hz]$AcOCH_2$(OAc), 3.2–3.62 (4H, m, $NCH_2$), 2.33–0.8 (57H, mm, $CH_2$ & $CH_3$).

C24 Amide Containing Glycolipid (F6) (12-(Peracetylglucuronylaminododecanoylamino)dodecanoic Acid

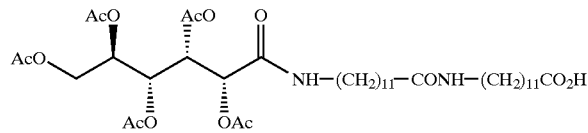

D18 (2.12 g, 5.1 mmol) was dissolved in methanol (50 ml) containing DBU (2.3 ml, 15.3 mmol). d-gluconolactone (1.09 g, 6.12 mmol) was added to the stirred solution, which was left at room temperature for 3 hrs. The reaction was evaporated to dryness & 10% cold citric acid added (50 ml). The precipitant was kept cold whilst it was filtered off and washed with cold water. This step can be slow. The solid was dried in vacuo then dissolved in pyridine and dried by evaporation of solvent. The residue 15 was dissolved in pyridine (100 ml) containing acetic anhydride (20 ml) & DMAP (200 mg) and left stirring overnight. Water was added (30 ml) with cooling and the reaction evaporated to dryness. Dilute hydrochloric acid (1M, 100 ml) was added and the aqueous phase extracted with dichloromethane, dried and evaporated to dryness. The resulting black tar was chromatographed (silica, 5% methanol in dichloromethane) to yield the title compound as a glass (2.44 g, 53%). $C_{40}H_{68}N_2O_{14}$ requires 800. Found ES+: $MH^+$ 801. $\delta_H$ ($CDCl_3$) 7.1 (1H, brt, CONH), 5.68 (1H, br, CONH), 5.66 (1H, t, CH (OAc)CH(OAc)CONH), 5.43 (1H, t, CH(OAc)CH(OAc)CH(OAc)CONH), 5.29 (1H, m, CH(OAc)CONH), 5.04 (1H, m, $AcOCH_2$(OAc)CH), 4.33 (1H, dd[$J_1$=4 Hz, $J_2$=12 Hz]$AcOCH_2$(OAc), 4.15 (1H, dd[$J_1$=6 Hz, $J_2$=12 Hz]$AcOCH_2$(OAc), 3.27–3.18 (4H, m, $NCH_2$), 2.33 (2H, t, $CH_2CO$), 2.19–2.04 (2H+15H, t+5s, $CH_2CO$+ acetates), 1.6–1.1 (36H, tm, $CH_2$).

(F7) 12-(Glucuronylamino)dodecanoic Acid

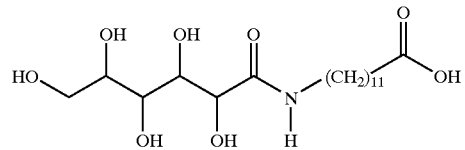

To a solution of d-gluconolactone (1.654 g, 9.288 mmol) in dry methanol (50 ml) under argon was added 12-aminolauric acid (2.000 g, 9.288 mmol) in dry methanol (50 ml), followed by dry triethylamine (9.398 g, 92.88 mmol). The solution/suspension was heated at 80° C. for two hours until all solids dissolved then left at room temperature overnight. Removal of the solvent yielded the desired product as a white insoluble powder, a suspension of which was washed in water (100 ml) at 90° C. for two hours. Filtration and subsequent drying under vacuum yielded the title compound (3.817 g, 83%) as a pure white solid. I.R. 1561 $cm^{-1}$ ($CO_2^-$), 1626 $cm^{-1}$ (CONH, $CO_2^-$). $\delta_H$ ($CD_3OD$) 1.0–1.7 (18H, br m, $(CH_2)_9CH_2CO_2$), 2.11 (2H, t, $CH_2CO_2$), 3.20 (2H, t, $CH_2N$), 3.5–3.9 (4H, m, $CH_2OH$), 4.05, 4.25 (2H, 2xbr, $CH_2OH$). $d_C$ ($CD_3OD$) 11.6, 29.4, 32.0 (9C, $(CH_2)_9CH_2CO_2$), 41.0, 42.5 (2C, $CH_2NH$, $CH_2CO_2$), 66.0 (1C, $CH_2OH$), 73.7, 74.4, 75.6, 76.8 (4C, CHOH).

(F8) 12-(Peracetylglucuronylamino)dodecanoic Acid

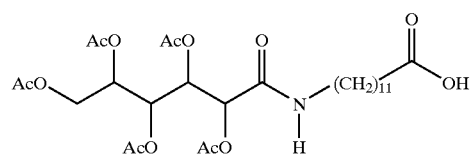

To F7 (1.739 g, 3.515 mmol) dissolved in dry pyridine (10 ml) under argon was added acetic anhydride (10 ml). The solution was left overnight at room temperature and water (10 ml) slowly added to decompose any anhydride. The solution was extracted exhaustively with dichloromethane and this organic fraction washed (4×20 ml HCl, pH3, and 4×20 ml water), dried (MgSO$_4$) and the solvent removed to quantitatively yield the title compound as a pale yellow solid/gum, alumina tlc r.f. 0.1 (10% methanol in dichloromethane). C$_{28}$H$_{45}$NO$_{13}$ requires. 603.29. Found ES+: MH$^+$ 604.31, ES−: (M−H$^+$)$^-$ 602.37. $\delta_H$ (CDCl$_3$) 1.08 (15H, br, Me), 1.27, 1.42 (4H, 2×m, (CH$_2$)$_2$(CH$_2$)$_4$ $\delta_H$ (CDCl$_3$) 1.08 (15H, br, Me), 1.27, 1.42 (4H, 2×m, (CH$_2$)$_2$(CH$_2$)$_4$CO$_2$H), 1.75–2.05 (14H, br, (CH$_2$)$_4$(CH$_2$)$_2$(CH$_2$)$_3$CO$_2$H), 2.14 (2H, m, CH$_2$CO$_2$H), 3.00 (2H, t, CH$_2$NH), 3.90–4.15 (2H, br, CH$_2$O), 4.90, 5.11, 5.26, 5.48 (4H, 4×br, CHO), 6.95 (1H, NHCO). $\delta_C$ (CDCl$_3$) 19.6, 19.9 (5C, Me), 24.1, 26.1, 28.3, 28.5, 28.6, 28.7, 28.8, 33.3 (9C, (CH$_2$)$_9$CH$_2$CO$_2$H), 38.9 (1C, CH$_2$CO$_2$H), 53.1 (1C, CH$_2$N), 60.8 (1C, CH$_2$O), 68.1, 68.4, 68.7, 71.3 (4C, CHO), 165.8 (1C, CONH), 168.6, 169.1, 169.2, 169.9, 170.0 (5C, COMe), 176.7 (1C, CO$_2$H).

G. TWO LIPID CHAIN SYNTHESES

This section contains the synthesis of:

(G4)(RS)-N-{1-[8-aminobutylamino-7-aminobutylaminomethyl)octylaminocarbonyl)-2-(peracetylglucuronylaminotetracosanoylamino)ethyl}-24-(peracetylglucuronylamino)tetracosanamide tetra(Trifluoroacetate) Salt To F2 (250 mg, 0.324 mmol) dissolved in anhydrous dichloromethane (10 ml) were added EDC hydrochloride (68 mg, 0.356 mmol) and N-hydroxysuccinimide (41 mg, 0.356 mmol) and the reaction left overnight under argon at room temperature. To this was added a solution of 2,3 diaminopropionic acid hydrochloride (228 mg, 0.162 mmol) and DBU (148 mg, 0.972 mmol) and the reaction stirred rapidly overnight. The solvent was removed and the residues taken up into hot water (20 ml).

The solution was allowed to cool and acidified to pH 1 with 1M HCl. The resulting precipitate was filtered off, washed with water and dried under vacuum to yield the title compound as a buff coloured precipitate (249 mg, 92%). C$_{83}$H$_{142}$N$_4$O$_{26}$ requires 1611.0. Found ES$^+$: MNa$^+$, 1633.4, MH$^+$, 1611.6, ES$^-$ (M−H$^+$)$^-$ 1609.6. $\delta_H$ (CDCl$_3$) 1.24 (76H, br, (CH$_2$)$_{19}$(CH$_2$)$_2$CO), 1.46 (4H, p, CH$_2$CH$_2$CO), 1.62 (4H, br, CH$_2$CH$_2$N), 2.04–2.19 (30H, m, MeCO), 2.24 (4H, m, CH$_2$CO), 3.23 (4H, m, CH$_2$N), 3.45, 3.85 (2H, 2×m, CHCH$_2$N), 4.12, 4.31 (4H, 2×m, CH$_2$OAc), 4.38 (1H, m, CHCO$_2$), 5.04 (2H, q, CHOAcCH$_2$OAc), 5.28 (2H, d,

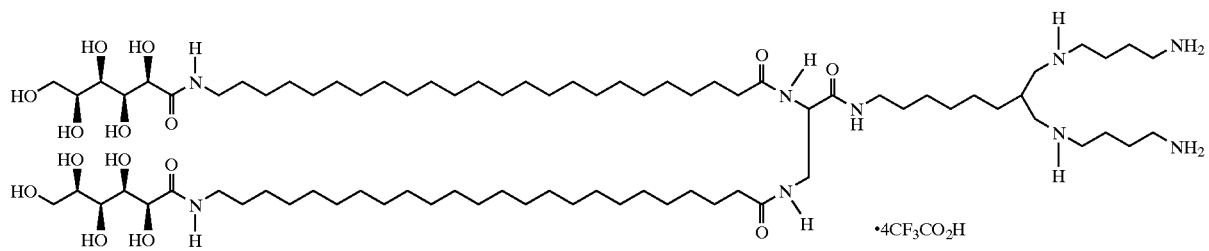

(G1) (RS)-2,3-bis(Peracetylglucuronylaminotetracosanoylamino)propanoic Acid

CHOAcCONH), 5.43, 5.66 (4H, 2×t, (CHOAc)$_2$CHOAcCH$_2$OAc), 6.09 (2H, t, CONH(CH$_2$)$_{23}$), 6.65 (1H, t, CH$_2$NHCO(CH$_2$)$_{23}$), 7.76 (1H, d, CONHCHCO$_2$H).

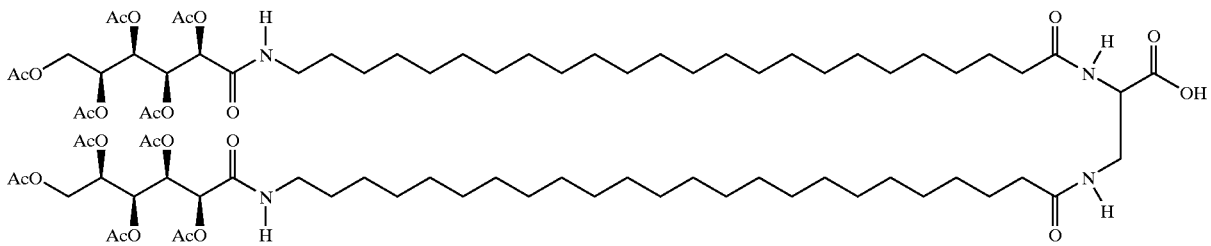

(G2) (RS)-N-(1-{8-[t-butyloxycarbonylaminobutyl
(t-butyloxycarbonyl)amino]-7-[t-
butyloxycarbonylaminobutyl(t-butyloxycarbonyl)
aminomethyl]octylaminocarbonyl}-2-
(peracetylglucuronylaminotetracosanoylamino)
ethyl)-24-(peracetylglucuronylamino)
tetracosanamide

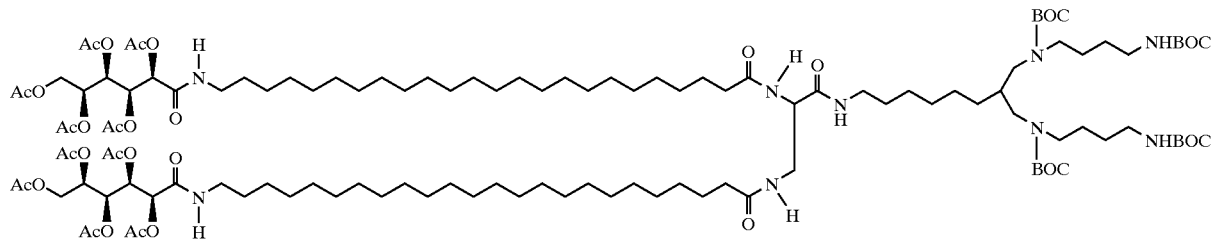

To G1 (240 mg, 0.149 mmol) in anhydrous dichloromethane (20 ml) were added EDC hydrochloride (40 mg, 0.208 mmol) and N-hydroxysuccinimide (19 mg, 0.164 mmol) and the reaction left overnight under argon at room temperature. To this was added B8 (112 mg, 0.156 mmol) and triethylamine (90 mg, 0.893 mmol) and the reaction left for a further five hours. The solvent was removed and the residues purified by silica column chromatography (80% ethyl acetate in hexane) to yield the title compound (163 mg, 47%) as a colourless solid. $C_{120}H_{213}N_9O_{33}$ requires 2308.5. Found ES$^+$: MHNa$^{2+}$, 1167.5, MNa$_2^{2+}$, 1177.5. $\delta_H$ (CDCl$_3$) 1.24 (84H, br, $(CH_2)_{19}(CH_2)_2CO$, $(CH_2)_4CH$), 1.43 (54H, m, $CH_2CH_2N$, $C(Me)_3$, $CH_2CH_2CO$), 2.0 (1H, br, CH), 2.0–2.3 (30H, m, MeCO), 2.24 (4H, m, $CH_2CO$), 2.95–3.35 (18H, m, $CH_2N$), 3.45–3.80 (2H, m, $CHCH_2$), 4.14.35 (4H, m, $CH_2OAc$), 4.40 (1H, m, $CHCH_2N$), 5.03 (2H, q, CHOAcCH$_2$OAc), 5.16 (2H; d, CHOAcCO), 5.44, 5.54 (4H, 2×t, (CHOAc)$_2$CHOAcCO), 6.10 (3H, br, CHCONH, NHCOCHOAc), 7.45, 7.60 (2H, 2×br, CONHCHCH$_2$NHCO).

(G3) (RS)-N-(1-{8-[t-butyloxycarbonylaminobutyl
(t-butyloxycarbonyl)amino]7-[t-
butyloxycarbonylaminobutyl(t-butyloxycarbonyl)
aminomethyl]octylaminocarbonyl}-2-
(glucuronylaminotetracosanoylamino)ethyl)-24-
(glucuronylamino)tetracosanamide

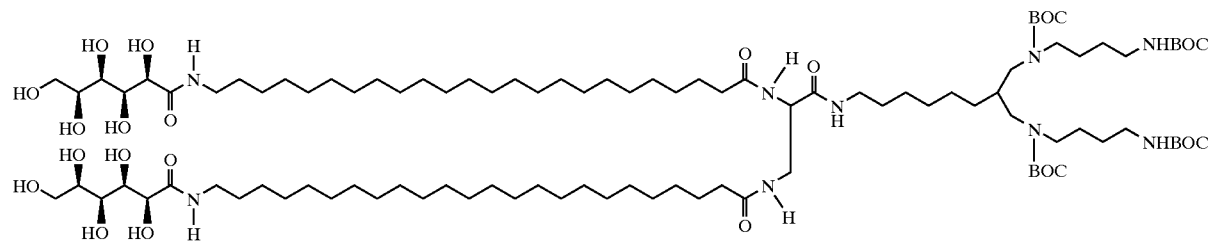

To G2 (163 mg) dissolved in methanol (30 ml) was added concentrated ammonium hydroxide until the solution started to become cloudy (approximately 3 ml). The reaction was left for three hours but had not given total deacetylation and was precipitating out of solution. The solvent was removed, the residues taken up into 2:1 dichloromethane:methanol (60 ml) with heating and concentrated ammonium hydroxide added until the solution started to become cloudy (approx 10 ml). The reaction was left for a further six hours and the solvents removed to yield the title compound as an off white solid too insoluble for analysis and used crude in the next step.

(G4) (RS)-N-{1-[8-aminobutylamino-7-(aminobutylaminomethyl)octylaminocarbonyl)-2-(peracetylglucuronylaminotetracosanoylamino)ethyl}-24-(peracetylglucuronyl-amino)tetracosanamide tetra(Trifluoroacetate) Salt

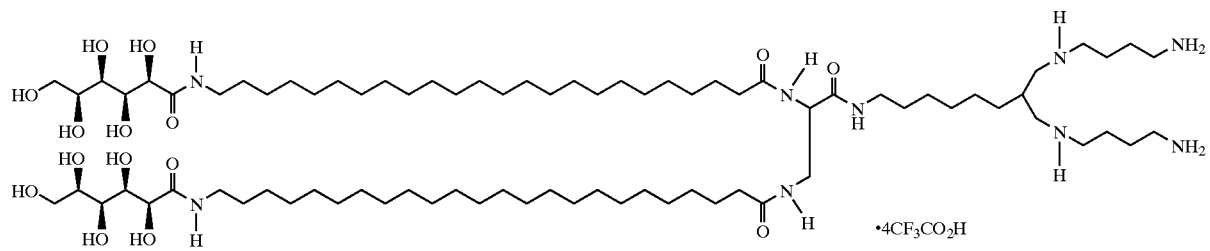

G3 (120 mg) was dissolved in 96:4 trifluoroacetic acid:dichloromethane. (8 ml) and left for 20 minutes at room temperature. The solvent was removed, the residues taken up into water, filtered (0.45 mm polypropylene) and freeze dried to give the title compound as a pale yellow solid (126 mg). $C_{80}H_{161}N_9O_{15}$ requires 1488.2. Found ES$^+$: $MH_2^{2+}$, 745.4, MH$^+$, 1489.3. $\delta_H$ (D$_2$O) 1.7–2.25 (94H, br, (CH$_2$)$_{21}$CH$_2$CO, (CH$_2$)$_5$CH), 2.38 (8H, br, NCH$_2$(CH$_2$)$_2$CH$_2$N), 2.80 (5H, br, CH, CH$_2$CO), 3.65–3.95 (18H, m, NCH$_2$), 4.11 (2H, br, CHCH$_2$NH), 4.2–4.5 (8H, m, CHOH), 4.6 (1H, m, COCHNH), 4.7, 4.85 (4H, 2×br, CH$_2$OH).

H. SYNTHESES OF PROTECTED & UNPROTECTED CARBOHYDRATE LIPID TETRAMINES AND HEXAMINES

This section contains the syntheses of:

Carbohydrate Lipid Tetramines (H3) N-[8-(aminobutylamino)-7-(aminobutylaminomethyl)octyl]-24-(glucuronylamino)tetracosanamide tetra (Trifluoroacetate) Salt

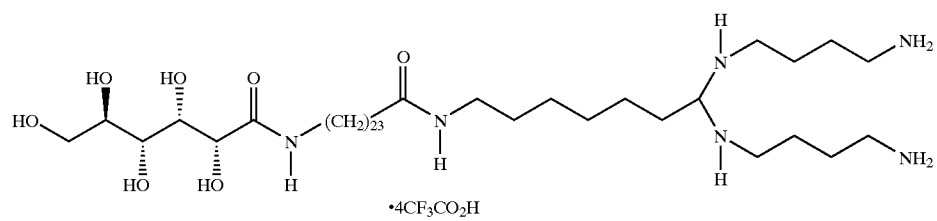

(H6) N-[8-(Aminobutylamino)-7-
(aminobutylaminomethyl)octyl]-18-
(glucuronylamino)octadecanamide tetra
(Trifluoroacetate) Salt

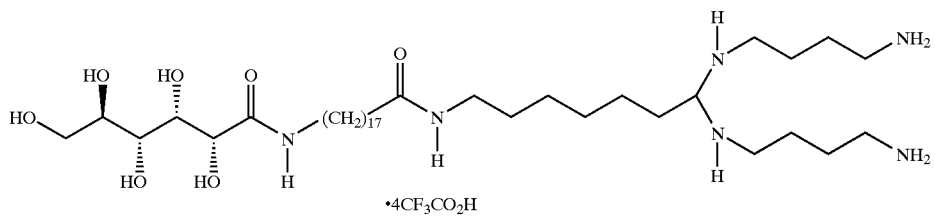

(H12) N-[8-Aminobutylamino-7-(Aminobutylamin-
o-methyl)octyl]-18-
(glucuronylaminododecanoylamino)dodecanamide
tetra(Trifluoroacetate) Salt

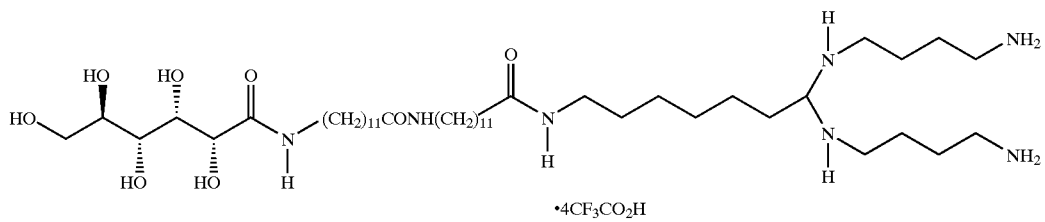

(H9) N-[8-(aminobutylamino)-7-
(aminobutylaminomethyl)octyl]-N'-
(glucuronylaminoethyl)-4,8,13,17-tetramethyl-1,20-
docosadiamide tetra(Trifluoroacetate) Salt

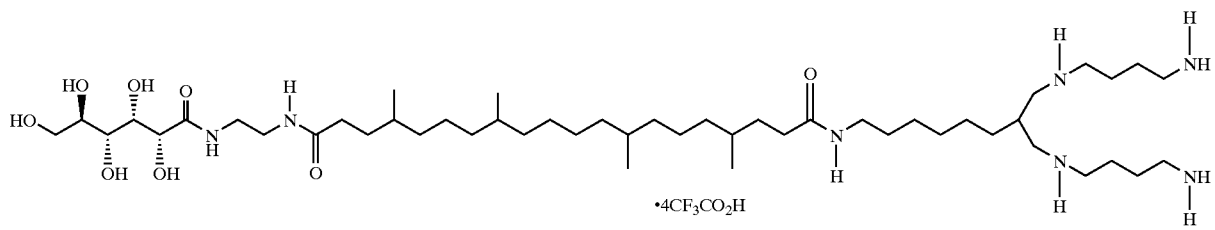

(H15) N-[8-(Aminobutylamino)-7-
(aminobutylaminomethyl)
octylaminocarbonyltricosanyl]-N,N'-bis
(glucuronylaminoethyl)succinamide tetra
(Trifluoroacetate) Salt

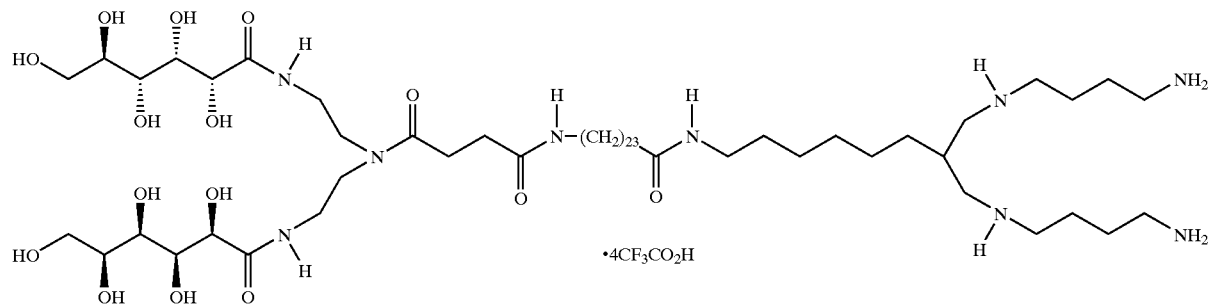

Carbohydrate Lipid Hexamines (H18) N-[8-(Aminopropylaminobutylamino)-7-(aminopropylaminobutylaminomethyl)octyl]-24-(glucuronyl-amino)tetracosanamide hexa (Trifluoroacetate) Salt

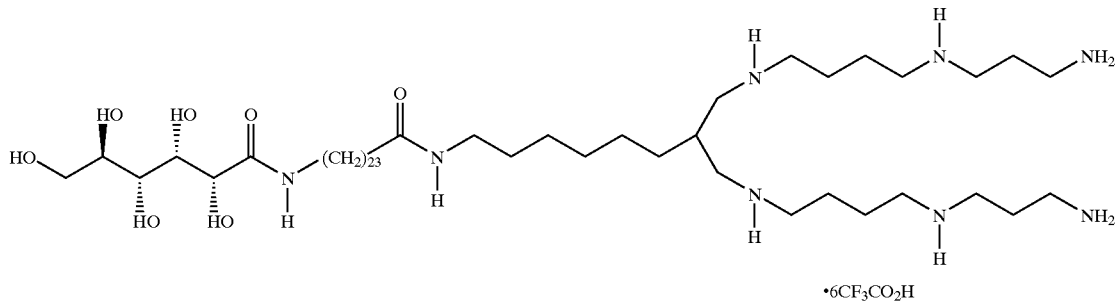

(H21) N-[8-(aminopropylaminobutylamino)-7-(aminopropylaminobutylaminomethyl)octyl]-18-(glucuronylamino)octadecanamide hexa (Trifluoroacetate) Salt

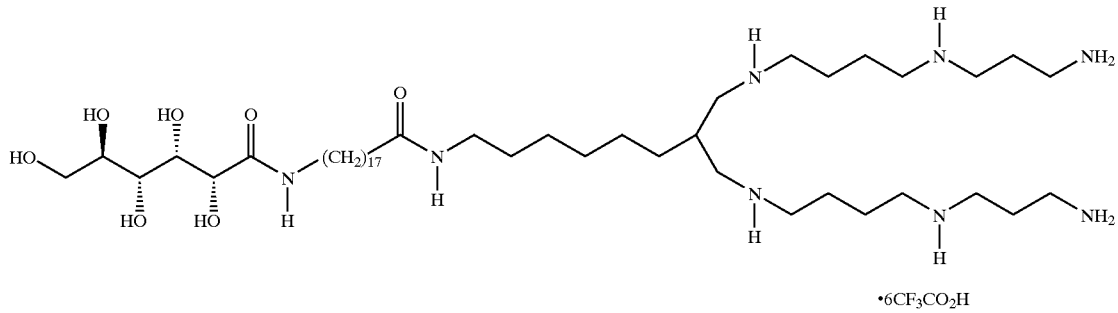

(H24) N-[8-(aminopropylaminobutylamino)-7-(aminopropylaminobutylaminomethyl)octyl]-N'-(glucuronylaminoethyl)-4,8,13,17-tetramethyl-1,20-docosadiamide hexa(Trifluoroacetate) Salt

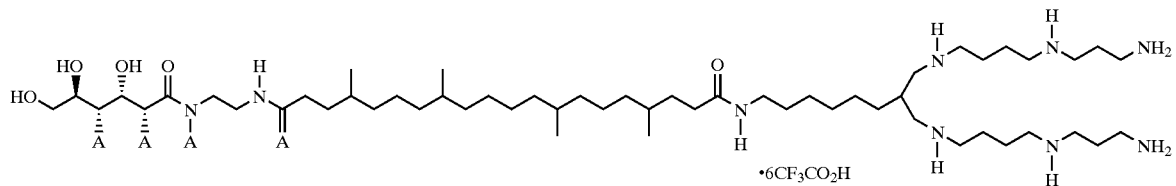

(H27) N-[8-(Aminopropylaminobutylamino)-7-(aminopropylbutylaminomethyl)octyl]-12-(glucuronylaminododecanoylamino)dodecanamide hexa(Trifluoroacetate) Salt

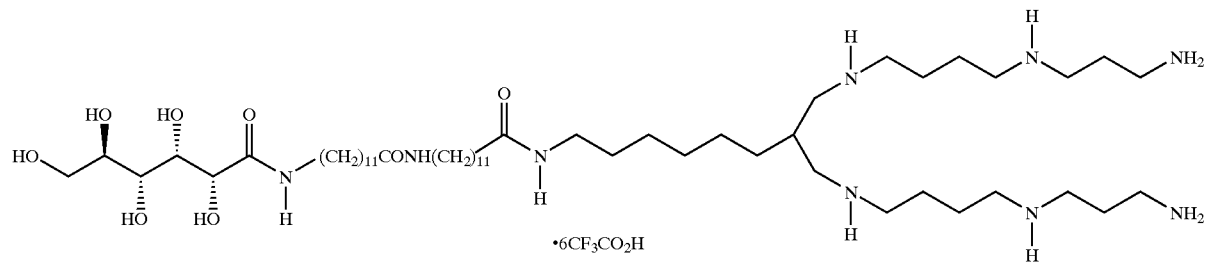

(H20) N-[8-(Methylaminopropylaminobutylamino)-
7-(methylaminopropylaminobutylaminomethyl)
octylaminocarbonyltricosanyl}-N',N'-bis
(glucuronylaminoethyl)succinamide

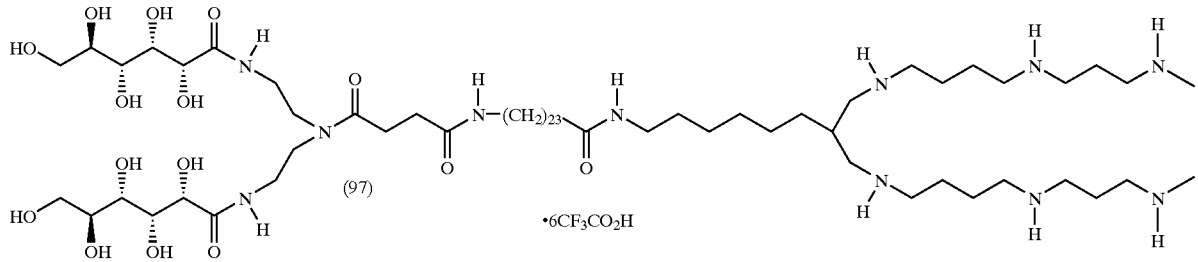

(H33) N-[8-(Methylaminopropylaminobutylamino)-
7-(methylaminopropylaminobutylaminomethyl)
octyl]-24-(glucuronylamino)tetracosanamide

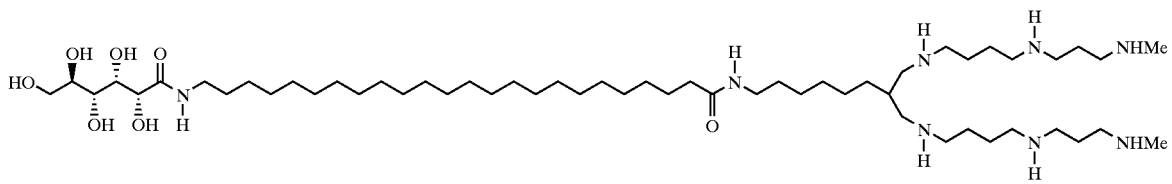

(H36) N-[8-(Methylaminopropylaminobutylamino)-
7-methylaminopropylaminobutylaminomethyl)
octyl]-24-glucuronylaminododecanoylamino)
tetracosanamide

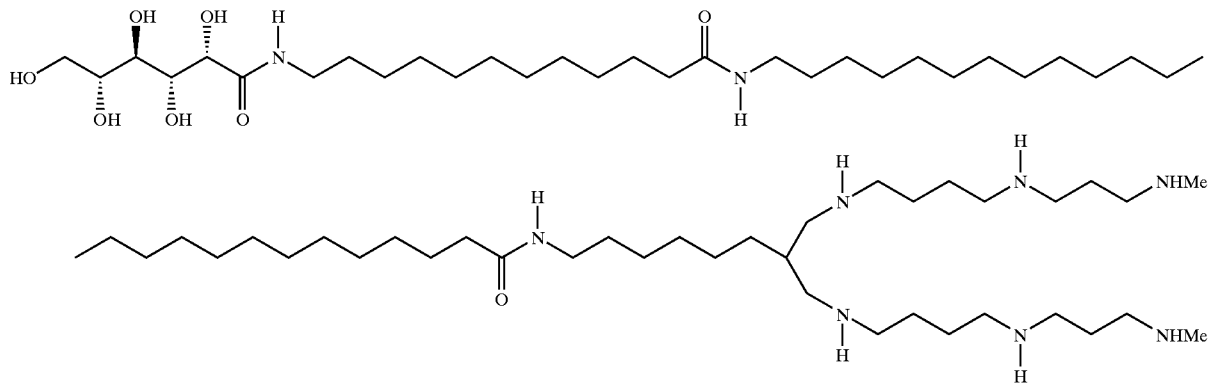

(H38)

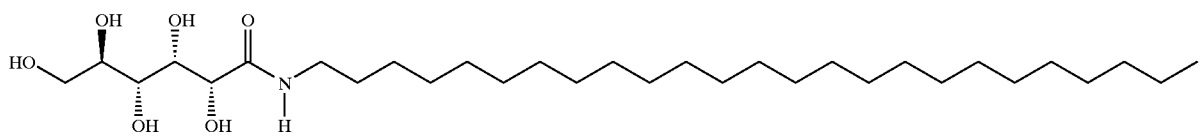

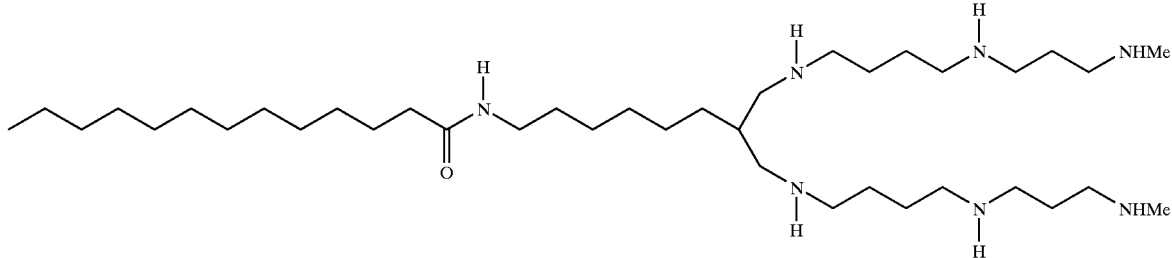

Carbohydrate Lipid Tetramines

C24 Tetramine (H1) N-{8-[t-Butyloxycarbonylaminobutyl(t-butyloxycarbonyl)amino]-7-[t-Butyloxycarbonylaminobutyl(t-butyloxycarbonyl)aminomethyl]octyl}-24-(peracetylglucuronylamino)tetracosanamide

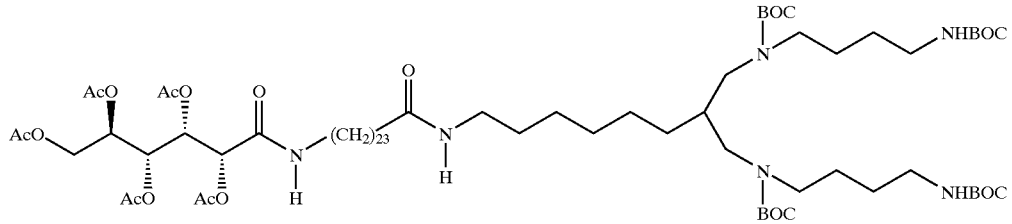

N-Methylmorpholine (0.12 ml, 1.1 mmol) was added to a stirred solution of F2 (0.771 mg, 1mmol) in dry dichloromethane (10 ml) at room temperature under argon. After a few minutes N-hydroxysuccinimide (127 mg, 1.1 mmol) was added followed by EDC (270 mg, 1.4 mmol), the reaction was stirred overnight (tlc showed conversion to the active ester). A solution of B8 (860 mg, 1.3 mmol) and triethylamine (0.7 ml, 5.5 mmol) in dry dichloromethane (5 ml) was added dropwise and stirring continued for two hours. Tlc showed the active ester had been converted to a slower moving product (silica—60% ethyl acetate in hexane). The solvent was removed and the product chromatographed (silica—60% ethyl acetate in hexane) to yield the title compound (1.25 g, 70%). $C_{77}H_{140}N_6O_{20}.H_2O$ requires C: 62.53%, H: 9.54%, N: 5.61%. Found: C: 62.53%, H: 9.52%, N: 5.69%. $C_{77}H_{140}N_6O_{20}$ requires 1469. Found ES+: MH+ 1470. $\delta_H$ (CDCl$_3$) 6.07 (1H, brt, CONH), 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m AcOCH$_2$(OAc)CH), 4.31 (1H, dd[J$_1$=4 Hz, J$_2$=12 Hz]AcOCH$_2$(OAc), 4.13 (1H, dd[J$_1$=6 Hz, J$_2$=12 Hz]AcOCH$_2$(OAc), 2.9–3.4 (16H, m, NCH$_2$), 2.0–2.3 (17H, m, CH$_2$CO), 1.2–1.7 (96H, dm, CH$_2$), (H2) N-{8-[t-Butyloxycarbonylaminobutyl(t-butyloxycarbonyl)-amino]-7-[t-Butyloxycarbonylaminobutyl(t-butyloxycarbonyl)aminomethyl]octyl}-24-(glucuronylamino)tetracosanamide

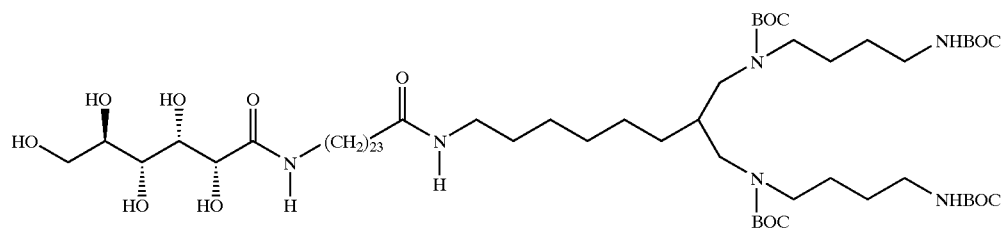

A solution of potassium carbonate (431 mg, 3.12 mmol) in water (2 ml) was added dropwise to a stirred solution of H1 (905 mg, 0.61 mmol) in methanol (15 ml) at room temperature. The flask was stirred for 20 min whereupon tlc showed no starting material was present. Water was added and the precipitate filtered, washed and dried. The product was purified by chromatography (silica—15% methanol in dichloromethane) to yield the title compound (445 mg, 57%). $C_{67}H_{130}N_6O_{15}$ requires 1259. Found ES+: MH+ 1260. $\delta_H$(CD$_3$OD) 3.6–4.2 (6H, m, sugar), 3.0–3.4 (16H, m, CH$_2$N), 2.15 (3H, t, CH$_2$CO), 2.05 (1H, m, CH$_2$CH(CH$_2$)$_2$), 1.2–1.7 (96H, m, CH$_2$).

(H3) N-[8-(Aminobutylamino)-7-(aminobutylaminomethyl)octyl]-24-(glucuronylamino)tetracosanamide tetra (Trifluoroacetate) Salt

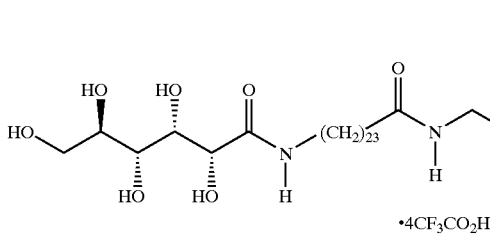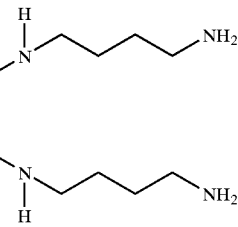

A solution of the H2 (445 mg, 0.353 mmol) in 96% TFA (4% water) was stirred for 30 mins at room temperature. The TFA was removed under vacuum, and traces removed by evaporation of water. The title compound was obtained as a colourless solid by lyophilisation. 400 mg, 86%. $C_{55}H_{102}N_6O_{15}F_{12} \cdot 1.6H_2O$ requires C: 46.95%, H: 7.34%, N: 5.76%. Found: C: 46.99%, H: 7.17%, N: 5.82%. The free base $C_{47}H_{98}N_6O_7$ requires 858.7. Found ES+: MH+ 859.7. $\delta_H$ (CD$_3$OD) 3.6–4.2 (6H, m, sugar), 3.0–3.4 (16H, m, CH$_2$N), 2.0–2.2 (2H, t, CH$_2$CO), 1.2–1.7 (96H, m, CH$_2$).

C18 Tetramine

(H4) N-{8-[t-Butyloxycarbonylaminobutyl(t-butyloxycarbonyl)amino]-7-[t-Butyloxycarbonylaminobutyl(t-butyloxycarbonyl)aminomethyl]octyl}-18-(peracetylglucuronylamino)octadecanamide

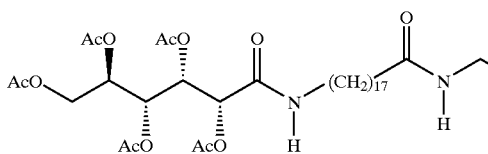

N-Methylmorpholine (0.12 ml, 1.1 mmol) was added to a stirred solution of F4 (687 mg, 1 mmol) in dry dichloromethane (20 ml) at room temperature under argon. A few minutes later N-hydroxysuccinimide (127 mg, 1.1 mmol) was added followed by EDC (270 mg, 1.4 mmol), the reaction was stirred overnight (tlc showed conversion to the active ester). A solution of B8 (394 mg, 0.55 mmol) and triethylamine (0.35 ml, 5.5 mmol) in dry dichloromethane (4 ml) was added dropwise and stirring continued for two hours. Tlc showed the active ester had been converted to a slower moving product (silica—60% ethyl acetate in hexane). The solvent was removed and the product chromatographed (silica—60% to 80% ethyl acetate in hexane) to yield the title compound (533 mg, 80%). $C_{61}H_{128}N_6O_{15} \cdot 213H_2O$ requires C: 61.01%, H: 9.33%, N: 6.01%. Found: C: 61.05%, H: 9.32%, N: 5.87%. $C_{61}H_{128}N_6O_{20}$ requires 1384.9. Found ES+: MH+ 1386.3. $\delta_H$ (CDCl$_3$) 6.07 (1H, brt, CONH), 5.85 (1H, br, CONH), 5.67 (1H, t, CH (OAc)CH(OAc)CONH), 5.43 (1H, t, CH(OAc)CH(OAc)CH(OAc)CONH), 5.30 (1H, m, CH(OAc)CONH), 5.05 (1H, m AcOCH$_2$(OAc)CH), 4.65 (2H, br, 2×NH), 4.31 (1H, dd[J$_1$=4 Hz, J$_2$=12 Hz]AcOCH$_2$(OAc), 4.13 (1H, dd[J$_1$=6 Hz, J$_2$=12 Hz]AcOCH$_2$(OAc), 2.9–3.4 (16H, m, NCH$_2$), 2.0–2.3 (17H, m, MeCO+CH$_2$CO), 1.2–1.7 (84H, dm, CH$_2$),

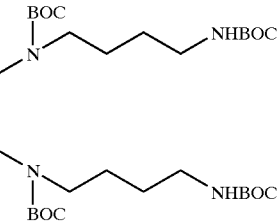

(H5) N-{8-[t-Butyloxycarbonylaminobutyl(t-butyloxycarbonyl)amino]-7-[t-butyloxycarbonylaminobutyl(t-butyloxycarbonyl)aminomethyl]octyl}-18-(glucuronylamino)octadecanamide

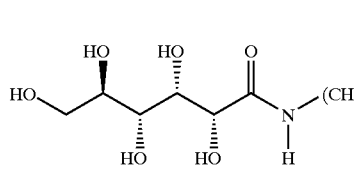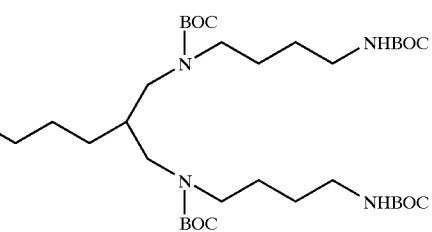

A solution of potassium carbonate (207 mg, 1.5 mmol) in water (1 ml) was added dropwise to a stirred solution of H4 (415 mg, 0.3 mmol) in methanol (12 ml) at room temperature. The flask was stirred for 30 mins whereupon tlc showed no starting material was present. Amberlite CG50 (4 g wet) was added and the resin filtered, washed with methanol and dried. The product was purified by chromatography (silica—10% methanol in dichloromethane) to yield the title compound (190 mg, 54%). $C_{61}H_{118}N_6O_{15} \cdot 3/5H_2O$ requires C: 61.75%, H: 10.13%, N: 7.081%. Found: C: 61.755%, H: 10.06%, N: 6.95%. $C_{61}H_{118}N_6O_{15}$ requires 1174.9. Found

Bixin Tetramine (H7) N-{8-[t-Butyloxycarbonylaminobutyl(t-butyloxycarbonyl)amino]-7-[t-butyloxycarbonylaminobutyl(t-butyloxycarbonyl)aminomethyl]octyl}-N'-(peracetylglucuronylaminoethyl)-4,8,13,17-tetramethyl-1,20-docosadiamide

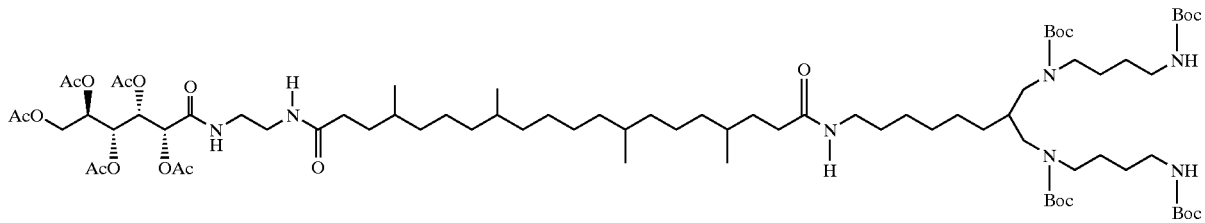

ES+: MH+ 1176.0. $\delta_H$ (CD$_3$OD) 3.6–4.2 (6H, m, sugar), 3.0–3.4 (16H, m, CH$_2$N), 2.15 (2H, t, CH$_2$CO), 2.06 (1H, m, CH$_2$CH(CH$_2$)$_2$), 1.2–1.7 (84H, m, CH$_2$).

(H6) N-[8-(Aminobutylamino)-7-(aminobutylaminomethyl)octyl]-18-(glucuronylamino)octadecanamide tetra (Trifluoroacetate) Salt N-Methylmorpholine (0.16 ml, 1.47 mmol) was added to a stirred solution of F5 (1.04 g, 1.33 mmol) in dry dichloromethane (20 ml) at room temperature under argon. A few minutes later N-hydroxysuccinimide (170 mg, 1.47 mmol) was added followed by EDC (282 mg, 1.47 mmol), the reaction was stirred overnight (tlc showed conversion to the active ester). A solution of B8 (520 mg, 1.47 mmol) and triethylamine (0.46 ml, 3.35 mmol) in dry dichloromethane (10 ml) was added dropwise and stirring continued for two hours. Tlc showed the active ester had been converted to a slower moving product (silica—60% ethyl acetate in hexane). The solvent was removed and the product chromatographed (silica—5% methanol in dichloromethane) to

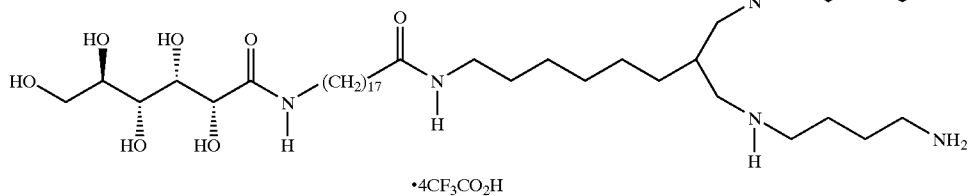

•4CF$_3$CO$_2$H

A solution of H5 (190 mg, 0.16 mmol) in 96% TFA (4% water) was stirred for 30 mins at room temperature. The TFA was removed under vacuum, and traces removed by evaporation of water. The title compound was obtained as a colourless hygroscopic solid (190 mg, 95%) by lyophilisation. $C_{49}H_{90}N_6O_{15}F_{12} \cdot 2H_2O$ (Mwtanhydrous=1230) requires C: 46.95%, H: 7.34%, N: 5.76%. Found: C: 46.99%, H: 7.17%, N: 5.82%. The free base $C_{41}H_{86}N_6O_7$ requires 774. Found ES+: MH+ 775. $\delta_H$ (CD$_3$OD) 3.6–4.25 (6H, m, sugar), 2.9–3.4 (16H, m, CH$_2$N), 2.15 (2H, t, CH$_2$CO), 2.23 (1H, m, CH$_2$CH(CH$_2$)$_2$), 1.2–1.9 (84H, m, CH$_2$).

yield the title compound (810 mg, 60%). $C_{79}H_{143}N_7O_{21}$ requires C: 62.14%, H: 9.44%, N: 6.42%. Found: C: 61.76%, H: 9.42%, N: 6.35%. $C_{79}H_{143}N_7O_{21}$ requires 1526. Found ES+: MH+ 1527.1. $\delta_H$ (CDCl$_3$) 7.15 (1H, br, CONH), 6.47 (1H, br, CONH), 5.95 (1H, br, CONH), 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m, AcOCH$_2$(OAc)CH), 4.65 (2H, br, 2×NH), 4.31 (1H, dd[J$_1$=4 Hz, J$_2$=12 Hz]AcOCH$_2$(OAc), 4.13 (1H, dd[J$_1$=6 Hz, J$_2$=12 Hz]AcOCH$_2$(OAc), 4.70 (2H, br, CONH), 2.9–3.5 (18 H, m, NCH$_2$), 2.0–2.3 (21H, m, MeCO+CH$_2$CO), 1.0–1.7 (82H, dm, CH$_2$), 0.8–0.9 (12H, 4×s, Me).

(H8) N-{8-[t-Butyloxycarbonylaminobutyl(t-butyloxycarbonyl)amino]-7-[t-butyloxycarbonylaminobutyl(t-butyloxycarbonyl)aminomethyl]octyl}-N'-(glucuronylaminoethyl)-4,8,13,17-tetramethyl-1,20-docosadiamide

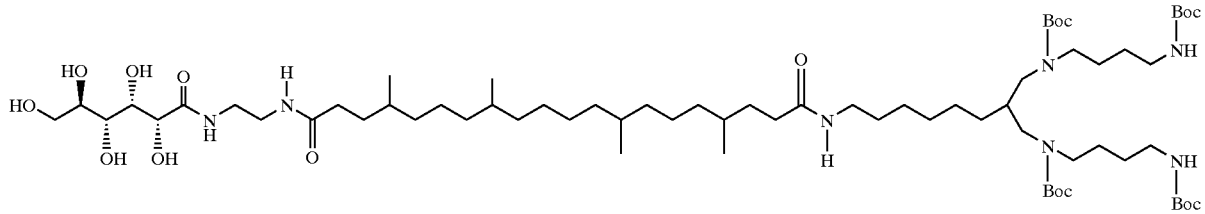

A solution of potassium carbonate (372 mg, 2.7 mmol) in water (1 ml) was added dropwise to a stirred solution of H7 (790 mg, 0.52 mmol) in methanol (12 ml) at room temperature. The flask was stirred for 30 min whereupon tlc showed no starting material was present. Amberlite® CG50 (5 g wet) was added and the resin filtered, washed with methanol & dried. The product was purified by chromatography (silica—10%–20% methanol in dichloromethane) to yield the title compound (230 mg, 72%). $C_{69}H_{133}N_7O_{16}$ requires 1315.9. Found ES+: MH+ 1317.0. $\delta_H$ (CD$_3$OD) 3.64.3 (6H, m, sugar), 3.0–3.4 (18H, m, CH$_2$N), 2.0–2.3 (6H, m, CH$_2$CO), 1.0–1.7 (81H, m, alkane, 0.8–1.0 (12H, 4×s, Me).

(H9) N-[8-(Aminobutylamino)-7-(aminobutylaminomethyl)octyl]-N'-(glucuronylaminoethyl)-4,8,13,17-tetramethyl-1,20-docosadiamide tetra (Trifluoroacetate) Salt DBU (0.05 ml, 0.36 mmol) was added to a stirred suspension of F6 (264 mg, 0.33 mmol) in dry dichloromethane (4 ml) at room temperature under argon. After a few minutes N-hydroxysuccinimide (38 mg, 0.33 mmol) was added followed by EDC (63 mg, 0.33 mmol), the reaction was stirred overnight (tlc showed conversion to the active ester). A solution of B8 (260 mg, 0.36 mmol) and DBU(0.1 ml, 0.66 mmol) in dry dichloromethane (4 ml) was added dropwise and stirring continued for two hours. Tlc showed the active ester had been converted to a slower moving product (silica—60% ethyl acetate in hexane). The solvent was removed and the product chromatographed

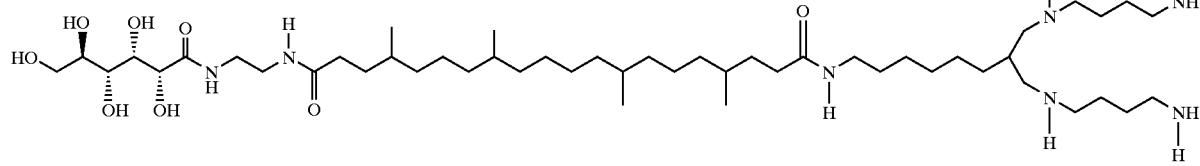

•4CF$_3$CO$_2$H

A solution of H8 (180 mg, 0.137 mmol) in 96% TFA (4% water) was stirred for 30 min at room temperature. The TFA was removed under vacuum, and traces removed by evaporation of water. The title compound was obtained as to a colourless hygroscopic solid (170 mg, 91%) by lyophilisation. The free base $C_{49}H_{101}N_7O_8$ requires 915.8 (salt $C_{57}H_{105}F_{12}N_7O_{16}$=1371). Found ES+: MH+ 917.1. $\delta_H$ (CD$_3$OD) 3.6–4.25 (1+1+4H, 3×m, sugar), 2.9–3.4 (4+8+4H, 3×m, CH$_2$N), 2.1–2.35 (5H, m, CH$_2$CO+CH$_2$CH(CH$_2$)$_2$), 1.0–2.0 (44H, m, alkane), 0.8–1.0 (12H, 4×s, Me).

C24 Amide Tetramine (H10) N-{8-[t-Butyloxycarbonylaminobutyl(t-butyloxycarbonyl)amino]-7-[t-butyloxycarbonylaminobutyl(t-butyloxycarbonyl)aminomethyl]octyl}-12-(peracetylglucuronyl-aminododecanoylamino)dodecanamide (silica—2% to 5% methanol in dichloromethane) to yield the title compound (376 mg, 76%). $C_{77}H_{139}N_7O_{21}$ requires 1498.0. Found ES+: MH+ 1499.0. $\delta_H$ (CDCl$_3$) 6.15 (1H, brt, CONH), 5.92 (1H, br, CONH), 5.75 (1H, br, CONH), 4.7 (2H, br, 2×CONH) 5.67 (1H, t, CH (OAc)CH(OAc)CONH), 5.43 (1H, t, CH(OAc)CH(OAc) CH(OAc)CONH), 5.30 (1H, m, CH(OAc)CONH), 5.05 (1H, m AcOCH$_2$(OAc)CH), 4.31 (1H, dd[J$_1$=4 Hz, J$_2$=12 Hz]AcOCH$_2$(OAc), 4.13 (1H, dd[J$_1$=6 Hz, J$_2$=12 Hz]AcOCH$_2$(OAc), 3.0–3.3 (20H, m, NCH$_2$), 2.0–2.3 (18H, m, MeCO+CH$_2$CO+CH$_2$CH(CH$_2$)$_2$), 1.2–1.7 (90H, dm, CH$_2$+Me).

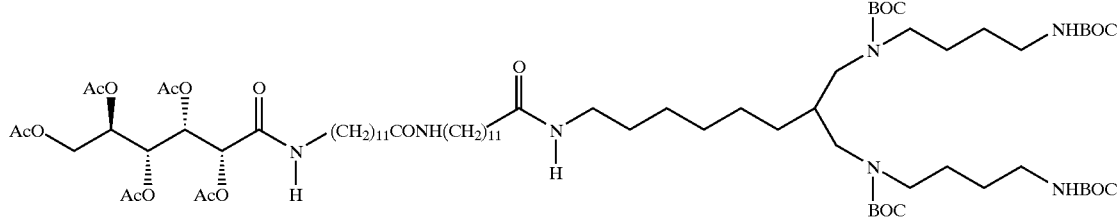

(H11) N-{8-[t-Butyloxycarbonylaminobutyl(t-butyloxycarbonyl)amino]-7-[t-butyloxycarbonylaminobutyl(t-butyloxycarbonyl)aminomethyl]octyl}-12-(glucuronylaminododecanoylamino)dodecanamide

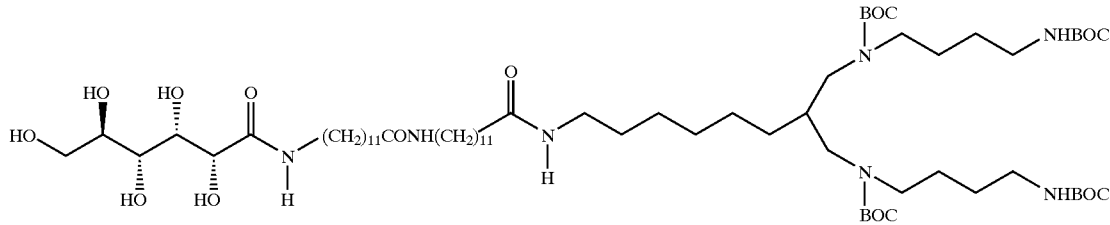

Ammonia solution (20 ml, 0.880) was added to a stirred solution of H10 (370 mg, 0.25 mmol) in methanol (20 ml) at room temperature. The flask was stirred for 30 min and evaporated to dryness. The white solid was suspended in water, filtered off and dried. The product was chromatographed (Reverse phase silica, Merck-Lichroprep eluted with dichloromethane/methanol/water [2:6:1]) The product was evaporated to dryness and triturated with ether. High vacuum yielded the title compound (234 mg) as a white solid. $C_{67}H_{129}N_7O_{16}$ requires 1287.9. Found ES+: MH+ 1288.9. $\delta_H$ (CD$_3$OD) 3.64.2 (6H, m, sugar), 3.0–3.4 (18H, m, CH$_2$N), 2.15 (4H, t, CH$_2$CO), 2.06 (1H, m, CH$_2$CH(CH$_2$)$_2$, 1.2–1.7 (90H, m, CH$_2$+Me).

(H12) N-[8-(Aminobutylamino)-7-(aminobutylaminomethyl)octyl]-12-(glucuronylaminododecanoylamino)dodecanamide tetra(Trifluoroacetate) Salt A solution of H11 (260 mg, 0.18 mmol) in 96% TFA (6 ml, 4% water) was stirred for 30 min at room temperature. The TFA was removed under vacuum, and traces removed by evaporation of toluene/water. The compound was subjected to high vacuum overnight, dissolved in water (5 ml) and filtered through a 0.45 μM (Whatman PP) filter The compound was converted to a colourless solid by lyophilisation. The lyophilised hygroscopic solid was triturated with ether and dried in vacuo to yield the title compound (287 mg, 100%). $C_{47}H_{97}N_7O_8 \cdot C_8H_4O_8 \cdot F_{12} \cdot 3.25H_2O$ (Mwt anhydrous=1344.4) requires C: 47.09%, H: 7.72%, N: 6.99%. Found: C: 49.14%, H: 7.57%, N: 7.29%. The free base $C_{47}H_{97}N_7O_8$ requires 887.7. Found ES+: MH+ 888.7. $\delta_H$ (D$_2$O) 3.6–4.25 (6H, m, sugar), 2.9–3.4 (18H, m, CH$_2$N), 2.15 (4H, dt, CH$_2$CO), 2.23 (1H, m, CH$_2$CH(CH$_2$)$_2$), 1.2–1.9 (54H, m, CH$_2$).

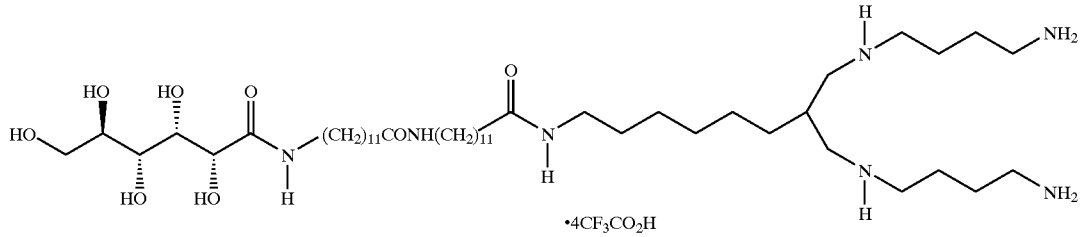

Disugar Tetramines (H13) N-{8-[tButyloxycarbonylaminobutyl(t-butyloxycarbonyl)amino]-7-[t-butyloxycarbonylaminobutyl(t-butyloxycarbonyl)aminomethyl]octylaminocarbonyltricosanyl}-N',N'-bis(peracetylglucuronylaminoethyl)succinamide

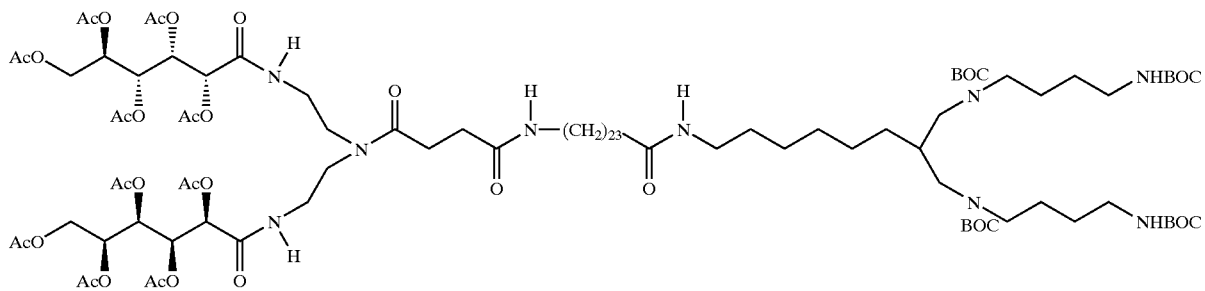

C4 (259 mg, 0.254 mmol), EDC hydrochloride (101 mg, 0.528 mmol) and N-hydroxysuccinimide (46 mg, 0.396 mmol) were dissolved in anhydrous dichloromethane (20 ml) and activated ester formation left at room temperature for two hours under argon. To the solution was added E2 (300 mg, 0.277 mmol) and triethylamine (80 mg, 0.792 mmol) and the reaction left overnight at room temperature under argon. The solvents were removed, and the resulting residues purified by gradient silica column chromatography (3–7% methanol in dichloromethane) to yield the title compound as a colourless solid (350 mg, 65%). $C_{101}H_{175}N_9O_{33}$ requires 2042.2. Found ES$^+$: MH$^+$, 2043.4, MNa$^+$, 2065.5, MK$^+$, 2081.4. $\delta_H$ (CDCl$_3$) 1.24 (48H, br, $(CH_2)_2OCH_2CO$, $(CH_2)_4CH$), 1.43 (48H, br, $(Me)_3C$, $CH_2CH_2N$), 2.03–2.23 (30H, 10×s, MeCO), 2.19 (2H, t, $(CH_2)_{22}CH_2CO$), 2.3–2.8 as a colourless solid (238 mg, 86%). $C_{81}H_{155}N_9O_{23}$ requires 15 1622.1 Found ES$^+$: MH$_2^{2+}$, 812.4, MHNa$^{2+}$, 823.7, ES$^-$: MCl$^-$, 1657.3. $\delta_H$ (CD$_3$OD) 1.28 (46H, br, $(CH_2)_{19}(CH_2)_2CO$, $(CH_2)_4CH$), 1.44 (50H, m, $(Me)_3C$, $CH_2CH_2N$), 2.03 (1H, br, CH), 2.16 (2H, t, $(CH_2)_{22}CH_2CO$), 2.49 (2H, t, CH$_2$CONH), 2.70 (2H, m, CH$_2$CON), 3.0–3.3 (16H, m, CH$_2$NBOC), 3.4–3.6 (8H, m, N(CH$_2$)$_2$N), 3.6–3.85 (8H, m, CHOH), 4.11 (2H, m, CH$_2$OH), 4.19, 4.22 (2H, 2×d, CH$_2$OH).

(H15) N-[8-(Aminobutylamino)-7-(aminobutylaminomethyl) octylaminocarbonyltricosanyl]-N',N-bis(glucuronyl-aminoethyl)succinamide tetra(Trifluoroacetate) Salt

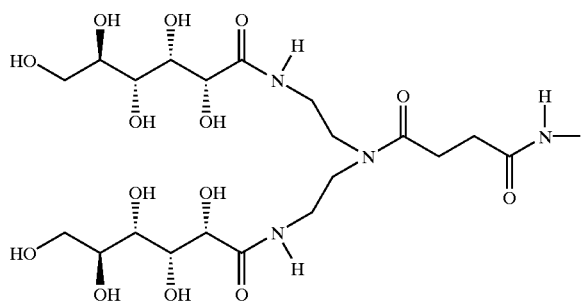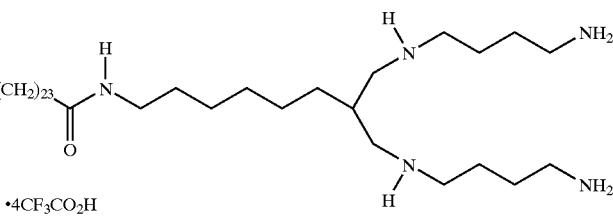

(4H, brm, $(CH_2)_2CO$), 3.0–3.4 (24H, brm, CH$_2$N), 4.10 (2H, m, CH$_2$OAc), 4.31 (2H, m, CH$_2$OAc), 4.65 (2H, br, NHCO$_2$), 5.05 (2H, m, CHCH$_2$OAc), 5.21, 5.25 (2H, 2×d, CHCON), 5.44, 5.66 (4H, 2×m, (CHOAc)$_2$ CHOAcCH$_2$OAc), 5.75 (1H, br, $(CH_2)_{23}$CONH), 6.48 (1H, br, $(CH_2)_2$CONH), 7.21, 7.70 (2H, 2×t, N(CH$_2$CH$_2$NHCO)$_2$).

(H14) N-{8-[t-Butyloxycarbonylaminobutyl(t-butyloxycarbonyl)amino]-7-[t-butyloxycarbonylaminobutyl(t-butyloxycarbonyl)aminomethyl]octylaminocarbonyltricosanyl}-N',N'-bis(glucuronylaminoethyl)succinamide To H14 (234 mg) was added 96:4 trifluoroacetic acid dichloromethane (10 ml). The solution was left for 20 minutes at room temperature, the solvents removed and the residues taken up into MilliQ water. The solution was filtered (0.45 mm polypropylene) and freeze dried to give a white solid. This was suspended in diethyl ether, left for 20 minutes and the ether decanted off. The remaing white solids were dried under vacuum to give the title compound as a white, hydroscopic solid (226 mg). $C_{61}H_{123}N_9O_{15}$ requires 1221.9 Found ES$^+$: MH$_2^{2+}$, 612.0, MH$^+$, 1222.9. $\delta_H$ (D$_2$O) 1.29 (44H, br, $(CH_2)_{19}(CH_2)_2CO$, $(CH_2)_3CH_2CH$), 1.49

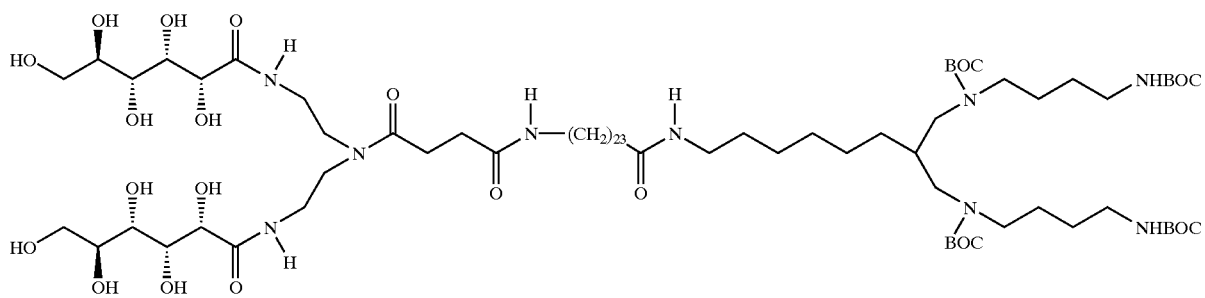

To H13 (349 mg) in methanol (20 ml) was added concentrated ammonium hydroxide (5 ml). The cloudy solution/suspension was rapidly stirred for two hours whereupon the solvent was removed and the resulting residues purified by reverse phase silica chromatography eluting with 2:6:1 dichloromethane:methanol:water to yield the title compound (8H, brm, CH$_2$CH, CH$_2$CH$_2$CO, CH$_2$CH$_2$NHCO), 1.78 (8H, br, NCH$_2$(CH$_2$)$_2$CH$_2$N), 2.21 (3H, br, CH), 2.51, 2.72 (4H, 2×t, CO(CH$_2$)$_2$CO), 3.0–3.3 (16H, m, CH$_2$N), 3.3–3.65 (8H, m, N(CH$_2$)$_2$N), 3.65–3.95 (8H, m, CHOH), 4.10, 4.30 (4H, 2×br, CH$_2$OH).

Carbohydrate Lipid Hexamines

C24 Hexamine (H16) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)-aminobutyl(t-butyloxycarbonyl)aminomethyl]octyl}-24-(peracetylglucuronylamino)tetracosanamide (1H, brt, CONH), 5.67 (1H, t, CH (OAc)CH(OAc) CONH), 5.43 (1H, t, CH(OAc)CH(OAc)CH(OAc) CONH), 5.30 (1H, m, CH(OAc)CONH), 5.05 (1H, m AcOCH$_2$(OAc)CH), 4.31 (1H, dd[J$_1$=4 Hz, J$_2$=12 Hz]AcOCH$_2$(OAc), 4.13 (1H, dd[J$_1$=6 Hz, J$_2$=12 Hz]AcOCH$_2$(OAc), 2.9–3.4 (24H, m, NCH$_2$), 2.0–2.3 (17H, m, CH$_2$CO+5×acetate), 2.23 (1H, m, CH$_2$CH(CH$_2$)$_2$), 1.2–1.8 (118H, dm, CH$_2$+Me).

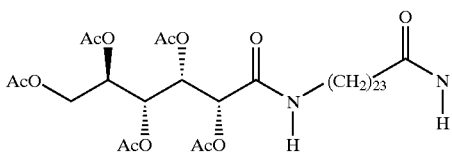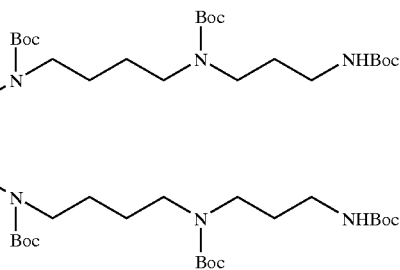

N-Methylmorpholine (0.06 ml, 0.57 mmol) was added to a stirred solution of F2 (400 mg, 0.52 mmol) in dry dichloromethane (10 ml) at room temperature under argon. After a few minutes N-hydroxysuccinimide (66 mg, 0.57 mmol) was added followed by EDC (109 mg, 0.57 mmol), the reaction was stirred overnight (tlc showed conversion to the active ester). A solution of B16 (640 mg, 0.622 mmol) and triethylamine (0.36 ml, 2.6 mmol) in dry dichloromethane (5 ml) was added dropwise and stirring continued for two hours. Tlc showed the active ester had been converted to a slower moving product (silica 40% ethyl acetate in hexane). The solvent was removed and the product chromatographed (silica—66% ethyl acetate in hexane) to yield the title compound (400 mg, 58%). C$_{93}$H$_{170}$N$_8$O$_{24}$ requires 1783.23. Found ES+: MH$^+$ 1785.4. C$_{93}$H$_{170}$N$_8$O$_{24}$ requires C: 63.33%, H: 10.24%, N: 7.12%. Found: C: 63.41%, H: 10.57%, N: 6.98%. $\delta_H$ (CDCl$_3$) 6.07 (1H, brt, CONH), 5.6

(H17) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)-aminobutyl(t-butyloxycarbonyl)aminomethyl]octyl}-24-(glucuronylamino)tetracosanamide

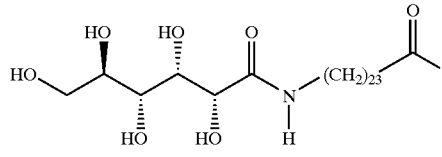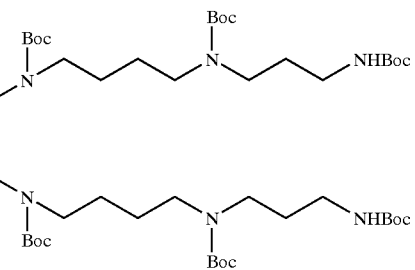

A solution of potassium carbonate (186 mg, 1.26 mmol) in water (1 ml) was added dropwise to a stirred solution of H16 (380 mg, 0.21 mmol) in methanol (7 ml) at room temperature. The flask was stirred for 30 mins whereupon tlc showed no starting material was present. Water (20 ml) was added and the precipitate filtered, washed and dried. The product was purified by chromatography (Reverse phase silica, Merck Lichroprep—15% methanol in dichloromethane) to yield the title compound (445 mg, 57%). C$_{83}$H$_{160}$N$_8$O$_{14}$ requires C: 63.33%, H: 10.24%, N: 7.12%. Found: C: 63.41%, H: 10.57%, N: 6.98%. C$_{67}$H$_{130}$N$_6$O$_{15}$ requires 1573.18. Found ES+: MH$^+$ 1574.3. $\delta_H$ (CD$_3$OD) 3.6–4.2 (6H, m, sugar), 3.0–3.4 (24H, m, CH$_2$N), 2.15 (3H, t, CH$_2$CO), 2.05 (1H, m, CH$_2$CH(CH$_2$)$_2$), 1.2–1.7 (118H, m, CH$_2$+Me),

(H18) N-[8-(Aminopropylaminobutylamino)-7-(aminopropylaminobutylaminomethyl)octyl]-24-(glucuronylamino)tetracosanamide hexa (Trifluoroacetate) Salt

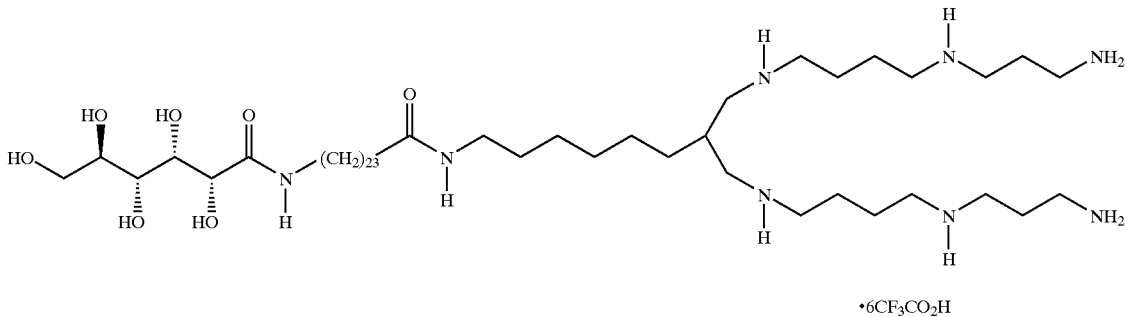

•6CF$_3$CO$_2$H

A solution of H17 (245 mg, 0.353 mmol) in 96% TFA (10 ml, 4% water) was stirred for 30 min at room temperature. The TFA was removed under vacuum, and traces removed by evaporation of water. The title compound was cobtained as a colourless hygroscopic solid (400 mg, 86%) by lyophilisation. $C_{65}H_{118}N_{8O19}F_{18}$·2CF$_3$CO$_2$H requires C: 43.95%, H: 6.42%, N: 5.94%. Found: C: 47.10%, H: 7.18%, N: 6.76%. The free base $C_{53}H_{112}N_8O_7$ requires 972.86. Found ES+: MH$^+$ 973.9. $\delta_H$ (CD$_3$OD) 3.6–4.2 (6H, m, sugar), 3.0–3.4 (24H, m, CH$_2$N), 2.0–2.2 (7H, m, CH$_2$CO+CH$_2$CH (CH$_2$)$_2$+CH$_2$CH$_2$NH$_2$), 1.2–1.7 (60H, m, CH$_2$).

C18 Hexamine (H19) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-18-(peracetylglucuronylamino)octadecanamide N-Methylmorpholine (0.05 ml, 0.42 mmol) was added to a stirred solution of F4 (260 mg, 0.38 mmol) in dry dichloromethane (8 ml) at room temperature under argon. A few minutes later N-hydroxysuccinimide (48 mg, 0.42 mmol) was added followed by EDC (100 mg, 0.42 mmol), the reaction was stirred overnight (tlc showed conversion to the active ester). A solution of B16 (506 mg, 0.49 mmol) and triethylamine (0.3 ml, 1.89 mmol) in dry dichloromethane (6 ml) was added dropwise and stirring continued for two hours. Tlc showed the active ester had been converted to a slower moving product (silica—60% ethyl acetate in hexane). The solvent was removed and the product chromatographed (silica—70% ethyl acetate in hexane) to yield the title compound (420 mg, 65%). $C_{87}H_{158}N_8O_{24}$·2H$_2$O requires C: 60.18%, H: 9.41%, N: 6.45%. Found: C: 60.18%, H: 9.25%, N: 6.55%. $\delta_H$ (CDCl$_3$) 6.07 (1H, brt, CONH), 5.67 (1H, t, CH (OAc)CH(OAc)CONH), 5.43 (1H, t, CH(OAc)CH(OAc)CH(OAc)CONH), 5.30 (1H, m, CH(OAc)CONH), 5.05 (1H, m, AcOCH$_2$(OAc)CH), 4.31 (1H, dd[J$_1$=4 Hz, J$_2$=12 Hz]AcOCH$_2$(OAc), 4.13 (1H, dd[J$_1$=6 Hz, J$_2$=12 Hz]AcOCH$_2$(OAc), 2.9–3.4 (24H, m, NCH$_2$), 2.0–2.3 (17H, m, CH$_2$CO+5×acetate), 1.95 (1H, m, CH$_2$CH(CH$_2$)$_2$), 1.2–1.8 (106H, tm, CH$_2$+Me).

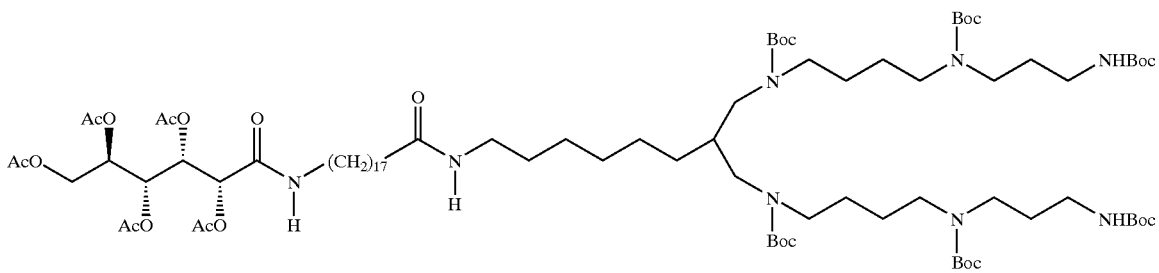

(H20) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-18-(glucuronylamino)octadecanamide

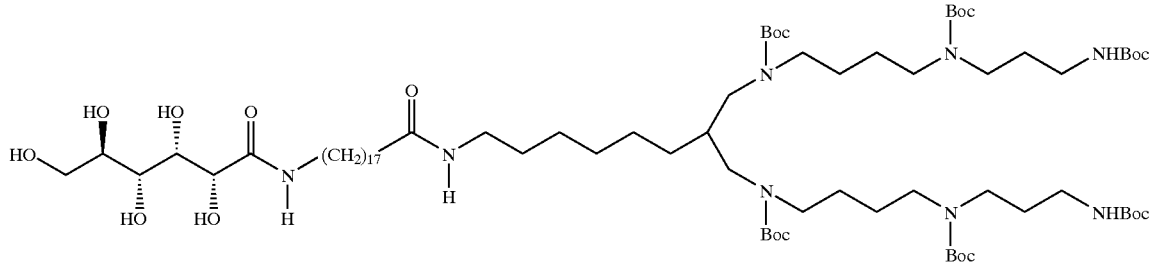

A solution of potassium carbonate (178 mg, 1.28 mmol) in water (1 ml) was added dropwise to a stirred solution of H19 (420 mg, 0.25 mmol) in methanol (7 ml) at room temperature. The flask was stirred for 30 min whereupon tlc showed no starting material was present. Water (20 ml) was added and the precipitate filtered, washed and dried. The product was purified by chromatography (Reverse phase silica, Merck Lichroprep—dichloromethane/methanol/water [2:6:1]) to yield, after trituration, with ether the title compound (220 mg, 60%). $C_{67}H_{130}N_6O_{15}$ requires 1489. Found ES+: MH+ 1490.

(H21) N-[8-(Aminopropylaminobutylamino)-7-(aminopropylaminobutylaminomethyl)octyl]-18-(glucuronylamino)octadecanamide hexa (Trifluoroacetate) Salt A solution of H20 (200 mg, 0.134 mmol) in 96% TFA (10 ml, 4% water) was stirred for 30 min at room temperature. The TFA was removed under vacuum, and traces removed by evaporation of toluene/methanol, then high vacuum. The compound was dissolved in water (8 ml) and filtered through a 0.45 μm filter (Whatman PP), the compound was converted to a colourless solid by lyophilisation. The product was triturated with ether to give the title compound as a hygroscopic white solid (183 mg, 88%). $C_{59}H_{106}N_8O_{19}F_{18} \cdot 2H_2O$ (anhydrous M. Wt 1572) requires C: 44.03%, H: 6.89%, N: 6.96%. Found: C: 43.99%, H: 6.67%, N: 6.89%. The free base $C_{47}H_{100}N_8O_7$ requires 888.7. Found ES+: MH+ 890. $\delta_H$ (CD$_3$OD) 3.6–4.2 (6H, m, sugar), 3.0–3.4 (24H, m, CH$_2$N+CH$_2$NH$_2$), 2.0–2.2 (7H, m, CH$_2$CO+CH$_2$ CH(CH$_2$)$_2$+CH$_2$CH$_2$NH$_2$), 1.2–1.7 (48H, m, CH$_2$).

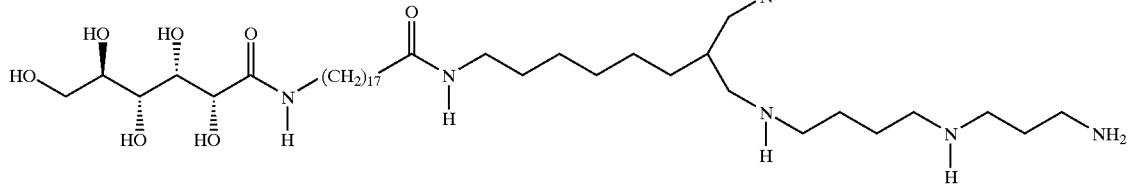

Bixin Hexamine
(H22) N-{8-[t-Butyloxycarbonylaminopropyl(t-butyloxycarbonyl)-aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-N'-(peracetylglucuronylaminoethyl)-4,8,13,17-tetramethyl-1,20-docosadiamide

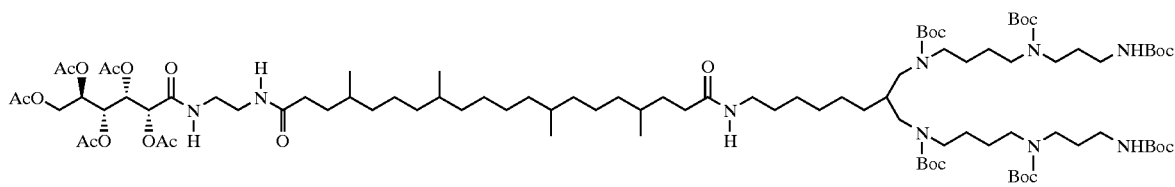

N-Methylmorpholine (0.04 ml, 0.34 mmol) was added to a stirred solution of F5 (282 mg, 0.34 mmol) in dry dichloromethane (10 ml) at room temperature under argon. After a few minutes N-hydroxysuccinimide (39 mg, 0.34 mmol) was added followed by EDC (65 mg, 0.34 mmol), the reaction was stirred overnight (tlc showed conversion to the active ester). A solution of B16 (318 mg, 0.34 mmol) and triethylamine (0.237 ml, 1.7 mmol) in dry dichloromethane (10 ml) was added dropwise and stirring continued for two hours. Tlc showed the active ester had been converted to a slower moving product (silica—10% methanol in dichloromethane). The solvent was removed and the product chromatographed (silica—5% methanol in dichloromethane) to yield the title compound (430 mg, 69%). $C_{95}H_{173}N_9O_{25}$ requires 1840.25. Found ES+: MH+ 1841.2. $\delta_H$ (CDCl$_3$) 7.10 (1H, br, CONH), 6.27 (1H, br, CONH), 5.75 (1H, br, CONH), 5.67 (1H, t, CH(OAc)CH (OAc)CONH), 5.43 (1H, t, CH(OAc)CH(OAc)CH(OAc) CONH), 5.30 (1H, m, CH(OAc)CONH), 5.05 (1H, m, AcOCH$_2$(OAc)CH), 4.31 (1H, dd[J$_1$=4 Hz, J$_2$=12 Hz]AcOCH$_2$(OAc), 4.13 (1H, dd[J$_1$=6 Hz, J$_2$=12 Hz]AcOCH$_2$(OAc), 2.9–3.5 (26H, m, NCH$_2$), 2.0–2.3 (15+ 9H, m, MeCO+CH$_2$CO+CH$_2$CH(CH$_2$)$_2$+MeCH), 1.0–1.8 (54+12+30H, ms, CH$_2$), 0.84–0.91 (12H, 4xs, Me).

(H23) N-{8-[t-Butyloxycarbonylaminopropyl(t-butyloxycarbonyl)aminobutyl(t-butyloxycarbonyl) amino]-7-[t-butyloxycarbonylaminopropyl(t-butyloxycarbonyl)aminobutyl(t-butyloxycarbonyl) aminomethyl]octyl)-N'-(glucuronylaminoethyl)-4,8, 13,17-tetramethyl-1,20-docosadiamide Ammonia solution (0.880, 7 ml) was added to a stirred solution of H22 (600 mg, 0.33 mmol) in methanol (15 ml, or until in solution when ammonia added) at room temperature. The flask was stirred for 1 hr whereupon tlc showed no starting material was present. The reaction was evaporated to dryness and the product purified by chromatography (Reverse phase silica, Merck Lichroprep—dichloromethane/methanol/water [2:6:1]) to yield the title compound (416 mg, 78%). $C_{85}H_{163}N_9O_{20}.3/4H_2O$ (anhydrous M. Wt 1630) requires C: 62.07%, H: 10.08%, N: 7.66%. Found: C: 62.08%, H: 10.14%, N: 7.69%. $C_{85}H_{163}N_9O_{20}$ requires 1630. Found ES+: MH+ 1631.2. $\delta_H$ (CD$_3$OD), 3.6–4.3 (6H, ms, sugar), 2.9–3.5 (26H, m, NCH$_2$), 2.0–2.3 (9H, m, CH$_2$CO+CH$_2$CH(CH$_2$)$_{2+4}$× CH$_3$CH), 1.0–1.8 (54+12+30H, ms, Me+CH$_2$), 0.84–0.91 (12H, 4xs, Me).

(H24) N-[8-(Aminopropylaminobutylamino)-7-(aminopropylaminobutylaminomethyl)octyl]-N'-(glucuronyl-aminoethyl)-4,8,13,17-tetramethyl-1,20-docosadiamide hexa(Trifluoroacetate) Salt

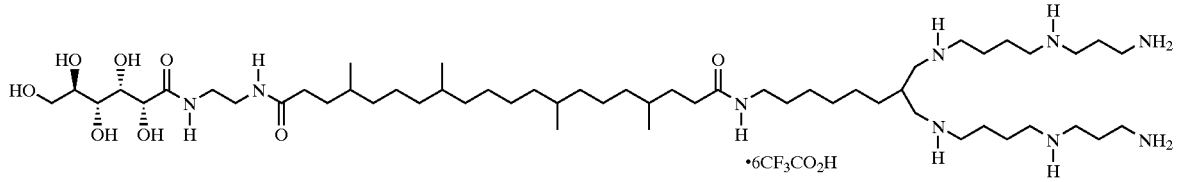

A solution of H23 (400 mg, 0.25 mmol) in 96% TFA (10 ml, 4% water) was stirred for 30 min at room temperature. The TFA was removed under vacuum, and traces removed by evaporation of water. The title compound was obtained as to a colourless hygroscopic solid (382 mg, 90%) by lyophilisation. $C_{55}H_{115}N_9O_8.C_{12}H_6F_{18}O_{12}.2.5H_2O$ (anhydrous M.Wt 1713 requires C: 45.73%, H: 7.22%, N: 7.16%. Found: C: 45.73%, H: 15 7.14%, N: 6.86%. The free base $C_{49}H_{101}N_7O_8$ requires 1029.89. Found ES+: MH+ 1031.0. $\delta_H$ (CD$_3$OD), 3.6–4.3 (6H, ms, sugar), 2.9–3.5 (26H, m, NCH$_2$), 2.0–2.3 (9H, m, CH$_2$CO+CH$_2$CH(CH$_2$)$_2$+4× MeCH), 1.0–1.8 (12+30H, ms, CH$_2$), 0.84–0.91 (12H, 4xs, Me).

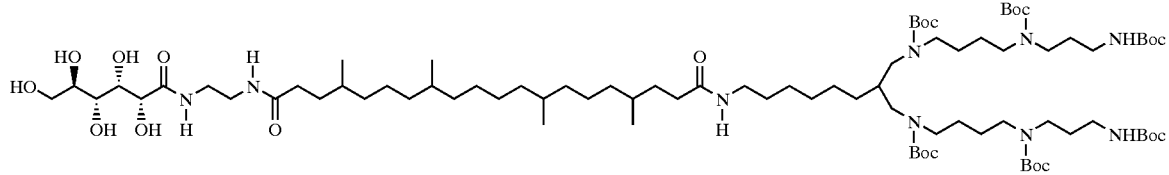

C24 Amide Hexamine (H25) N-{8-[t-Butyloxycarbonylaminopropyl(t-butyloxycarbonyl)-aminobutyl(t-butyloxycarbonyl)-amino]-7-[t-butyloxycarbonylaminopropyl(t-butyloxycarbonyl)butyl(tbutyloxycarbonyl)aminomethyl]octyl}-12-(peracetylglucuronylaminododecanoylamino)dodecanamide

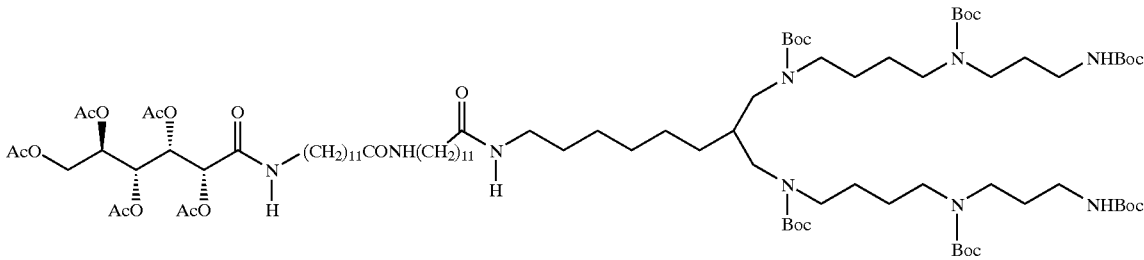

DBU (0.06 ml, 0.4 mmol) was added to a stirred suspension of F6 (320 mg, 0.4 mmol) in dry dichloromethane (5 ml) at room temperature under argon. A few minutes later N-hydroxysuccinimide (46 mg, 0.4 mmol) was added followed by EDC (76 mg, 0.4 mmol), the reaction was stirred overnight (tlc showed conversion to the active ester). A solution of B16 (411 mg, 0.4 mmol) and DBU(0.12 ml, 0.4 mmol) in dry dichloromethane (5 ml) was added dropwise and stirring continued for five hours. Tlc showed the active ester had been converted to a slower moving product (silica—60% ethyl acetate in hexane). The reaction was poured into 10% citric acid and extracted with dichloromethane, washed with brine, dried, and the solvent removed. The product was purified by chromatography (silica—2% to 5% methanol in dichloromethane) to yield the title compound (538 mg, 74%). $C_{93}H_{169}N_9O_{25}.3/4H_2O$ requires C: 61.14%, H: 9.41% N: 6.90%. Found: C: 61.16%, H: 9.37%, N: 6.82%. $C_{93}H_{169}N_9O_{25}$ requires 1812.2. Found ES+: MH+ 1814.3. $\delta_H$ (CDCl$_3$) 6.13 (1H, brt, CONH), 5.93 (1H, br, CONH), 5.75 (1H, br, CONH), 5.67 (1H, t, CH(OAc)CH(OAc)CONH), 5.43 (1H, t, CH(OAc)CH (OAc)CH(OAc)CONH), 5.30 (1H, m, CH(OAc)CONH), 5.05 (1H, m AcOCH$_2$(OAc)CH), 4.31 (1H, dd[J$_1$=4 Hz, J$_2$=12 Hz]AcOCH$_2$(OAc), 4.13 (1H, dd[J$_1$=6 Hz, J$_2$=12 Hz]AcOCH$_2$(OAc), 2.9–3.3 (26H, m, NCH$_2$), 2.0–2.3 (20H, m, MeCO+CH$_2$CO+CH$_2$CH(CH$_2$)$_2$), 1.2–1.7 (112H, dm, CH$_2$+Me).

(H26) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)butyl(t-butyloxycarbonyl)aminomethyl]octyl}-12-(glucuronylaminododecanoylamino)dodecanamide

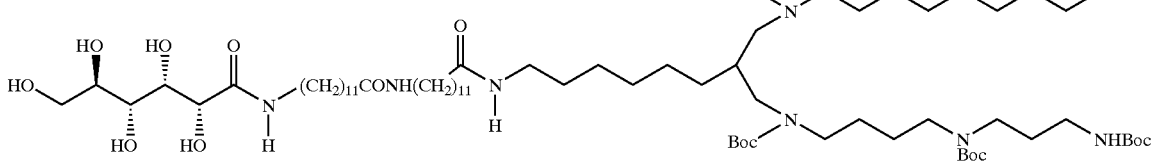

Ammonia solution (10 ml, 0.880) was added to a stirred solution of H25 (530 mg, 0.3 mmol) in methanol (10 ml) at room temperature, (extra methanol can be added to ensure a solution). The flask was stirred for 1 hr and evaporated to dryness. The white solid was suspended in water, filtered off and dried. The product was purified by chromatography (Reverse phase silica, Merck-Lichroprep eluted with dichloromethane/-methanol/water [2:6:1]) The product was evaporated to dryness, suspended in water, filtered off, dried and triturated with ether. High vacuum yielded the title compound (368 mg, 77%) as a white solid. $C_{83}H_{159}N_9O_{20}$ requires C: 62.18%, H: 10.00%, N: 7.86%. Found: C: 62.04%, H: 9.93%, N: 7.77%. $C_{83}H_{159}N_9O_{20}$ requires 1602.17. Found ES+: MH+ 1603.4. $\delta_H$(CD$_3$OD) 3.54.2 (6H, m, sugar), 2.9–3.3 (26H, m, NCH$_2$), 2.15 (4H, t, CH$_2$CO), 2.07 (1H, br, CH$_2$CH(CH$_2$)$_2$), 1.2–1.8 (112H, dm, CH$_2$+ Me).

(H27) N-[8-(Aminopropylaminobutylamino)-7-(aminopropylbutylaminomethyl)octyl]-12-(glucuronylaminododecanoylamino) dodecanamidehexa(trifluoroacetate) Salt

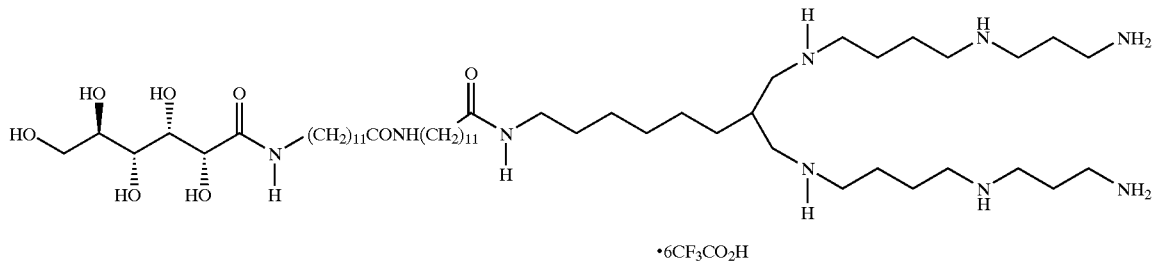

A solution of H26 (360 mg, 0.23 mmol) in 96% TFA (6 ml, 4% water) was stirred for 30 min at room temperature. The TFA was removed under vacuum, and traces removed by evaporation of toluene/methanol. The compound was subjected to high vacuum overnight, dissolved in water (5 ml) and filtered through a 0.45 $\mu$M (Whatman PP) filter The compound was converted to a colourless solid by lyophilisation. The lyophilised hygroscopic solid was triturated with ether and dried in vacuo to yield the title compound (370 mg, 98%). $C_{53}H_{111}N_9O_{20} \cdot C_{12}H_6O_{12}F_8 \cdot 2.8H_2O$ (Mwt anhydrous=1686.67) requires C: 44.94%, H: 7.11%, N: 7.26%. Found: C: 44.93%, H: 6.92%, N: 7.12%. The free base $C_{53}H_{111}N_9O_8$ requires 1001.86. Found ES+: MH$^+$ 1003.9. $\delta_H$ (CD$_3$OD) 7.92 (1H, br, CONH), 7.80 (1H, br, CONH), 3.6–4.25 (6H, m, sugar), 2.9–3.4 (26H, m, CH$_2$N), 2.0–2.3 (9H, m, CH$_2$CO+CH$_2$CH(CH$_2$)$_2$+CH$_2$CH$_2$NH$_2$), 1.2–1.9 (50H, m, CH$_2$).

Disugar Hexamine

(H28) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)-aminomethyl]octylaminocarbonyltricosanyl}-N',N'-bis(peracetylglucuronylaminoethyl)succinamide C4 (197 mg, 0.201 mmol), EDC hydrochloride (77 mg, 0.401 mmol) and N-hydroxysuccinimide (35 mg, 0.301 mmol) were dissolved in anhydrous dichloromethane (30 ml) and activated ester formation left at room temperature for two hours under argon. To the solution was added E4 (300 mg, 0.211 mmol) and triethylamine (61 mg, 0.602 mmol) and the reaction left overnight at room temperature under argon. The solvents were removed, and the resulting residues purified by gradient silica column chromatography (3–7% methanol in dichloromethane) to yield the title compound as a colourless solid (378 mg, 78%). $C_{119}H_{209}N_{11}O_{37}$ requires 2384.5. Found ES$^+$: MH$_2^{2+}$, 1193.9, MH$_3^{3+}$, 796.4. $\delta_H$ (CDCl$_3$) 1.23 (46H, (CH$_2$)$_{19}$(CH$_2$)$_2$CO, (CH$_2$)$_4$CH), 1.44 (72H, br+m, (Me)$_3$C, CH$_2$CH$_2$N, CH$_2$CH$_2$CO), 1.95 (1H, br, CH), 2.02–2.23 (30H, 10×s, MeCO), 2.17 (2H, t, (CH$_2$)$_{22}$CH$_2$CO), 2.4–2.8 (4H, brm, CO(CH$_2$)$_2$CO), 2.83 (6H, s, MeN), 2.9–3.5 (32H, m, CH$_2$N), 4.12 (2H, m, CH$_2$OAc), 4.30 (2H, dt, CH$_2$OAc), 5.20, 5.25 (2H, 2×d, CHOAcCO), 5.43, 5.60 (4H, 2×m, (CHOAc)$_2$CHOAcCO), 5.71 (1H, br, (CH$_2$)$_{23}$CONH), 6.11 (1H, br, CO(CH$_2$)$_2$CONH), 7.18, 7.65 (2H, 2×t, N(CH$_2$CH$_2$NH)$_2$.

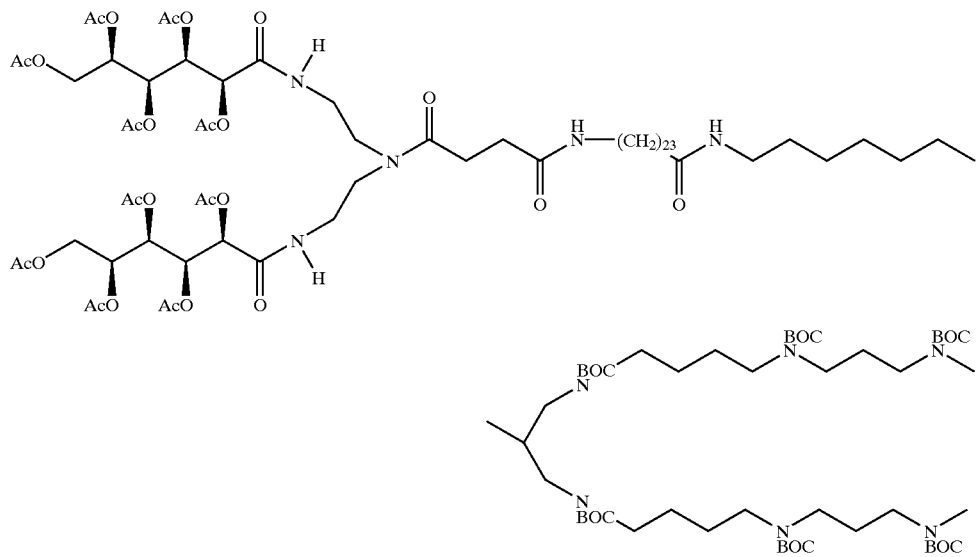

(H29) N-{8-[Methyl(t-butyloxycarbonyl)
aminopropyl(t-butyloxycarbonyl)aminobutyl(t-
butyloxycarbonyl)amino]-7-[methyl(t-
butyloxycarbonyl)aminopropyl(t-butyloxycarbonyl)
aminobutyl(t-butyloxycarbonyl)aminomethyl]
octylaminocarbonyltricosanyl}-N N'-bis
(glucuronylaminoethyl)succinamide

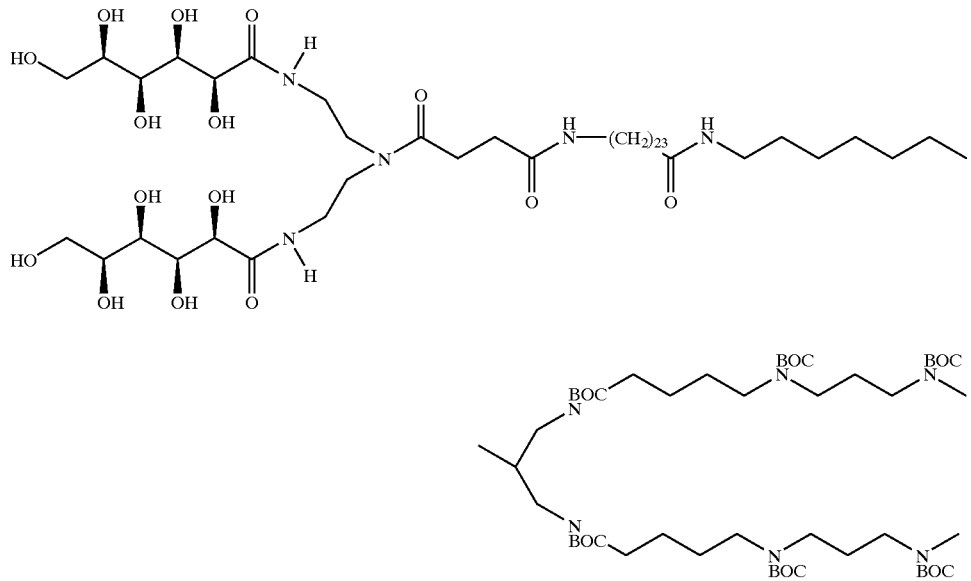

To H28 (377 mg) in methanol (15 ml) was added concentrated ammonium hydroxide (5 ml). The cloudy solution/suspension was rapidly stirred for two hours whereupon the solvent was removed and the resulting residues purified by reverse phase silica chromatography eluting with 2:6:1 dichloromethane:methanol:water to yield the title compound as a colourless solid (266 mg, 86%). $C_{99}H_{189}N_{11}O_{27}$ requires 1964.4 Found ES$^+$: MH$_2^{2+}$, 983.7. $\delta_H$ (CD$_3$OD) 1.28 (46H, br, $(CH_2)_{19}(CH_2)_2CO$, $(CH_2)_4CH$), 1.46 (68H, br, $(Me)_3C$, $CH_2CH_2N$, $CH_2CH_2CO$), 1.76 (4H, p, NCH$_2$CH$_2$CH$_2$N), 2.10 (1H, br, CH), 2.16 (2H, t, $(CH_2)_{22}$H$_2$CO), 2.49, 2.70 (4H, t+dt, CO(CH$_2$)$_2$CO), 2.85 (6H, s, NMe), 3.03.4 (24H, m, CH$_2$N), 3.4–3.65 (8H, m, N(CH$_2$)$_2$N, 3.65–3.85 (8H, m, CHOH), 4.11, 4.20 (4H, brs+dd, CH$_2$OH). n (H30) N-[8-(Methylaminopropylaminobutylamino)-
7-(methylaminopropylaminobutylamino)
octylaminocarbonyltricosanyl}-N',N'-bis
(glucuronylaminoethyl)succinamide

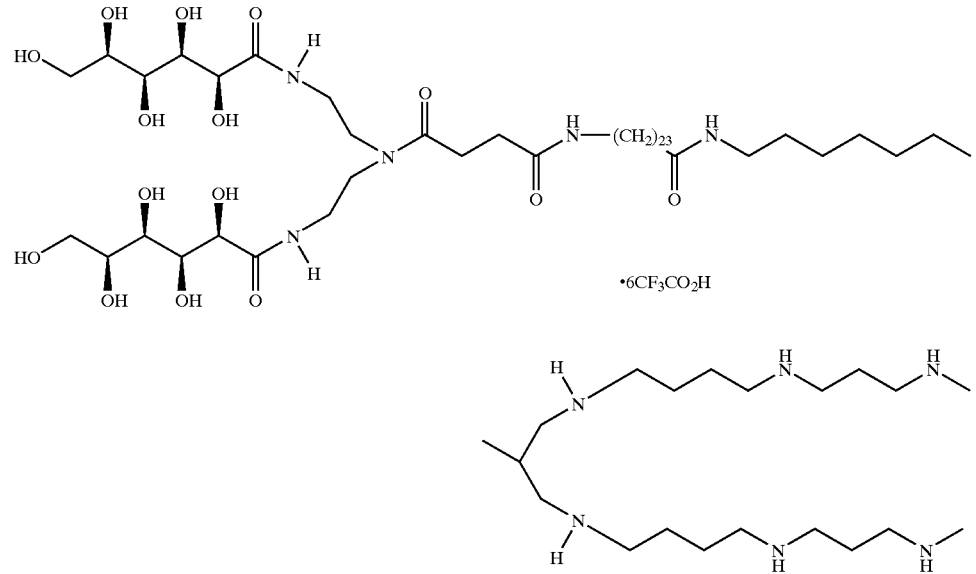

•6CF$_3$CO$_2$H

To H29 (266 mg) was added 96:4 trifluoroacetic acid-:dichloromethane (10 ml). The solution was left for 20 minutes at room temperature, the solvents removed and the residues taken up into MilliQ water. The solution was filtered (0.45 mm polypropylene) and freeze dried to give a white solid. This was suspended in diethyl ether, left for 20 minutes and the ether decanted off. The remaining white solids were dried under vacuum to give the title compound as a white, hydroscopic solid (269 mg). $C_{69}H_{141}N_{11}O_{15}$ requires 1364.1 Found ES$^+$: MH$_2^{2+}$, 683.4, MH$^+$,136.4. $\delta_H$ (CD$_3$OD) 1.28 (44H, br, (CH$_2$)$_{19}$(CH$_2$)$_2$CO, (CH$_2$)$_3$CH$_2$CH), 1.50 (8H, m, CH$_2$CH, CH$_2$CH$_2$NH, CH$_2$CH$_2$CO), 1.82 (8H, br, NCH$_2$(CH$_2$)$_2$CH$_2$N), 2.05–2.25 (6H, m, CH$_2$CO, NCH$_2$CH$_2$CH$_2$N), 2.28 (1H, m, CH), 2.49, 2.72 (4H, 2×t, CO(CH$_2$)$_2$CO), 2.73 (6H, s, NMe), 3.05–3.30 (24H, m, CH$_2$N), 3.35–3.65 (8H; m, NCH$_2$CH$_2$N), 3.65–3.85 (8H, m, CHOH), 4.10, 4.22 (4H, brs+dd, CH$_2$OH).

(H31) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)-aminomethyl]octyl}-24-(peracetylglucuronylamino)tetracosanamide To F2 (131 mg, 0.170 mmol) in anhydrous dichloromethane (15 ml) were added EDC hydrochloride (46 mg, 0.238 mmol), N-hydroxysuccinimide (27 mg, 0.238 mmol) and the reaction left overnight. To the reaction were then added B21 (198 mg, 0.187 mmol) and triethylamine (68 mg, 0.679 mmol) and the reaction left for 3 hours at which point the solvent was removed. The residues were purified by gradient silica chromatography eluting with 60–80% ethyl acetate in hexane to yield the title compound as a colourless gum, (241 mg, 78%). $C_{95}H_{174}N_8O_{24}$ requires 1811.3 Found ES$^+$: MH$_2^{2+}$, 907.0. $\delta_H$ (CDCl$_3$) 1.24 (48H, br, (CH$_2$)$_{19}$(CH$_2$)$_2$N, CH$_2$CH$_2$CO, (CH$_2$)$_4$CH), 1.3–1.8 (70H, m, (Me)$_3$mC, CH$_2$CH$_2$N), 2.0 (1H, br, CH), 2.04–2.19 (15H, 5×s, MeCO), 2.22 (2H, t, CH$_2$CO), 2.83 (6H, s, NMe), 2.9–3.35 (24H, m, CH$_2$N), 4.10–4.40 (2H, m, CH$_2$OAc), 5.03 (1H, m, CHOAcCH$_2$OAc), 5.28 (1H, d, CHOAcCO), 5.43, 5.67 (2H, 2×t, (CHOAc)$_2$CHOAcCH$_2$OAc), 6.05 (2H, 2×t, NHCO).

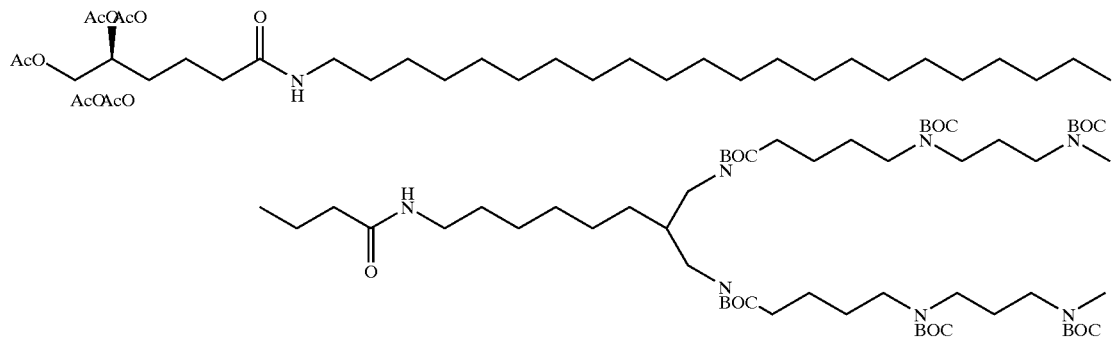

(H32) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-24-(glucuronylamino)tetracosanamide

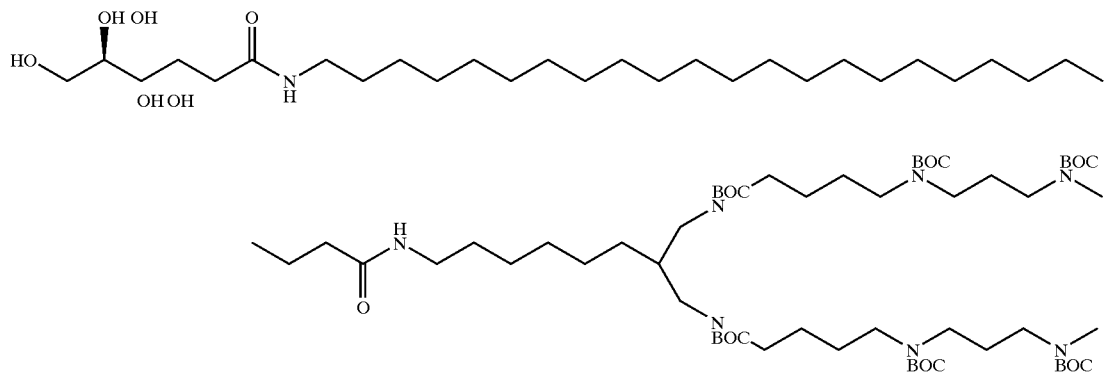

To H31 (235 mg) dissolved in methanol (10 ml) was slowly added with stirring NH$_4$OH (4 ml) until the solution started to become cloudy. After approximately 20 minutes an additional 3 ml of methanol was added to dissolve some of the forming white precipitate. The solution/suspension was stirred for a total of one hour at which point all solvents were removed. The residues were purified by reverse phase chromatography eluting with 2:6:1 CH$_2$Cl$_2$:MeOH:NH$_4$OH to yield the title compound as a colourless solid, (206 mg, 99%). C$_{85}$H$_{164}$N$_8$O$_{19}$ requires 1601.2 Found ES$^+$: MH$^+$, 1601.9. δ$_H$ (CDCl$_3$) 1.24 (46H, br, (CH$_2$)$_{19}$(CH$_2$)$_2$N, (CH$_2$)$_4$CH), 1.35–1.80 (72H, brm, (Me)$_3$C, CH$_2$CH$_2$N, CH$_2$CH$_2$CO), 2.05 (1H, br, CH), 2.14 (2H, t, (CH$_2$)$_{22}$CH$_2$CO), 2.82 (6H, s, NMe), 3.0–3.4 (24H, brm, NCH$_2$), 3.54.1 (4H, br, CHOH), 4.17, 4.30 (2H, 2×br, CH$_2$OH), 5.85, 7.21 (2H, 2×br, NHCO).

H32 (185 mg) was dissolved in 96:4 TFA:DCM and left for 20 minutes. The solvent was removed and the residues taken up in MilliQ water, filtered through a 0.2 mm filter, and the solution freeze dried to quantitatively give the title compound as a white solid. C$_{55}$H$_{116}$N$_8$O$_7$ requires 1000.9 Found ES$^+$: MH$^+$, 1001.9. δ$_H$ (CD$_3$OD) 1.32 (44H, br, (CH$_2$)$_{19}$(CH$_2$)$_2$CO. (CH$_2$)$_3$CH$_2$CH), 1.52 (8H, m, CH$_2$CH, CH$_2$CH$_2$N, CH$_2$CH$_2$CO), 1.82 (8H, m, NCH$_2$(CH$_2$)$_2$CH$_2$N), 2.08 (1H, br, CH), 2.12 (4H, m, NCH$_2$CH$_2$CH$_2$N), 2.23 (2H, m, CH$_2$CO), 2.73 (6H, s, NMe), 3.0–3.3 (24H, m, CH$_2$N), 3.58–3.82 (4H, m, CHOH), 4.08, 4.22 (2H, 2×m, CH$_2$OH).

(H33) N-[8-(Methylaminopropylaminobutylamino)-7-(methylaminopropylaminobutylaminomethyl)octyl]-24-(glucuronylamino)tetracosanamide

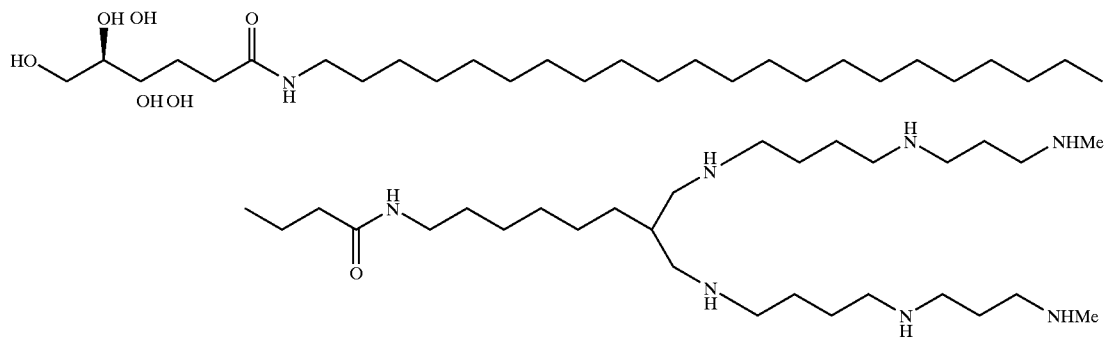

(H34) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-24-(peracetylglucuronylaminododecanoylamino)tetracosanamide

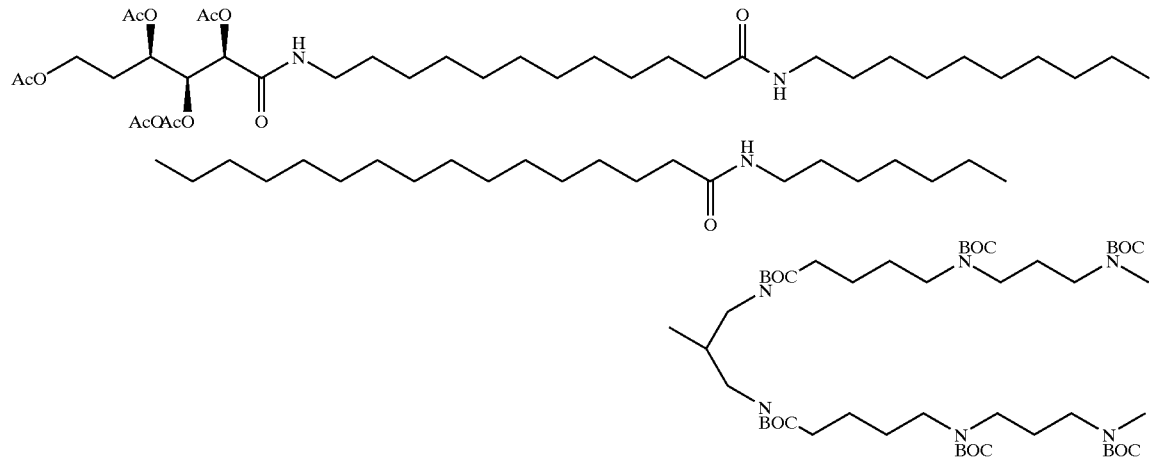

To F8 (67 mg, 0.111 mmol) in anhydrous dichloromethane (20 ml) were added EDC hydrochloride (30 mg, 0.155 mmol), N-hydroxysuccinimide (18 mg, 0.155 mmol) and the reaction left overnight. To this were then added E4 (174 mg, 0.122 mmol) and triethylamine (45 mg, 0.444 mmol) and the reaction left for a further four hours. The solvent was removed and the residues purified by gradient silica chromatography eluting with 50–90% ethyl acetate in hexane to yield the title compound. (90 mg, 40%) as a colourless gum. $C_{107}H_{197}N_9O_{25}$ requires 2008.4 Found ES$^+$: MNH$_4^+$, 2027.8. $\delta_H$ (CDCl$_3$) 1.25 (56H, br, NH(CH$_2$)$_2$(CH$_2$)$_{20}$, NH(CH$_2$)$_2$(CH$_2$)$_8$), 1.3–1.8 (72H, brm, (Me)$_3$C, CH$_2$CH$_2$N), 1.96 (1H, br, CH), 2.04, 2.05, 2.09, 2.20, 2.20 (15H, 5×s, MeCO), 2.23 (4H, m, CH$_2$CO), 2.84 (6H, s, NMe), 3.0–3.3 (26H, m, NCH$_2$), 4.14, 4.31 (2H, m, CH$_2$OAc), 5.04 (1H, dt, CH$_2$CHOAc), 5.29 (1H, d, CHOAcCO), 5.44, 5.66 (2H, 2×t, (CHOAc)$_2$CHOAcCO), 5.92, 6.09, 6.29 (3H, br+t+br, NHCO).

(H35) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-24-(glucuronylaminododecanoylamino)tetracosanamide To a solution of H34 (90 mg) in methanol (12 ml) was added NH$_4$OH (4 ml) and the reaction left for 1 hour at which point the solvent was removed. The residues were purified by reverse phase silica chromatography eluting with 2:6:1 DCM:MeOH:H$_2$O to yield the title compound (80 mg, 99%) as a white solid. $C_{97}H_{187}N_9O_{20}$ requires 1798.4 Found ES$^+$: MH$_2^{2+}$, 900.9, MH$^+$, 1799.6. $\delta_H$ (CDCl$_3$) 1.25 (52H, br, N(CH$_2$)$_2$(CH$_2$)$_{19}$, N(CH$_2$)$_2$(CH$_2$)$_7$), 1.40–1.85 (76H, brm, (Me)$_3$C, CH$_2$CH$_2$N, CH$_2$CH$_2$CO), 1.95 (1H, br, CH), 2.16 (2H, t, CH$_2$CO), 2.84 (6H, s, NMe), 2.9–3.4 (26H, m, NCH$_2$), 3.82 (4H, br, CHOH), 4.17, 4.32 (2H, 2×br, CH$_2$OH), 5.92, 6.55, 7.22 (3H, 3×br, NHCO).

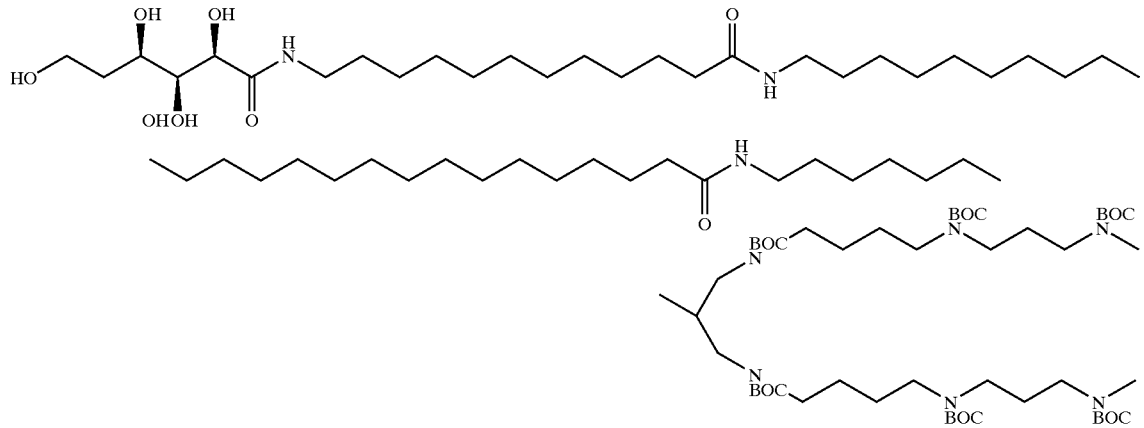

(H36) N-[8-(Methylaminopropylaminobutylamino)-7-(methylaminopropylaminobutylaminomethyl)octyl]-24-(glucuronylaminododecanoylamino)tetracosanamide

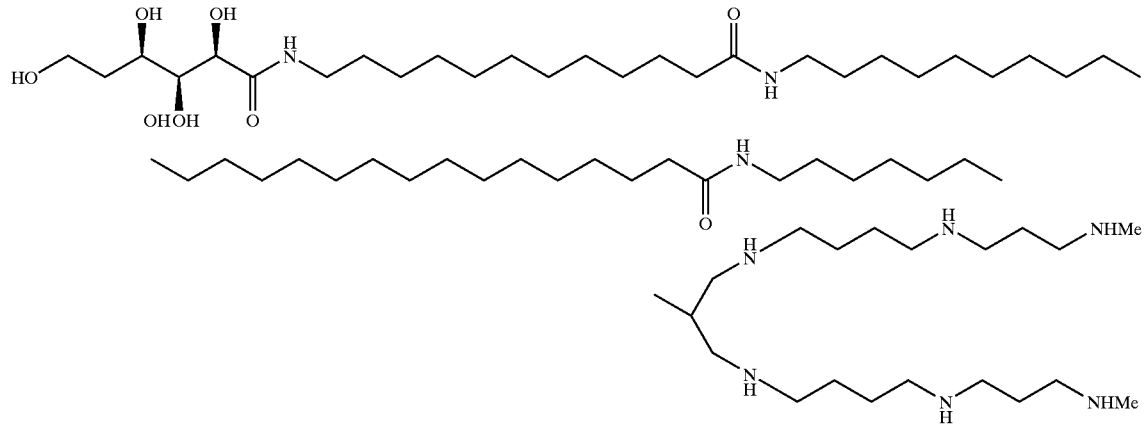

H35 (80 mg) was treated as in the synthesis of H33 to give the title compound in quantitative yield as a white solid. $C_{67}H_{139}N_9O_8$ requires 1198.1 Found ES$^+$: $MH_2^{2+}$, 600.2, MH$^+$, 1198.8. $\delta_H$ (CD$_3$OD) 28 (58H, br, (CH$_2$)$_7$(CH$_2$)$_2$CO, (CH$_2$)$_{19}$(CH$_2$)$_2$CO, (CH$_2$)$_3$CH$_2$CH), 1.51 (12H, m, CH$_2$CH, CH$_2$CH$_2$N, CH$_2$CH$_2$CO), 1.83 (8H, m, NCH$_2$(CH$_2$)$_2$CH$_2$N), 2.14 (9H, m, CH$_2$CO, NCH$_2$CH$_2$CH$_2$N, CH), 2.73 (6H, s, NMe), 3.0–3.3 (26H, m, NCH$_2$), 3.6–3.8 (4H, m, CHOH), 4.07, 4.19 (2H, 2×m, CH$_2$OH).

(H37) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-36-(glucuronylamino)hexatriacontanamide To E8 (612 mg, 0.038 mmol) in anhydrous methanol (15 ml) were added d-gluconolactone (14 mg, 0.077 mmol) and triethylamine (16 mg, 0.153 mmol) and the reaction stirred overnight at ambient temperature under argon. The solvents were removed and the residues purified by reverse phase chromatography eluting with 2:6:1 then 2:6:0.5 DCM:MeOH:H$_2$O to give the title compound (34 mg, 51%) as a colourless solid. $C_{97}H_{188}N_8O_{19}$ requires 1769.4 Found ES$^+$: MNa$^+$, 1793.2. $\delta_H$ (CDCl$_3$) 1.24 (72H, br, (CH$_2$)$_{32}$CH$_2$CONH(CH$_2$)$_2$(CH$_2$)$_4$), 1.44 (66H, m, (Me)$_3$C, CH$_2$CH$_2$N), 1.72 (4H, p, NCH$_2$CH$_2$CH$_2$N), 2.0 (1H, br, CH), 2.14 (2H, t, CH$_2$CO), 2.83 (6H, s, NMe), 3.0–3.4 (24H, m, CH$_2$N), 3.6–3.9 (4H, br, CHOH), 4.10, 4.25 (2H, 2×br, CH$_2$OH), 5.80 (1H, br, CONH(CH$_2$)$_6$CH), 7.30 (1H, br, CONH).

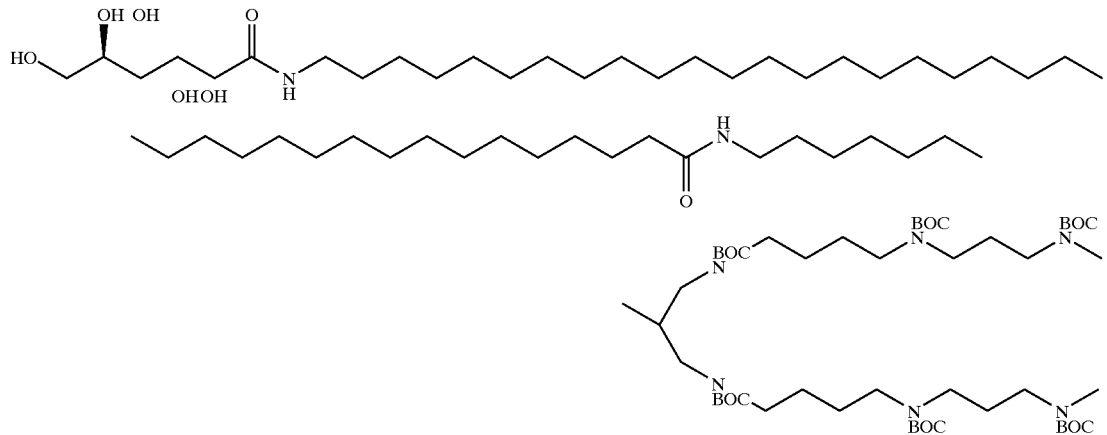

(H38) N-[8-(Methylaminopropylaminobutylamino)-7-(methylaminopropylaminobutylaminomethyl)octyl]-36-(glucuronylamino)hexatriacontanamide

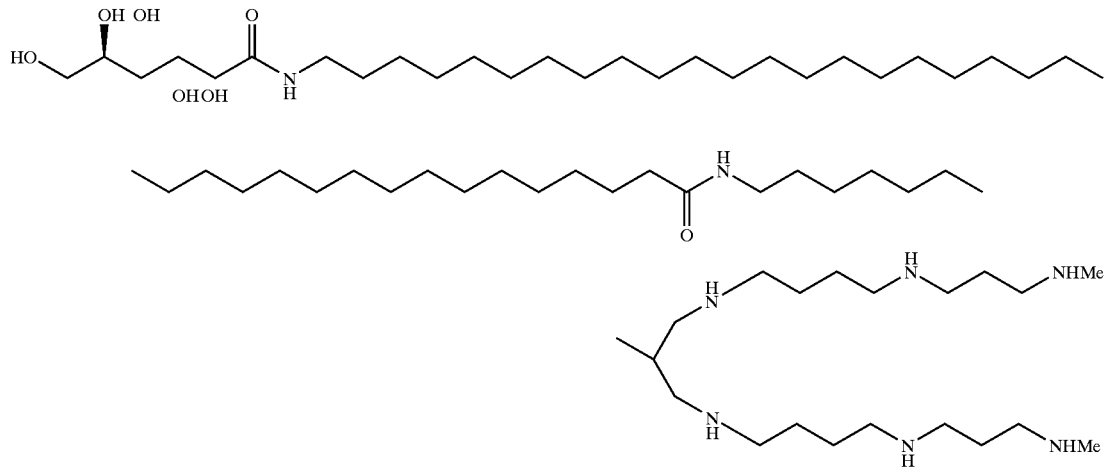

H37 (34 mg) was treated as in the synthesis of H33 to give the title compound in quantitative yield as a white solid. $C_{67}H_{140}N_8O_7$ requires 1169.1 Found ES$^+$: MH$_2^{2+}$, 585.7, MH$^+$, 1169.7. $\delta_H$ (CD$_3$OD) 1.29 (68H, br, (CH$_2$)$_{31}$(CH$_2$)$_2$CO, (CH$_2$)$_3$CH$_2$CH), 1.51 (8H, m, CH$_2$CH, CH$_2$CH$_2$N, CH$_2$CH$_2$CO), 1.83 (8H, brm, NCH$_2$(CH$_2$)$_2$CH$_2$N), 2.16 (7H, m, CH$_2$CO, NCH$_2$CH$_2$CH$_2$N, CH), 2.73 (6H, s, NMe), 3.0–3.3 (24H, m, NCH$_2$), 3.05–3.35 (4H, m, CHOH), 4.084.20 (2H, m+d, CH$_2$OH), 7.8–7.9 (2H, 2×br, NHCO).

I. PEG LIPIDS

This section contains the synthesis of:

(I2) N-[8-(Aminobutylamino)-7-(aminobutylaminomethyl)octyl]-24-[methoxypoly(ethyleneoxy)propanoylamino]tetracosanamide tetra (Trifluoroacetate) Salt To methoxyPEGpropionic acid (MW approx 1800) (282 mg, 0.157 mmol) in anhydrous dichloromethane (20 ml) were added EDC hydrochloride (38 mg, 0.199 mmol) and N-hydroxysuccinimide (23 mg, 0.199 mmol) and the reaction left overnight under argon at room temperature. To this was added E2 (154 mg, 0.142 mmol) and triethylamine (57 mg, 0.570 mmol) and the reaction left for a further six hours. To this was then added water (0.2 ml) and the hydrolysis of any remaining activated ester left overnight. The solvent was removed and the residues purified by gradient silica chromatography (5–10% methanol in dichloromethane) to yield the title compound (369 mg, 90%) as a white solid. For n=38 $C_{143}H_{282}N_6O_{50}$ requires 2884.0 Found ES$^+$: MNa$_2^{2+}$, 1465.6. $\delta_H$ (CDCl$_3$) 1.24 (44H, br, (CH$_2$)$_{19}$(CH$_2$)$_2$CO, (CH$_2$)$_3$CH$_2$CH), 1.43 (52H, m, (Me)$_3$C, CH$_2$CH, CH$_2$CH$_2$N, CH$_2$CH$_2$CO, NCH$_2$(CH$_2$)$_2$CH$_2$N), 1.97 (1H, br, CH), 2.22 (2H, t, (CH$_2$)$_{22}$CH$_2$CO), 2.60 (2H, t, OCH$_2$CH$_2$CO), 3.05–3.15 (16H, m, NCH$_2$), 3.37 (3H, s, OMe), 3.63 (~170H, m, OCH$_2$).

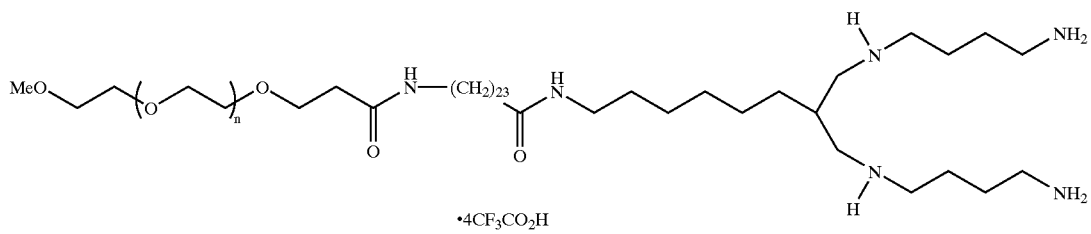

(I4) N-[8-(Methylaminopropylaminobutylamino)-7-(methylaminopropylaminobutylaminomethyl)octyl]-24-[methoxypoly(ethyleneoxy)propanoylamino]tetracosanamide hexa(Trifluoroacetate) Salt

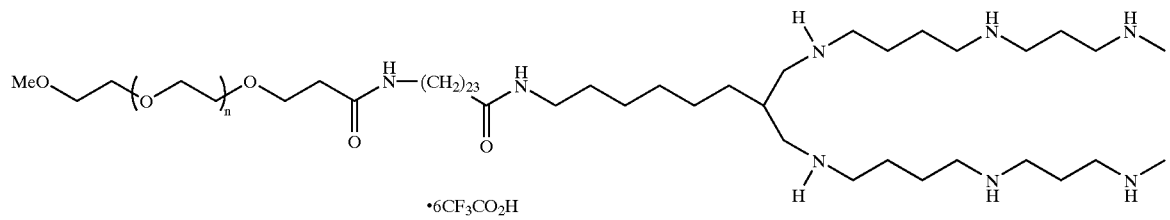

(I1) N-{8-[t-Butyloxycarbonylaminobutyl(t-butyloxycarbonyl)amino]-7-[t-butyloxycarbonylaminobutyl(t-butyloxycarbonyl)aminomethyl]octyl}-24-[methoxypoly(ethyleneoxy)propanoylamino]tetracosanamide

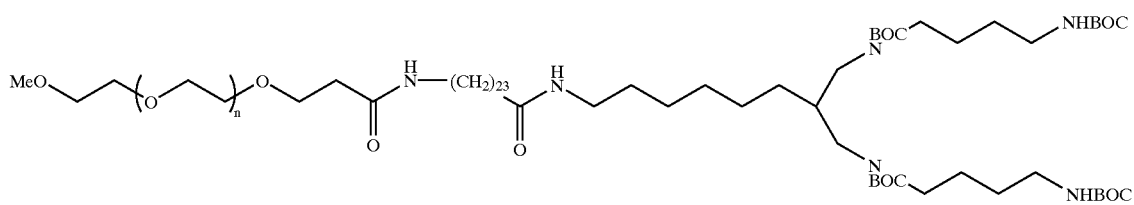

(I2) N-[8-(Aminobutylamino)-7-
(aminobutylaminomethyl)octyl]-24-[methoxypoly
(ethyleneoxy)propanoylamino]tetracosanamide tetra
(Trifluoroacetate) Salt

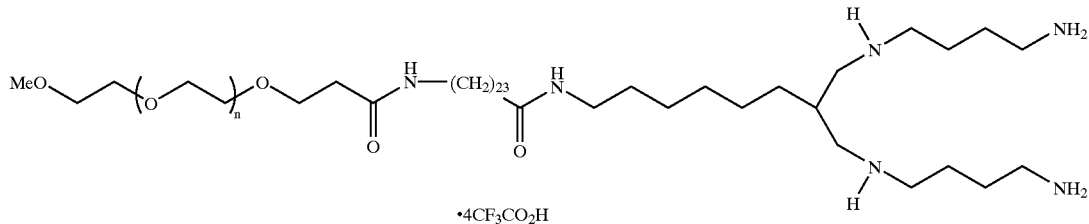

•4CF$_3$CO$_2$H

I1 (369 mg) was dissolved in 96:4 trifluoroacetic acid-:dichloromethane (9 ml) and left for 15 minutes at room temperature. The solvent was removed, the residues taken up into water, filtered (0.45 mm polypropylene) and freeze dried to give the title compound a pale yellow viscous oil (370 mg). For n=38 C$_{123}$H$_{250}$N$_6$O$_{42}$ requires 2483.8. Found ES$^+$: MH$_2^{2+}$, 1243.5. d$_H$ (CDCl$_3$) 1.24 (52H, brm, (CH$_2$)$_{21}$CH$_2$CO, (CH$_2$)$_5$CH), 1.85 (8H, br, NCH$_2$(CH$_2$)$_2$CH$_2$N), 2.21 (2H, t, (CH$_2$)$_{22}$CH$_2$CO), 2.35 (1H, br, CH), 2.51 (2H, t, OCH$_2$CH$_2$CO), 2.8–3.35 (16H, brm, NCH$_2$), 3.37 (3H, s, OMe), 3.63 (~170H, br, OCH$_2$).

(I3) N-{8-[Methyl(t-butyloxycarbonyl)aminopropyl
(t-butyloxycarbonyl)aminobutyl(t-butyloxycarbonyl)
amino]-7-[methyl(t-butyloxycarbonyl)aminopropyl
(t-butyloxycarbonyl)aminobutyl(t-butyloxycarbonyl)
aminomethyl]octyl}-24-[methoxypoly(ethyleneoxy)
propanoylamino]tetracosanamide To methoxyPEGpropionic acid (MW approx 1800) (210 mg, 0.117 mmol) in anhydrous dichloromethane (20 ml) were added hydrochloride (29 mg, 0.148 mmol) and N-hydroxysuccinimide (17 mg, 0.148 mmol) and the reaction left overnight under argon at room temperature. To this was added E4 (151 mg, 0.106 mmol) and triethylamine (32 mg, 0.318 mmol) and the reaction left for a further six hours. To this was then added water (0.2 ml) and the hydrolysis of any remaining activated ester left overnight. The solvent was removed and the residues purified by gradient silica chromatography (5–10% methanol in dichloromethane) to yield the title compound (205 mg, 60%) as an off white solid. For n=38 C$_{161}$H$_{316}$N$_8$O$_{54}$ requires 3226.2 Found ES$^+$: MNa$_2^{2+}$, 1636.8. δ$_H$ (CDCl$_3$) 1.24 (48H, brs, (CH$_2$)$_{20}$CH$_2$CO, (CH$_2$)$_4$CH), 1.43 (70H, brs+m, (Me)$_3$C, CH$_2$CH$_2$N), 1.98 (1H, br, CH), 2.19 (2H, t, (CH$_2$)$_{22}$CH$_2$CO), 2.54 (2H, t, OCH$_2$CH$_2$CO), 2.83 (6H, s, NMe), 3–3.5 (24H, brm, NCH$_2$), 3.36 (3H, s, OMe), 3.6 (~170H, s, OCH$_2$), 5.95, 6.95 (2H, br, CONH).

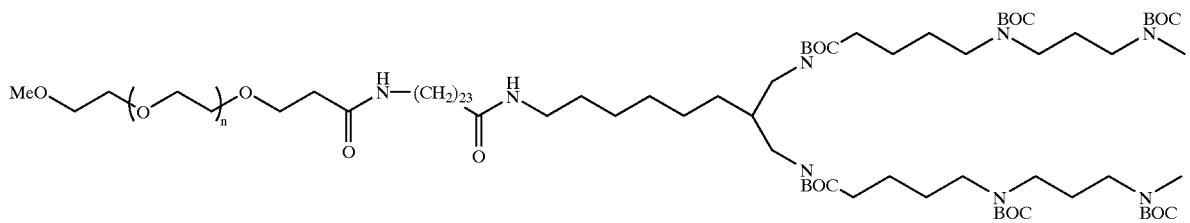

(I4) N-[8-(Methylaminopropylaminobutylamino)-7-
(methylaminopropylaminobutylaminomethyl)octyl]-
24-[methoxypoly(ethyleneoxy)propanoylamino]
tetracosanamide hexa(Trifluoroacetate) Salt

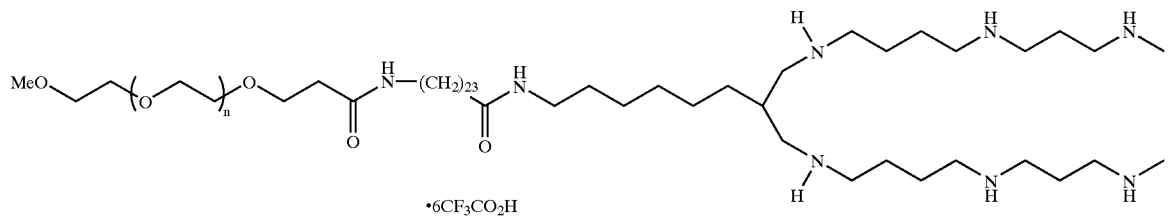

•6CF$_3$CO$_2$H

I3 (206 mg) was dissolved in 96:4 trifluoroacetic acid-:dichloromethane (8 ml) and left for 15 minutes at room temperature. The solvent was removed, the residues taken up into water, filtered (0.45 mm polypropylene) and freeze dried to give the title compound as an off white solid (213 mg). For n=38 $C_{131}H_{268}N_8O_{42}$ requires 2625.9 Found ES$^+$: MH$_2^{2+}$, 1314.5. $\delta_H$ (D$_2$O) 1.87 (44H, br, (CH$_2$)$_{19}$(CH$_2$)$_2$CO, (CH$_2$)$_3$CH$_2$CH), 2.06 (8H, br, CH$_2$CH, CH$_2$CH$_2$NH, CH$_2$CH$_2$CO), 2.38 (8H, br, NCH$_2$(CH$_2$)$_2$CH$_2$N), 2.72 (7H, br, (CH$_2$)$_{22}$CH$_2$CO, NCH$_2$CH$_2$CH$_2$N, CH), 3.05 (2H, t, OCH$_2$CH$_2$CO), 3.34 (6H, s, NMe), 3.72 (24H, br, CH$_2$N), 3.95 (3H, s, OMe), 4.25 (~170H, br, OCH$_2$).

The advantageous properties of the lipids according to the invention may be demonstrated in the following tests:

PRONASE and DNase Treatment

One of the ultimate goals of current gene therapy research is to develop a delivery system which will remain stable and effective in vivo, since this would remove the need for expensive and time-consuming ex-vivo manipulations. Since intravenous administration offers the possibility of delivery to the largest number of tissue sites, survival of the gene delivery complex in the presence of serum could be an important feature of any effective technology. Many published studies have demonstated the susceptibility of gene delivery complexes to inactivation by serum even at levels as low as 10%. This effect is due, at least in part, to the destabilisation of complexes by a poorly understood mechanism, and this can lead to degradation of the DNA within the complex by serum-associated nucleases. We have therefore formed complexes between the lipids of the invention and plasmid DNA and subjected these to treatment with purified DNase and pronase as well as with 50% foetal calf serum. Integrity of the plasmid DNA was then measured.

Methods

Plasmid DNA (pEG/acZ) was prepared at a concentration of 120 μg/ml in water. A lipid according to the invention [for example the hexamine H18 described in the Example above] was prepared in a range of concentrations such that charge ratios of lipid:DNA of 0.25:1, 1:1, 2:1, 4:1, 8:1 would be obtained (based on the assumption that DNA at 120 μg/ml is equivalent to 0.387 mM of negative charge, and the hexamine H18 for example at 10 mg/ml is equivalent to 36.23 mM of positive charge). An equal volume of DNA was added dropwise to a vortexing tube containing the lipid in water. For DNase treatment, DNase I (FPLCpure, Pharmacia) was added at a concentration of 1 unit/1 μg of DNA and tubes were incubated at 37° C. for 10 minutes. To inhibit further action of DNase, EGTA was added to a final concentration of 25 mM. For pronase treatment, protease XIV (Sigma) was added to samples to a final concentration of 150 μg/ml, and samples incubated for 30 min at 37° C. Complexes were disrupted in 0.5% SDS with incubation at 55° C. for 20 min. Serum treatment involved incubating the samples in the presence of 50% foetal calf serum (final concentration) for 30 min at 37° C. EGTA was added to a final concentration of 50 mM in an attempt to prevent subsequent action of serum-associated nucleases. Finally, all samples were analysed by electrophoresis on 0.8% agarose gels.

Results

Analysis of the mobility of plasmid DNA through gels demonstrated that, as the amount of lipid increased, the DNA tended to be retarded in the wells. Thus, for example, at a charge ratio of 2:1 (H18/DNA), no DNA entered the gel, and at higher ratios, the plasmid DNA was no longer visible by ethidium bromide fluorescence (see below), suggesting that the DNA had become fully condensed. The H18/DNA condensates were resistant to treatment by pronase. In addition, DNA condensed with H18 at a charge ratio of at least 2:1 was resistant to treatment by DNase. At charge ratios of 2:1 or greater, addition of serum to 50% did not lead to an increase in the amount of DNA degradation, suggesting that lipids according to the invention are stable in serum.

Physical Chemical Assays

Two physical chemical assays can be used to assess the ability of the lipids of the invention to compact supercoiled DNA and to determine the stability of the condensed particles.

Assay 1

The first assay involves the use of ethidium bromide, a molecule which fluoresces when intercalated into the DNA helix. Solutions containing DNA and a lipid according to the invention are prepared so that the charge ratio between the negatively charged phosphate groups of the DNA and the postively charged polyamines of the lipids varies between zero and three [see the "Methods" in the previous section]. After ethidium bromide has been added to each solution the fluorescence reading is measured. As the charge ratio increases towards charge neutrality, because of the increasing amounts of lipid present, there is a progressive decrease in the fluorescence of the ethidium bromide when this molecule is excluded from binding to the DNA as compaction occurs. The point at which compaction is complete corresponds to the point at which the fluorescence reading levels-off at a minimum. In the case of thelipids of the invention the fluorescence minimum is reached at charge ratios of lipid to DNA in the range of 0.8 to 2.5. This assay has been used to demonstrate that lipid are compaction competent under conditions of physiological salt (150 mM NaCl) and at acidic conditions down to pH 3.0. Repeating the assay also shows that the compacted DNA particles are stable for many hours both in physiological salt and under low pH conditions.

Assay 2

The second assay involves gel electrophoresis using ethidium bromide as a stain. Samples of lipid and DNA are prepared as before and loaded into separate lanes in a polyacrylamide gel. After electrophoresis the fluorescence reading of each lane is determined. Two effects are observed. First, as the charge ratio increases towards neutrality the distance that the DNA/lipid complex travels through the gel decreases progressitvely. This is a result of two physical processes; compaction, which renders the DNA less able to move through the viscous gel and neutralisation of DNA negative charge, which reduces the electrostatic attraction between the complex and the cathode. Second, as the charge ratio increases beyond neutrality the brilliance of the fluorescent response decreases as the ethidium bromide stain is excluded from the DNA helix. This assay has been used to confirm that the lipids according to the invention cause DNA compaction close to the point of charge neutrality, in agreement with theory.

Transfection of Mammalian Cells With Lipid Condensed DNA Complexes

Condensation of DNA

Plasmid DNA (pEG/acZ) was prepared at concentrations of typically 60 or 120 μg/ml in water. Solutions of lipids according to the invention were prepared in water over a range of concentrations (typically 30 to 960 μg/ml). An equal volume of DNA was added dropwise to a tube containing a solution of the lipids whilst vortexing the tube.

CHO Transfection Protocol

Chinese Hamster Ovary (CHO) cells were seeded in to 24 well plates at 100,000 cells per well 24 h before experiment.

Cells were washed once in Optimem™ medium prior to transfection. Wash medium was removed and replaced with 0.5 ml of Optimem™ to which the required amount of lipid condensed DNA was added (typically 1 to 5 μg DNA equivalent). Usually three replicate transfection wells were set up per condensed DNA sample tested. Cells were incubated for a further 34 h at 37° C., 5% $CO_2$ before removal of the complex and additon of 1 ml of fresh medium (Iscoves™ medium: modified DMEM plus glutamate, asparagine, adenosine, guanosine, cytidine, uridine, thymidine and 10% dialysed foetal calf serum). Cells were cultured for a further 48–72 hours before harvesting and assay. Levels of Beta galactosidase reporter gene activity were determined using an enzyme assay system from Promega as follows. Cells were washed twice with 1 ml of phosphate buffered saline and solubilised in 200 ul of 1×cell lysis buffer. 50 ul of cell extract was incubated with the provided buffer and substrate o-nitrophenyl-β-D-galactopyranoside and the optical density measured spectrophotometrically. Levels of β-gal expression were quantitated by reference to the standard curve and related to the amount of protein in the extract (measured using the BCA assay kit from Pierce) to give a final value expressed as mU of β-gal per mg of protein.

Results

Typical transfection results for lipid DNA samples are shown in the following table:

| Lipid (see Examples) | Lipid:DNA mass ratio | β-galactosidase in cell extract mUnits per mg protein |
|---|---|---|
| H3 | 8:1 | 11 ± 4 |
| H18 | 8:1 | 40 ± 9 |

Non-condensed DNA control resulted in an undetectable level of β-galactosidase, whereas the tetramine (H3) and hexamine (H18) condensed DNA achieved significant β-galactosidase expression in the CHO cells.

What is claimed is:

1. A bipolar lipid comprising a cationic head (1), a hydrophobic backbone (2) and a hydrophilic tail (3) wherein:
   (A) the cationic head comprises two or more cationic centers, wherein each center is covalently linked to one or more other centers by one or more carbon-containing spacer groups;
   (B) the hydrophobic backbone comprises at least one hydrocarbon chain; and
   (C) the hydrophilic tail comprises at least one tail unit selected from the group consisting of a synthetic polyol, naturally occurring polyol, poly(alkylene oxide) and derivative of poly(alkylene oxide);
wherein each of said components (1) to (3) is covalently linked head (1) to backbone (2) to tail (3) and arranged such that said at least one hydrocarbon chain of the hydrophobic backbone (2) is covalently attached to a carbon atom of a spacer group in the cationic head (1) and to said at least one tail unit in the hydrophilic tail (3) such that the chain contains at least ten chain-linked atoms between its points of attachments to said spacer group and said at least one tail unit.

2. The lipid according to claim 1, wherein each cationic center is an amino group.

3. The lipid according to claim 1, wherein the number of cationic centers in the cationic head is from three to six.

4. The lipid according to claim 1, wherein each carbon-containing spacer group is an optionally substituted aliphatic, cycloaliphatic, heteroaliphatic, heterocycloaliphatic, aromatic or heteroaromatic group.

5. The lipid according to claim 1, wherein said at least one hydrocarbon chain in the hydrophobic backbone is an optionally substituted straight or branched aliphatic or heteroaliphatic chain containing from ten to about one hundred chain-linked atoms.

6. The lipid according to claim 5, wherein the hydrophobic backbone has one or two hydrocarbon chains indirectly linked through a linker atom or group to a carbon atom in a spacer group connecting two cationic centers in the cationic head (1).

7. The lipid according to claim 1, wherein each tail unit in the hydrophilic tail (3) is attached to a hydrocarbon chain of the hydrocarbon backbone (2) at the terminal carbon atom of said chain distal to the chain carbon atom attached to the cationic head (1).

8. The lipid according to claim 1, wherein said lipid is represented by formula (1) or a salt, solvate or hydrate thereof:

$$[R^1]_m\text{—}(L^1)_n\text{—}[\text{—}C(R^2)(R^3)(R^4)] \quad (1)$$

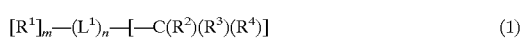

wherein $R^1$ is a hydrocarbon chain optionally substituted by one or more tail units selected from the group consisting of a synthetic polyol, naturally occurring polyol, poly(alkylene oxide) and derivative of poly(alkylene oxide), provided that at least one hydrocarbon chain $R^1$ is substituted by at least one of said tail units and each of said tail units is attached to the hydrocarbon chain to achieve at least a ten chain-linked atom spacing along the chain between the tail unit and the group —$(L^1)_n$—[—$C(R^2)(R^3)(R^4)$];

m is an integer of from 1to 6;

$L^1$ is a linker atom or group;

n is zero or the integer 1;

—[—$C(R^2)(R^3)(R^4)$] is a cationic head in which $R^2$ is a hydrogen atom or an optionally substituted aliphatic, cycloaliphatic, heteroaliphatic, heterocycloaliphatic, aromatic or heteroaromatic group, optionally containing one or more cationic centers, and $R^3$ and $R^4$, which may be the same or different, are each an optionally substituted aliphatic, cycloaliphatic, heteroaliphatic, heterocycloaliphatic, aromatic or heteroaromatic group, optionally containing one or more cationic centers, or $R^3$ and $R^4$ together with the carbon atom to which they are attached form a cycloaliphatic, heterocycloaliphatic, aromatic or heteroaromatic group containing two or more cationic centers.

9. The lipid according to claim 8, wherein said lipid is represented by formula (1a) or a salt, solvate or hydrate thereof:

$$[R^7]_p\text{—}(L^3)_q\text{—}[R^6]_m\text{—}(L^1)_n\text{—}[\text{—}C(R^2)(R^3)(R^4)] \quad (1a)$$

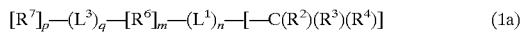

wherein $R^2$, $R^3$, $R^4$, $L^1$, m and n are as defined for formula (1);

$R^6$ is a hydrocarbon chain;

$L^3$ is a linker atom or group;

$R^7$ is a tail unit selected from the group consisting of a synthetic polyol, naturally occurring polyol, poly(alkylene oxide) and derivative of poly(alkylene oxide);

q is zero or an integer from one to six;

p is an integer from one to six;

provided that each $R^7$ or $L^3$ group, when present, is attached to a group $R^6$ to achieve at least a ten chain-linked atom spacing along $R^6$ between $R^7$ or $L^3$ and the group $-(L^1)_n-[C(R^2)(R^3)(R^4)]$.

10. The lipid according to claim 9, wherein $R^2$ is a hydrogen atom and $R^3$ and $R^4$ are each a group $Sp^1[WSp^2]_b$ $Sp^3$ or $-Sp^1[WSp^2]_bWH$, wherein $Sp^1$, $Sp^2$ and $Sp^3$, which may be the same or different, are each a spacer group, W is a cationic center and b is zero or an integer from one to six.

11. The lipid according to claim 10, wherein $Sp^1$, $Sp^2$ and $Sp^3$ are each an optionally substituted aliphatic, cycloaliphatic, aromatic or heteroaromatic group.

12. The lipid according to claim 11, wherein $Sp^1$, $Sp^2$ and $Sp^3$ are each an optionally substituted $C_{1-6}$ alkylene chain.

13. The lipid according to claim 9, wherein W is a —NH— group.

14. The lipid according to claim 9 wherein b is an integer from 1 to 3.

15. The lipid according to claim 9, wherein the group $-C(R^2)(R^3)(R^4)$ is a group $-CH[Sp^1NHSp^2NH_2]_2$, $-CH[Sp^1NHSp^2NHSp^2NH_2]_2$ or $-CH[Sp^1NHSp^2NHSp^2NHCH_3]_2$, wherein $Sp^1$ is $-CH_2-$ and each $Sp^2$ is $-(CH_2)_3-$ or $-(CH_2)_4-$.

16. The lipid according to claim 9, wherein n in $-(L^1)_n-$ is the integer 1.

17. The lipid according to claim 16, wherein $L^1$ is a group $-X^1Alk^2-$ or $-[X^1]_2Alk^1X^1Alk^2-$, wherein $X^1$ is an —O— or —S— atom or a —C(O)—, —C(O)O—, —C(S)—, —S(O)—, —S(O)$_2$—, —N($R^5$)—, —CON($R^5$)—, —OC(O)N($R^5$)—, —CSN($R^5$)—, —N($R^5$)CO—, —N($R^5$)C(O)O—, —N($R^5$)CS—, —S(O)N($R^5$)—, —S(O)$_2$N($R^5$)—, —N($R^5$)S(O)—, —N($R^5$)S(O)$_2$, —N($R^5$)CON($R^5$)— or —N($R^5$)SO$_2$N($R^5$)— group, wherein each $R^5$ is independently selected from the group consisting of a hydrogen atom, straight and branched alkyl group and —Alk$^1$X$^1$— chain, wherein Alk$^1$ and Alk$^2$ may be the same or different and are each an optionally substituted straight or branched $C_{1-6}$ alkylene, $C_{2-6}$ alkenylene or $C_{2-6}$ alkynylene chain optionally interrupted or terminated by one or more carbocyclic or heterocarbocyclic groups, heteroatoms or heteroatom-containing groups $X^1$.

18. The lipid according to claim 17, wherein $X^1$ is a —CONH— group, Alk$^1$ is a —CH$_2$—CH< chain and Alk$^2$ is a —(CH$_2$)$_4$—, —(CH$_2$)$_5$— or —(CH$_2$)$_6$— chain.

19. The lipid according to claim 9, wherein m is the integer 1 or 2.

20. The lipid according to claim 9, wherein $R^6$ is an optionally substituted $C_{10-60}$ aliphatic chain.

21. A lipid according to claim 20, wherein $R^6$ is a linear, optionally substituted $C_{16-38}$ alkylene chain.

22. A lipid according to claim 9, wherein q is the integer 1 and p is the integer 1 or 2.

23. The lipid according to claim 9, wherein $L^3$ is an atom or group $-X^1-$, $-X^1Alk^1X^1-$ or $[X^1Alk^1]_1X^1Alk^2X^1$, wherein $X^1$ is an —O— or —S— atom or a —C(O)—, —C(O)O—, —C(S)—, —S(O)—, —S(O)$_2$—, —N($R^5$)—, —CON($R^5$)—, —OC(O)N($R^5$)—, —CSN($R^5$)—, —N($R^5$)CO—, —N($R^5$)C(O)O—, —N($R^5$)CS—, —S(O)N($R^5$)—, —S(O)$_2$N($R^5$)—, —N($R^5$)S(O)—, —N($R^5$)S(O)$_2$—, —N($R^5$)CON($R^5$)— or —N($R^5$)SO$_2$N($R^5$)— group, wherein each $R^5$ is independently selected from the group consisting of a hydrogen atom, straight and branched alkyl group and —Alk$^1$X$^1$— chain, wherein Alk$^1$ and Alk$^2$ may be the same or different and are each an optionally substituted straight or branched $C_{1-6}$ alkylene, $C_{2-6}$ alkenylene or $C_{2-6}$ alkynylene chain optionally interrupted or terminated by one or more carbocyclic or heterocarbocyclic groups, heteroatoms or heteroatom-containing groups $X^1$.

24. The lipid according to claim 23, wherein $L^3$ is a —NHCO—, —CONH—, —CONH(CH$_2$)$_2$NHCO— or —[CONH(CH$_2$)$_2$—]$_2$NCO(CH$_2$)$_2$CONH group.

25. The lipid according to claim 9, wherein $R^7$ is a poly(alkylene oxide) or derivative thereof.

26. The lipid according to claim 25, wherein $R^7$ is a poly(ethylene oxide).

27. The lipid according to claim 9, wherein $R^7$ is a naturally occurring polyol.

28. The lipid according to claim 27, wherein $R^7$ is a mono- or disaccharide.

29. A lipid complex comprising a bipolar lipid according to claim 1 in association with at least one bioactive substance.

30. The complex according to claim 29, wherein said at least one bioactive substance is selected from the group consisting of a bioactive protein, peptide, polysaccharide, nucleic acid, oligonucleotide and derivative thereof, lipid, glycolipid, lipoprotein, lipopolysaccharide and viral, bacterial, protozoal, cellular or tissue fraction.

31. The complex according to claim 30, wherein said at least one bioactive substance is a polyanion.

32. The complex according to claim 31, wherein said at least one bioactive substance is a nucleic acid.

33. The complex according to claim 29, wherein said complex contains two or more different bipolar lipids.

34. The complex according to claim 33, wherein one bipolar lipid has tail units formed by a poly(alkylene oxide) or a derivative thereof and the other bipolar lipid(s) has (have) tail units formed by a synthetic or naturally occurring polyol.

35. The complex according to claim 34, wherein the poly(alkylene oxide) is poly(ethylene oxide).

36. A composition comprising a complex according to claim 29 and at least one other lipid.

37. The composition according to claim 36, wherein said at least one other lipid is a neutral or cationic lipid.

38. A composition comprising a complex according to claim 29 and one or more pharmaceutically acceptable carriers, excipients or diluents.

39. A method for preparing a lipid as claimed in claim 1, comprising coupling:

(A) a cationic head comprising two or more cationic centers, wherein each center is covalently linked to one or more other centers by one or more carbon-containing spacer groups;

(B) a hydrophilic tail comprising at least one hydrocarbon chain; and (C) a hydrophilic tail comprising at least one tail unit selected from the group consisting of a synthetic polyol, naturally occurring polyol, poly(alkylene oxide) and derivative of poly(alkylene oxide), wherein (A), (B) and (C) contain one or more reactive functional groups suitable for facilitating coupling such that said at least one hydrocarbon chain of the hydrophobic backbone is covalently attached to a carbon atom of a spacer group in the cationic head and to said at least one tail unit in the hydrophilic tail such that the chain contains at least ten chain-linked atoms between its points of attachments to said spacer group and said at least one tail unit.

40. A method for preparing a lipid as claimed in claim 1, where said method comprises a step of deprotecting a protected derivative of said lipid.

41. A method of preparing a lipid complex as claimed in claim 30, comprising mixing said lipid with a bioactive substance.

42. A method of delivering a bioactive substance to a human or non-human animal, comprising administering to said human or non-human animal said bioactive substance in the form of a complex of claims 29.

43. A method of delivering a substance to a cell comprising contacting a cell in vivo with said bioactive substance in the form of a complex of claim 29.

* * * * *